US011208379B2

(12) United States Patent
Grapperhaus et al.

(10) Patent No.: US 11,208,379 B2
(45) Date of Patent: *Dec. 28, 2021

(54) COMPOUNDS, COMPOSITIONS, METHODS FOR TREATING DISEASES, AND METHODS FOR PREPARING COMPOUNDS

(71) Applicant: UNIVERSITY OF LOUISVILLE RESEARCH FOUNDATION, INC., Louisville, KY (US)

(72) Inventors: Craig A. Grapperhaus, Jeffersonville, IN (US); Robert M. Buchanan, Louisville, KY (US); Nicholas S. Vishnosky, Marlborough, CT (US); Jason O. E. Young, Owensboro, KY (US); Paula J. Bates, Louisville, KY (US); Sarah A. Andres, Floyds Knobs, IN (US); Caleb Aaron Calvary, Louisville, KY (US)

(73) Assignee: UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/672,481

(22) Filed: Nov. 3, 2019

(65) Prior Publication Data
US 2020/0062703 A1 Feb. 27, 2020

Related U.S. Application Data

(63) Continuation-in-part of application No. PCT/US2018/030765, filed on May 3, 2018.

(60) Provisional application No. 62/501,553, filed on May 4, 2017, provisional application No. 62/768,921, filed on Nov. 18, 2018.

(51) Int. Cl.
 *C07C 335/40* (2006.01)
 *A61P 35/00* (2006.01)
 *C07D 265/30* (2006.01)

(52) U.S. Cl.
 CPC .......... *C07C 335/40* (2013.01); *A61P 35/00* (2018.01); *C07D 265/30* (2013.01)

(58) Field of Classification Search
 CPC ...... C07C 335/40; C07D 265/30; A61P 35/00
 See application file for complete search history.

(56) References Cited

U.S. PATENT DOCUMENTS

2019/0106385 A1  4/2019  Grapperhaus et al.

FOREIGN PATENT DOCUMENTS

| WO | 2008/061306 A1 | 5/2008 |
| WO | 2010/066010 A1 | 6/2010 |
| WO | 2015/070177 A2 | 5/2015 |
| WO | 2017/214546 A1 | 12/2017 |
| WO | 2018/204564 A1 | 11/2018 |

OTHER PUBLICATIONS

International Search Report from PCT/US2018/030765, dated Jul. 24, 2018, 4 pages.
Written Opinion from PCT/US2018/030765, dated Jul. 24, 2018, 6 pages.
Alsop et al. (2005) "Investigations into some aryl substituted bis(thiosemicarbazones) and their copper complexes" Inorganica Chimica Acta, vol. 358, pp. 2770-2780.
Bates et al. (1999) "Antiproliferative Activity of G-rich Oligonucleotides Correlates with Protein Binding" J. Biol. Chem., vol. 274, No. 37, pp. 26369-26377.
Blower et al. (2003) "Structural trends in copper(ii) bis(thiosemicarbazone) radiopharmaceuticals" Dalton Trans., vol. 2003, No. 23, pp. 4416-4425.
Bocokic et al. (2012) "Bis-(thiosemicarbazonato) Zn(ii) complexes as building blocks for construction of supramolecular catalysts" Dalton Trans., vol. 41, Issue 13, pp. 3740-3750.
Boodram et al. (2016) "Breast Cancer Stem Cell Potent Copper (II)-Non-Steroidal Anti-Inflammatory Drug Complexes." Angewandte Chemie, vol. 128, No. 8, pp. 2895-2900.
Carta et al. (2013) "Xanthates and Trithiocarbonates Strongly Inhibit Carbonic Anhydrases and Show Antiglaucoma Effects in Vivo" J. Med. Chem., vol. 56, pp. 4691-4700.
Cater et al. (2013) "Increasing Intracellular Bioavailable Copper Selectively Targets Prostate Cancer Cells" ACS Chem. Biol., vol. 8, pp. 1621-1631.
Dearling et al. (2002) "Copper bis(thiosemicarbazone) complexes as hypoxia imaging agents: structure-activity relationships" J. Biol. Inorg. Chem., vol. 7, pp. 249-259.
Fujibayashi et al. (1997) "Copper-62-ATSM: A New Hypoxia Imaging Agent with High Membrane Permeability and Low Redox Potential" J. Nucl. Med., vol. 38, pp. 1155-1160.
Gao et al. (2009) "Cytotoxic Activities, Cellular Uptake, Gene Regulation, and Optical Imaging of Novel Platinum(II) Complexes" Chem. Res. Toxicol, vol. 22, pp. 1705-1712.
Haddad et al. (2016) "Beyond Metal-Hydrides: Non-Transition-Metal and Metal-Free Ligand-Centered Electrocatalytic Hydrogen Evolution and Hydrogen Oxidation" JACS, vol. 138, pp. 7844-7847.

(Continued)

*Primary Examiner* — Alicia L Otton
(74) *Attorney, Agent, or Firm* — ALGM LLP; Harry J. Guttman

(57) ABSTRACT

Some embodiments of the invention include inventive compounds (e.g., compounds of Formula (I) or (Ia)). Other embodiments include compositions (e.g., pharmaceutical compositions) comprising the inventive compound. Still other embodiments of the invention include compositions (e.g., pharmaceutical compositions) for treating, for example, certain diseases using the inventive compounds. Some embodiments include methods of using the inventive compound (e.g., in compositions or in pharmaceutical compositions) for administering and treating (e.g., diseases such as cancer). Further embodiments include methods for making the inventive compounds. Additional embodiments of the invention are also discussed herein.

37 Claims, 43 Drawing Sheets

(56) References Cited

OTHER PUBLICATIONS

Haddad et al. (2017) "Metal-Assisted Ligand-Centered Electrocatalytic Hydrogen Evolution upon Reduction of a Bis(thiosemicarbazonato)Cu(II) Complex" Inorg. Chem., vol. 56, pp. 11254-11265.
Huuskonen et al. (2017) "The Copper bis(thiosemicarbazone) Complex CuII(atsm) Is Protective Against Cerebral Ischemia Through Modulation of the Inflammatory Milieu" Neurotherapeutics, vol. 14, pp. 519-532.
Liskova et al. (2012) "Cellular Response to Antitumor cis-Dichlorido Platinum(II) Complexes of CDK Inhibitor Bohemine and Its Analogues" Chem. Res. Toxicol., vol. 25, pp. 500-509.
Marshall et al. (2017) "Small non-coding RNA transcriptome of the NCI-60 cell line panel" Sci Data, vol. 4, Article 170157 (8 pages).
Marzano et al. (2009) "Copper complexes as anticancer agents." Anti-Cancer Agents in Medicinal Chemistry (Formerly Current Medicinal Chemistry-Anti-Cancer Agents), vol. 9, No. 2, pp. 185-211.
Morgan (1998) "Tetrazolium (MTT) Assay for Cellular Viability and Activity" Methods Mol. Biol., vol. 79, pp. 179-183.
Palanimuthu et al. (2013) "In Vitro and in Vivo Anticancer Activity of Copper Bis(thiosemicarbazone) Complexes" J. Med. Chem., vol. 56, pp. 722-734.
Paterson et al. (2010) "Versatile New Bis(thiosemicarbazone)" Inorg. Chem., vol. 49, pp. 1884-1893.
Reüfenacht (1972) "Arbetien über Phosphosaure- und Thiosphosphorsaureester mit einem Heterocyclischen Substituenten Thiadiazol-Ringschluss und eine Dabei Auftretende Methylübertragung" Helv. Chim. Acta, vol. 55, Issue 4, pp. 1178-1187.
Salipur et al., (2014) "A Novel Small Molecule That Induces Oxidative Stress and Selectively Kills Malignant Cells" Free Radical Biology and Medicine, vol. 68, pp. 110-121.
Stefani et al. (2015) "Identification of differential anti-neoplastic activity of copper bis(thiosemicarbazones) that is mediated by intracellular reactive oxygen species generation and lysosomal membrane permeabilization" Journal of Inorganic Biochemistry, vol. 152, pp. 20-37.
Straistari et al. (2017) "A Thiosemicarbazone-Nickel(II) Complex as Efficient Electrocatalyst for Hydrogen Evolution" ChemCatChem, vol. 9, pp. 2262-2268.
Vishnosky et al. (2017) "Syntheses, structures, and electrochemical studies of N,N'-bis(alkylthiocarbamate)butane-2,3-diimine Cu(II) complexes as pendent alkoxy derivatives of Cu(ATSM)" Inorg. Chim. Acta, vol. 461, pp. 45-51.
Wehbe et al. (2017) "A Perspective—can copper complexes be developed as a novel class of therapeutics?" Dalton Trans., vol. 46, pp. 10758-10773.
Xie et al. (2016) "Exploiting Copper Redox for 19F Magnetic Resonance-Based Detection of Cellular Hypoxia" JACS, vol. 138, pp. 2937-2940.
PCT/US2017/036815, ISR mailed Aug. 14, 2017, 6 pages.
PCT/US2017/036815, Written Opinion dated Aug. 14, 2017, 8 pages.
Abbaspour et al., (2012) "Electrocatalytic behavior of carbon paste electrode modified with metal phthalocyanines nanoparticles toward the hydrogen evolution" Electrochim. Acta, vol. 76, pp. 404-409.
Abbaspour et al., (2013) "Electrocatalytic hydrogen evolution reaction on carbon paste electrode modified with Ni ferrite nanoparticles" Fuel, vol. 104, pp. 575-582.
Abe et al. (1998) "Highly active electrocatalysis by cobalt tetraphenylporphyrin incorporated in a nation membrane for proton reduction" Polym. Adv. Technol., vol. 9, pp. 559-562.
Andrieux et al., (1980) "Homogeneous Redox Catalysis of Electrochemical Reactions" Journal of Electroanalytical Chemistry, vol. 113, pp. 19-40.
Appel et al. (2005) "Molybdenum-Sulfur Dimers as Electrocatalysts for the Production of Hydrogen at Low Overpotentials" Journal of the American Chemical Society, vol. 127, pp. 12717-12726.

Appel et al., (2014) "Determining the Overpotential for a Molecular Electrocatalyst" ACS Catal., vol. 4, pp. 630-633.
Bard et al., Electrochemical Methods: Fundamentals and Applications; 2nd ed.; Wiley: Somerset, New Jersey, 2001. (850 pages).
Barton et al., (2004) "Enzymatic Biofuel Cells for Implantable and Microscale Devices" Chem Rev, vol. 104, pp. 1867-4886.
Barton et al., (2008) "Selective Solar-Driven Reduction of CO2 to Methanol Using a Catalyzed p-GaP Based Photoelectrochemical Cell" Journal of the American Chemical Society, vol. 130, pp. 6342-6344.
Barton et al., (2010) "Artificial hydrogenases" Current Opinion in Biotechnology, vol. 21, pp. 292-297.
Berben et al., (2010) "Hydrogen evolution by cobalt tetraimine catalysts adsorbed on electrode surfaces" Chem. Commun., vol. 46, pp. 398-400.
Betts et al., (2008) "Controlled Axial Coordination: Solid-Phase Synthesis and Purification of Metallo-Radiopharmaceuticals" Angew. Chem. Int. Ed., vol. 47, pp. 8416-8419.
Calatayud et al., (2012) "Complexes of group 12 metals containing a hybrid thiosemicarbazone-pyridylhydrazone ligand" Inorganica Chimica Acta, vol. 381, pp. 150-161.
Calatayud et al., (2013) "A fluorescent dissymmetric thiosemicarbazone ligand containing a hydrazone quinoline arm and its complexes with cadmium and mercury" European Journal of Inorganic Chemistry, pp. 80-90.
Cao et al., (2014) "First mononuclear copper(II) electrocatalyst for catalyzing hydrogen evolution from acetic acid and water" International Journal of Hydrogen Energy, vol. 39, pp. 13972-13978.
Castiñeiras et al., (2002) "Structural study of a zinc(II) complex with acetone 3-hexamethyleneiminylthiosemicarbazone" J. Mol. Struct., vol. 604, pp. 113-118.
Chakraborty et al., (2016) "High yield synthesis of amine functionalized graphene oxide and its surface properties" RSC Adv., vol. 6, pp. 67916-67924.
Chebotareva et al., (1997) "First-Row Transition Metal Phthalocyanines as Catalysts for Water Electrolysis: A Comparative Study" Electrochim. Acta, vol. 42, pp. 3519-3524.
Chen et al., (2011) "Core-shell MoO3—MoS2 Nanowires for Hydrogen Evolution: A Functional Design for Electrocatalytic Materials" Nano Lett., vol. 11, pp. 4168-4175.
Christlieb et al., (2007) "The exocyclic functionalisation of bis(thiosemicarbazonate) complexes of zinc and copper: the synthesis of monomeric and dimeric species" Dalton Trans., pp. 5043-5054.
Christlieb et al., (2007) "New bimetallic compounds based on the bis(thiosemicarbazonato) motif" Dalton Trans., pp. 2007, pp. 327-331.
Compton et al., (2010) "Electrically Conductive 'Alkylated' Graphene Paper via Chemical Reduction of Amine-Functionalized Graphene Oxide Paper" Adv. Mater., vol. 22, pp. 892-896.
Cook et al., (2010) "Solar Energy Supply and Storage for the Legacy and Nonlegacy Worlds" Chem. Rev., vol. 110, pp. 64746502.
Costentin et al., (2012) "Turnover Numbers, Turnover Frequencies, and Overpotential in Molecular Catalysis of Electrochemical Reactions. Cyclic Voltammetry and Preparative-Scale Electrolysis" J. Am. Chem. Soc., vol. 134, pp. 11235-11242.
Cowley et al., (2002) "An Unusual Dimeric Structure of a Cu(I) Bis(thiosemicarbazone) Complex: Implications for the Mechanism of Hypoxic Selectivity of the Cu(II) Derivatives" J. Am. Chem. Soc., vol. 124, pp. 5270-5271.
Cowley et al., (2006) "Copper Complexes of Thiosemicarbazone-Pyridylhydrazine (THYNIC) Hybrid Ligands: A New Versatile Potential Bifunctional Chelator for Copper Radiopharmaceuticals" Inorganic Chemistry, vol. 45, No. 2, pp. 496-498.
Cowley et al., (2007) "Bifunctional chelators for copper radiopharmaceuticals: the synthesis of [Cu(ATSM)-amino acid] and [Cu(ATSM)-octreotide] conjugates" Dalton Trans., pp. 209-217.
Cracknell et al., (2008) "Enzymes as working or inspirational electrocatalysts for fuel cells and electrolysis" Chem. Rev., vol. 108, pp. 2439-2461.
Darensbourg et al., (2003) "The organometallic active site of Fe hydrogenase: Models and entatic states" Proc. Natl. Acad. Sci. USA, vol. 100, pp. 3683-3688.

(56) References Cited

OTHER PUBLICATIONS

Darmon et al., (2014) "Iron Complexes for the Electrocatalytic Oxidation of Hydrogen: Tuning Primary and Secondary Coordination Spheres" ACS Catalysis, vol. 4, pp. 1246-1260.
Das et al., (2015) "Nickel Complexes for Robust Light-Driven and Electrocatalytic Hydrogen Production from Water" ACS Catal., vol. 5, pp. 1397-1406.
Dubois et al., (2009) "Development of Molecular Electrocatalysts for CO2 Reduction and H2 Production/Oxidation" Acc. Chem. Res., vol. 42, No. 12, 1974-1982.
Fontecilla-Camps et al., (2007) "Structure/function relationships of NiFe- and FeFe-hydrogenases" Chem. Rev., vol. 107, pp. 4273-4303.
Foster et al., (2000) "Bis[N,N'-bis(2,4,6-trimethylphenyl)-1,2-ethanediylidenediamine]copper(I) tetrafluoroborate" Acta Crystallogr. Sect. C: Cryst. Struct. Commun., vol. C56, pp. 319-320 (plus suppoorting information). (9 pages).
Fourmond et al., (2010) "H2 Evolution and Molecular Electrocatalysts: Determination of Overpotentials and Effect of Homoconjugation" Inorganic Chemistry, vol. 49, pp. 10338-10347.
Gallucci (1982) "Reactions of Substituted Hydrazines with Glyoxal" J. Chem. Eng. Data, vol. 27, pp. 217-219.
Gardiner et al., (1994) "Paramagnetic Bis(1,4-di-tert-butyl-1,4-diazabutadiene) Adducts of Lithium, Magnesium, and Zinc" Inorg. Chem., vol. 33, pp. 2456-2461.
Ghaffarinejad et al, (2013) "Hydrogen Generation by Shimalite Ni Catalyst" Anal. Bioanal. Electrochem., vol. 5, No. 3, pp. 316-324.
Ghiamaty (2016) "Synthesis of palladium-carbon nanotube-metal organic framework composite and its application as electrocatalyst for hydrogen production" Journal of Nanostructure in Chemistry, vol. 6, pp. 299-308.
Goff et al., (2010) "Facile and tunable functionalization of carbon nanotube electrodes with ferrocene by covalent coupling and π-stacking interactions and their relevance to glucose bio-sensing" J. Electroanal. Chem., vol. 641, pp. 57-63.
Grass (1997) "Electrochemical generation of rhodium porphyrin hydrides. Catalysis of hydrogen evolution" J. Am. Chem. Soc., vol. 119, pp. 7526-7532.
Gray, (2009) "Powering the Planet with Solar Fuel" Nat. Chem., vol. 1, p. 7.
Haddad et al., (2015) "Proposed Ligand-Centered Electrocatalytic Hydrogen Evolution and Hydrogen Oxidation at a Noninnocent Mononuclear Metal-Thiolate" J. Am. Chem. Soc., vol. 137, pp. 9238-9241.
Haddad, (2017) Ph.D Thesis "Homogeneous Ligand-Centered Hydrogen Evolution And Hydrogen Oxidation: Exploiting Redox Non-Innocence to Drive Catalysis" (266 pages).
Haddleton et al., (1998) "Copper diimine complexes: the synthesis and crystal structures of [Cu(C10H14N2)2(MeOH)] [BF4], [Cu(C10H20N2)2]Br, [{(C10H14N2)CuBr(□-OMe)}2(MeOH)] and [{(C10H20N2)CuBr(□-OMe)}2]" J. Chem. Soc., Dalton Trans., pp. 381-385.
Halbert et al., (1985) "Electrocatalytic and Analytical Response of Cobalt Phthalocyanine Containing Carbon Paste Electrodes toward Sulfhydryl Compounds" Anal. Chem., vol. 57, pp. 591-595.
Harnisch et al., (2009) "Tungsten carbide as electrocatalyst for the hydrogen evolution reaction in pH neutral electrolyte solutions" Appl Catal B-Environ, vol. 89, pp. 455-458.
Hess et al., (2010) "Influence of the Redox Active Ligand on the Reactivity and Electronic Structure of a Series of Fe (TIM) Complexes" Inorg. Chem., vol. 49, pp. 5686-5700.
Heyduk et al., (2011) "Designing Catalysts for Nitrene Transfer Using Early Transition Metals and Redox-Active Ligands" Inorg. Chem., vol. 50, pp. 9849-9863.
Hinnemann (2005) "Biomimetic hydrogen evolution: MoS2 nanoparticles as catalyst for hydrogen evolution" J. Am. Chem. Soc., vol. 127, pp. 5308-5309.
Holland et al., (2007) "Functionalized Bis(thiosemicarbazonato) Complexes of Zinc and Copper: Synthetic Platforms Toward Site-Specific Radiopharmaceuticals" Inorg. Chem., vol. 46, 465-485.

Holzinger et al., (2012) "Carbon nanotube/enzyme biofuel cells" Electrochim. Acta, vol. 82, pp. 179-190.
Hu et al., (2007) "Electrocatalytic hydrogen evolution at low overpotentials by cobalt macrocyclic glyoxime and tetraimine complexes" J. Am. Chem. Soc., vol. 129, pp. 8988-8998.
Hueting et al., (2010) "Bis(thiosemicarbazones) as bifunctional chelators for the room temperature 64-copper labeling of peptides" Dalton Transactions, vol. 39, pp. 3620-3632.
Ibrahim et al., (2007) "Electropolymeric materials incorporating subsite structures related to iron-only hydrogenase: active ester functionalised poly(pyrroles) for covalent binding of {2Fe3S}-carbonyl/cyanide assemblies" Chem. Commun., pp. 1535-1537.
Jaegermann et al., (1988) "Interfacial properties of semiconducting transition metal chalcogenides" Prog. Surf. Sci., vol. 29, pp. 1-167.
Jain et al., (2016) "Copper catalysed aerobic oxidation of benzylic alcohols in an imidazole containing N4 ligand framework" Dalton Trans., vol. 45, pp. 18356-18364.
Jaramillo et al., (2007) "Identification of active edge sites for electrochemical H-2 evolution from MoS2 nanocatalysts" Science, vol. 317, pp. 100-102.
Jiang (2014) "A Cost-Effective 3D Hydrogen Evolution Cathode with High Catalytic Activity: FeP Nanowire Array as the Active Phase" Angew. Chem. Int. Ed., vol. 53, pp. 12855-12859.
Jing et al., (2015) "Light-driven hydrogen evolution with a nickel thiosemicarbazone redox catalyst featuring Ni H interactions under basic conditions" New Journal of Chemistry, vol. 39, pp. 1051-1059.
Jones et al., (1970) "Complexes of Transition Metals with Schiff Bases and the Factors Influencing their Redox Properties. Part I. Nickel and Copper Complexes of Some Diketone Bisthiosemicarbazones" J. Chem. Soc. A, pp. 2829-2836.
Jouad et al., (2005) "Structural and spectral studies of nickel(II), copper(II) and cadmium(II) complexes of 3-furaldehyde thiosemicarbazone" Polyhedron, vol. 24, pp. 327-332.
Kaeffer et al., (2015) "Hydrogen Evolution Catalyzed by Cobalt Diimine Dioxime Complexes" Acc. Chem. Res., vol. 48, No. 5, pp. 1286-1295.
Kaeffer et al., (2016) "The Dark Side of Molecular Catalysis: Diimine-Dioxime Cobalt Complexes Are Not the Actual Hydrogen Evolution Electrocatalyst in Acidic Aqueous Solutions" ACS Catal. vol. 6, pp. 3727-3737.
Karnin et al., (1980) "Rotating-Ring-Disk Enzyme Electrode for Biocatalysis Kinetic-Studies and Characterization of the Immobilized Enzyme Layer" Anal. Chem., vol. 52, pp. 1198-1205.
Kellett et al., (1985) "Cobalt porphyrin electrode films as hydrogen catalysts" Inorg. Chem., vol. 24, pp. 2378-2382.
Koca et al., (2009) "Voltammetric, in-situ spectroelectrochemical and in-situ electrocoIorimetric characterization of phthalocyanines" Electrochimica Acta, vol. 54, pp. 2684-2692.
Koca et al., (2010) "Electrochemical, In Situ Spectroelectrochemical, In Situ ElectrocoIorimetric and Electrocatalytic Characterization of Metallophthalocyanines Bearing Four Dioctylaminocarbonyl Biphenyloxy Substituents" Electroanalysis, vol. 22, No. 3, pp. 310-319.
Koca et al., (2011) "Electrocatalytic oxygen reduction and hydrogen evolution reactions on phthalocyanine modified electrodes: Electrochemical, in situ spectroelectrochemical, and in situ electrocoIorimetric monitoring" Electrochim. Acta, vol. 56, pp. 5513-5525.
Koca, (2009) "Copper phthalocyanine complex as electrocatalyst for hydrogen evolution reaction" Electrochem. Commun., vol. 11, pp. 838-841.
Koca, (2009) "Hydrogen evolution reaction on glassy carbon electrode modified with titanyl phthalocyanines" Int. J. Hydrogen Energy, vol. 34, pp. 2107-2112.
Kotani et al., (2011) "Size- and Shape-Dependent Activity of Metal Nanoparticles as Hydrogen-Evolution Catalysts: Mechanistic Insights into Photocatalytic Hydrogen Evolution" Chemistry—A European Journal, vol. 17, pp. 2777-2785.
Lalaoui et al., (2016) "Direct Electron Transfer between a Site-Specific Pyrene-Modified Laccase and Carbon Nanotube/Gold Nanoparticle Supramolecular Assemblies for Bioelectrocatalytic Dioxygen Reduction" ACS Catal., vol. 6, pp. 1894-1900.

(56) References Cited

OTHER PUBLICATIONS

Lalaoui et al., (2016) "Diazonium Functionalisation of Carbon Nanotubes for Specific Orientation of Multicopper Oxidases: Controlling Electron Entry Points and Oxygen Diffusion to the Enzyme" Chem.-Eur. J., vol. 22, pp. 10494-10500.

Laursen et al., (2013) "A high-porosity carbon molybdenum sulphide composite with enhanced electrochemical hydrogen evolution and stability" Chem. Commun., vol. 49, pp. 4965-4967.

Lawrence et al., (2015) "Electrochemical-Frustrated Lewis Pair Approach to Hydrogen Activation: Surface Catalytic Effects at Platinum Electrodes" Chem. Eur. J., vol. 21, pp. 900-906.

Le Gac et al., (2006) "Efficient synthesis and host-guest properties of a new class of calix[6]azacryptands" J. Org. Chem., vol. 71, pp. 9233-9236.

Le Goff et al., (2009) "From Hydrogenases to Noble Metal-Free Catalytic Nanomaterials for H-2 Production and Uptake" Science, vol. 326, pp. 1384-1387.

Lee at al., (2017) "Identification of an Electrode-Adsorbed Intermediate in the Catalytic Hydrogen Evolution Mechanism of a Cobalt Dithiolene Complex" Inorg. Chem., vol. 56, pp. 1988-1998.

Lei et al., (2014) "Electrochemical, spectroscopic and theoretical studies of a simple bifunctional cobalt corrole catalyst for oxygen evolution and hydrogen production" PCCP, vol. 16, pp. 1883-1893.

Lei et al., (2016)"Noncovalent Immobilization of a Pyrene-Modified Cobalt Corrole on Carbon Supports for Enhanced Electrocatalytic Oxygen Reduction and Oxygen Evolution in Aqueous Solutions" ACS Catal., vol. 6, pp. 6429-6437.

Lewis et al., (2006) "Powering the planet: Chemical challenges in solar energy utilization" Proc. Natl. Acad. Sci. USA, vol. 103, pp. 15729-15735.

Li et al., (2011) "MoS2 Nanoparticles Grown on Graphene: An Advanced Catalyst for the Hydrogen Evolution Reaction" J. Am. Chem. Soc., vol. 133, pp. 7296-7299.

López-Torres et al., (2009) "Reactivity of Thiosemicarbazides with Redox Active Metal Ions: Controlled Formation of Coordination Complexes versus Heterocyclic Compounds" Chem. Eur. J., vol. 15, pp. 3012-3023.

Löw et al., (2013) "Reactions of Copper(II) Chloride in Solution: Facile Formation of Tetranuclear Copper Clusters and Other Complexes That Are Relevant in Catalytic Redox Processes" Chem. Eur. J., vol. 19, pp. 5342-5351.

Venkatraman et al. (2015) "bis(N-Phenyl-N'-(1-(1,3-thiazol-2-yl)ethylidene)carbamohydrazonothioato)-zinc N,N-dimethylformamide solvate" Deposit No. 1059843, deposit date Apr. 15, 2015. (1 page).

Vijaikanth et al., (2005) "Chemically modified electrode based on an organometallic model of the [FeFe] hydrogenase active center" Electrochem. Commun., vol. 7, pp. 427-430.

Vijayan et al., (2016) "Toward a new avenue in ruthenium-sulphur chemistry of binuclear[mu]-sulphido bridged ([mu]-S)2complexes having Ru2S2core: Targeted synthesis, crystal structure, biomolecules interaction and thier in vitro anticancer activities" Inorganica Chimica Acta, vol. 453, pp. 596-617.

Viñuelas-Zahínos et al., (2011)"Co(III), Ni(II), Zn(II) and Cd(II) complexes with 2-acetyl-2-thiazoline thiosemicarbazone: Synthesis, characterization, X-ray structures and antibacterial activity" Eur. J. Med. Chem., vol. 46, pp. 150-159.

Voiry et al., (2013) "Enhanced catalytic activity in strained chemically exfoliated WS2 nanosheets for hydrogen evolution" Nat Mater, vol. 12, pp. 850-855.

Vuilleumier et al., (2012) "Hopping along hydrogen bonds" Nature Chemistry, vol. 4, pp. 432-433.

Walgama et al., (2014) "Tuning the Electrocatalytic Efficiency of Heme-Protein Films by Controlled Immobilization on Pyrene-Functionalized Nanostructure Electrodes" J. Electrochem. Soc., vol. 161, No. 1, pp. H47-H52.

Wan et al., (2014) "Multiple Phases of Molybdenum Carbide as Electrocatalysts for the Hydrogen Evolution Reaction" Angew. Chem. 2014, vol. 126, pp. 6525-6528.

Wang et al., (2009) "Synthesis, characterization and spectra studies on Zn(II) and Cu(II) complexes with thiocarbamide ligand containing Schiff base group" Struct. Chem., vol. 20, pp. 995-1003.

West et al., (1993) "Thiosemicarbazone complexes of copper(II): structural and biological studies" Coordination Chemistry Reviews, vol. 123, pp. 49-71.

Wiese et al., (2012) "[Ni(PMe2NPh2)2](BF4)2 as an Electrocatalyst for H2 Production" ACS Catal., vol. 2, pp. 720-727.

Willner et al., (2009) "Integrated Enzyme-Based Biofuel Cells—A Review" Fuel Cells, vol. 9, No. 1, pp. 7-24.

Wilson et al., (2006) "Hydrogen Oxidation and Production Using Nickel-Based Molecular Catalysts with Positioned Proton Relays" Journal of the American Chemical Society, vol. 128, pp. 358-366.

Winkelmann et al., (1977) "Anticoccidial activity of dithiosemicarbazones", Arzneimittel Forschung. Drug Research, vol. 27, No. 5, pp. 950-967.

Yaghi et al., (1995) "Hydrothermal Synthesis of a Metal-Organic Framework Containing Large Rectangular Channels" J. Am. Chem. Soc., vol. 117, pp. 10401-10402.

Yan et al., (2014) "Recent Development of Molybdenum Sulfides as Advanced Electrocatalysts for Hydrogen Evolution Reaction" ACS Catal., vol. 4, pp. 1693-1705.

Yang et al., (2010) "Hydrogen oxidation catalysis by a nickel diphosphine complex with pendant tert-butyl amines" Chemical Communications, vol. 46, pp. 8618-8620.

Zarkadoulas et al., (2012) "A perspective on solar energy conversion and water photosplitting by dithiolene complexes" Coord. Chem. Rev., vol. 256, pp. 2424-2434.

Zarkadoulas et al., (2016) "Experimental and Theoretical Insight into Electrocatalytic Hydrogen Evolution with Nickel Bis(aryldithiolene) Complexes as Catalysts" Inorg. Chem., vol. 55, pp. 432-444.

Zhang et al., (2016) "Reversible Methanol Addition to Copper Schiff Base Complexes: A Kinetic, Structural, and Spectroscopic Study of Reactions at Azomethine C=N Bonds" Dalton Trans., vol. 45, No. 40., pp. 15791-15799.

Zhang et al., (2017) "Translation of Ligand-Centered HER Activity and Mechanism of a Rhenium-Thiolate from Solution to Modified Electrodes: A Combined Experimental and Density Functional Theory Study." Dalton Trans., vol. 56, pp. 2177-2187.

Zhao et al., (1999) "Electrocatalytic proton reduction by phthalocyanine cobalt derivatives incorporated in poly(4-vinylpyridine-co-styrene) film" J. Mol. Catal. A: Chem., vol. 145, pp. 245-256.

Zhao et al., (2008) "In situ hydrothermal synthesis of tetrazole coordination polymers with interesting physical properties" Chem. Soc. Rev., vol. 37, pp. 84-100.

Zhao et al., (2010) "Synthesis, structures, and property studies on Zn(II), Ni(II), and Cu(II) complexes with a Schiff base ligand containing thiocarbamide group" Struct. Chem., vol. 21, pp. 977-987.

Zheng et al., (2014) "Hydrogen Evolution by a Metal-Free Electrocatalyst" Nat. Commun., vol. 5, Article 3783. (8 pages).

U.S. Appl. No. 16/214,088 nonfinal Office action dated Nov. 25, 2020 (37 pages).

U.S. Appl. No. 16/214,088 Interview Summary dated Feb. 22, 2021 (17 pages).

U.S. Appl. No. 16/214,088 Response to nonfinal Office action dated Mar. 24, 2021 (21 pages).

Marinescu et al. (2012) "Molecular Mechanisms of Cobalt-Catalyzed Hydrogen Evolution" Proc. Natl. Acad. Sci. USA, vol. 109, pp. 15127-15131.

Maroney et al., (1984) "Coordination chemistry of copper macrocyclic complexes: synthesis and characterization of copper complexes of TIM" Inorg. Chem., vol. 23, pp. 2252-2261.

McCrory et al., (2015) "Benchmarking Hydrogen Evolving Reaction and Oxygen Evolving Reaction Electrocatalysts for Solar Water Splitting Devices" J. Am. Chem. Soc., vol. 137, pp. 4347-4357.

McKone et al., (2014) "Earth-abundant hydrogen evolution electrocatalysts" Chemical Science, vol. 5, pp. 865-878.

McNamara et al., (2011) "A Cobalt-Dithiolene Complex for the Photocatalytic and Electrocatalytic Reduction of Protons" J. Am. Chem. Soc., vol. 133, pp. 15368-15371.

(56) References Cited

OTHER PUBLICATIONS

McNamara et al., (2012) "Cobalt-dithiolene complexes for the photocatalytic and electrocatalytic reduction of protons in aqueous solutions" Proc. Natl. Acad. Sci. USA, vol. 109, No. 39, pp. 15594-15599.
McQueen et al., (2009) "Electrochemical Analysis of Single-Walled Carbon Nanotubes Functionalized with Pyrene-Pendant Transition Metal Complexes" J. Am. Chem. Soc., vol. 131, pp. 17554-17556.
Merki et al., (2011) "Amorphous molybdenum sulfide films as catalysts for electrochemical hydrogen production in water" Chem Sci, vol. 2, pp. 1262-1267.
Merki et al., (2012) "Fe, Co, and Ni ions promote the catalytic activity of amorphous molybdenum sulfide films for hydrogen evolution" Chem Sci, vol. 3, pp. 2515-2525.
Mondal et al., (2013) "Cobalt Corrole Catalyst for Efficient Hydrogen Evolution Reaction from H2O under Ambient Conditions: Reactivity, Spectroscopy, and Density Functional Theory Calculations" Inorganic Chemistry, vol. 52, pp. 3381-3387.
Navaee et al., (2015) "Efficient amine functionalization of graphene oxide through the Bucherer reaction: an extraordinary metal-free electrocatalyst for the oxygen reduction reaction" RSC Adv., vol. 5, pp. 59874-59880.
Osmanbaş et al., (2008) "Electrocatalytic activity of phthalocyanines bearing thiophenes for hydrogen production from water" Int. J. Hydrogen Energy, vol. 33, pp. 3281-3288.
Pantani et al., (2007) "Electroactivity of cobalt and nickel glyoximes with regard to the electro-reduction of protons into molecular hydrogen in acidic media" Electrochem. Commun., vol. 9, pp. 54-58.
Park et al., (2006) "Hydrothermal Synthesis and Structural Characterization of Novel Zn-Triazole-Benzenedicarboxylate Frameworks" Chem. Mater., vol. 18, pp. 525-531.
Popczun et al., (2013) "Nanostructured Nickel Phosphide as an Electrocatalyst for the Hydrogen Evolution Reaction" J. Am. Chem. Soc., vol. 135, pp. 9267-9270.
Popczun et al., (2014) "Highly Active Electrocatalysis of the Hydrogen Evolution Reaction by Cobalt Phosphide Nanoparticles" Angew. Chem. Int. Ed., vol. 53, pp. 5427-5430.
Reath et al., (2017) "Redox Potential and Electronic Structure Effects of Proximal Nonredox Active Cations in Cobalt Schiff Base Complexes" Inorg. Chem., vol. 56, p. 3713-3718.
Remita et al., (2006) "Activity evaluation of carbon paste electrodes loaded with pt nanoparticles prepared in different radiolytic conditions" J. Solid State Electrochem., vol. 10, pp. 506-511.
Rijnberg et al., (1998) "A Homologous Series of Homoleptic Zinc Bis(1,4-di-tert-butyl-1,4-diaza-1,3-butadiene) Complexes: K-[Zn(t-BuNCHCHN-t-Bu)2], Zn(t-BuNCHCHN-t-Bu)2, and [Zn(t-BuNCHCHN-t-Bu)2](OTf)x (x=1,2)" Inorg. Chem., vol. 37, pp. 56-63.
Ringenberg et al., (2008) "Redox-switched oxidation of dihydrogen using a non-innocent ligand" J. Am. Chem. Soc., vol. 130, pp. 788-789.
Ringenberg et al., (2010) "Oxidation of Dihydrogen by Iridium Complexes of Redox-Active Ligands" Organometallics, vol. 29, pp. 1956-1965.
Rosenkoetter et al., (2016) "A Heterobimetallic W—Ni Complex Containing a Redox-Active W[SNS](2) Metalloligand" Inorg. Chem., vol. 55, pp. 6794-6798.
Rufenacht, (1972) "120. Arbeiten über phosphorsäure- und thiophosphorsauereester mit einem heterocyclischen substituenten. Thiadiazol-ringschluss und eine dabei aufretende methylübertragung." Helv. Chim. Acta, vol. 55, pp. 1178-1187.
Saha et al., (2002) "Synthesis and structural characterisation of new iron(III) complexes with biologically relevant pyrazolyl thiosemicarbazones" Inorg. Chim. Acta, vol. 339, pp. 348-354.
Saha et al., (2003) "Synthesis and spectroscopic identification of new iron(III) complexes with 5-methyl-3-formylpyrazole-3-piperidinylthiosemicarbazone (HMPz3Pi): X-ray structure of [Fe(MPz3Pi)2]ClO4-2H2O" Polyhedron, vol. 22, pp. 375-381.

Saha et al., (2003) "Synthesis and spectroscopic characterisation of cobalt(III) and nickel(II) complexes with 5-methyl-3-formylpyrazole-N(4)-dibutylthiosemicarbazone (HMPzNBu2): X-ray crystallography of [Co(MPzNBu2)2] NO3—H2O (I) and [Ni(HMPzNBu2)2](ClO4)2 (II)" Polyhedron, vol. 22, pp. 383-390.
Saha et al., (2005) "Synthesis, spectroscopy and cyclic voltammetry of new iron(III) complexes with 5-methyl-3-formyl pyrazole 3-hexamethyleneiminyl thiosemicarbazone (HMPz3Hex): X-ray crystallographic identification of [Fe(MPz3Hex)2]ClO4—2H2O with an indication for unusual rotation about the azomethine double bond on complexation with iron(III)" Transition Met. Chem., vol. 30, pp. 532-540.
Sau et al., (2004) "Synthesis and spectroscopic characterization of new cobalt(III) complexes with 5-methyl-3-formyl pyrazole 3-hexamethyleneiminyl thiosemicarbazone (HMPz3Hex): X-ray crystallographic identification of HMPz3Hex and [Co(MPz3Hex)2]Br—H2O with evidence for unusual rotation about the azomethine double bond of the ligand on complexation with cobalt(III)" Polyhedron, vol. 23, pp. 5-14.
Saveant et al., (1984) "Homogeneous Redox Catalysis of Electrochemical Reaction, Part VI. Zone Diagram Representation of the Kinetic Regimes" Journal of Electroanalytical Chemistry, vol. 171, pp. 341-349.
Shima et al., (2008) "The crystal structure of Fe-hydrogenase reveals the geometry of the active site" Science, vol. 321, pp. 572-575.
Shu et al., (1976) "Rotating-Ring-Disk Enzyme Electrode for Surface Catalysis Studies" Anal. Chem., vol. 48, No. 12, pp. 1679-1686.
Smith et al., (2012) "Reversible Electrocatalytic Production and Oxidation of Hydrogen at Low Overpotentials by a Functional Hydrogenase Mimic" Angew. Chem. Int. Ed., vol. 51, pp. 3152-3155.
Solis et al., (2016) "Nickel phlorin intermediate formed by proton-coupled electron transfer in hydrogen evolution mechanism" Proc. Natl. Acad. Sci. USA, vol. 113, pp. 485-492.
Sosna et al., (2010) "Monolayer anthracene and anthraquinone modified electrodes as platforms for Trametes hirsuta laccase immobilisation" Phys. Chem. Chem. Phys., vol. 12, pp. 10018-10026.
Sun et al., (2010) "Synthesis, Crystal Structures and Fluorescence Properties of Ni (II) and Cu (II) Complexes with 1-(Furan-2-ylmethylene)-4-phenylthiosemicarbazone" J. Chem. Crystallogr., vol. 40, pp. 4-9.
Tan et al., (2009), K. W.; Ng, C. H.; Maah, M. J.; Ng, S. W. "Bis(acetone 4-phenylthiosemicarbazonato-kappa2N1,S) zinc(II)" Acta Crystallogr. Sect. Sect. E: Struct. Rep. Online, vol. E65, m969 plus supplementary materials. (7 pages).
Thompson et al., (2015) "Electrocatalytic Hydrogen Production by an Aluminum(III) Complex: Ligand-Based Proton and Electron Transfer" Angewandte Chemie, vol. 127, pp. 11808-11812.
Thorn et al., (2008) "Structures of [(n-C4H9)2NH2]2Cd9Cl2O—2H2O and [Cu(C14H24N4)]2Cu13Cl30(H2O)2-xH2O: Perforated Layer Structures Based on the CdCl2 Layer Network" Inorg. Chem., vol. 47, No. 13, pp. 5775-5779.
Todd et al., (1998) "Electrochemically induced metalation of polymeric phthalocyanines" J. Am. Chem. Soc., vol. 120, pp. 4887-4888.
Tran et al., (2011) "Noncovalent Modification of Carbon Nanotubes with Pyrene-Functionalized Nickel Complexes: Carbon Monoxide Tolerant Catalysts for Hydrogen Evolution and Uptake" Angew. Chem. Int. Ed., vol. 50, pp. 1371-1374.
Tributsch et al., (1977) "Electrochemistry and photochemistry of MoS2 layer crystals. I" Journal of Electroanalytical Chemistry, vol. 81, pp. 97-111.
Turner, (2004) "Sustainable hydrogen production" Science, vol. 305, pp. 972-974.

Anti-Proliferative Activity Assay – I-3

Anti-Proliferative Activity Assay – I-6

Anti-Proliferative Activity Assay – I-8

Anti-Proliferative Activity Assay – I-9

Anti-Proliferative Activity Assay – I-11

Anti-Proliferative Activity Assay – I-12

Anti-Proliferative Activity Assay – I-12

Anti-Proliferative Activity Assay – I-14

Compound I-1 (NV3104)

COMPOUNDS, COMPOSITIONS, METHODS FOR TREATING DISEASES, AND METHODS FOR PREPARING COMPOUNDS

CROSS-REFERENCE TO RELATED APPLICATIONS

This application is a continuation in part of PCT/US2018/030765, filed May 3, 2018 entitled "THIOSEMICARBAZONE DERIVATIVES AS ANTI-CANCER AGENTS" which is herein incorporated by reference in its entirety, which claims the benefit of U.S. Provisional Application No. 62/501,553, filed May 4, 2017 entitled "THERAPEUTIC APPLICATIONS OF VARIOUS METAL N2S2 COMPOUNDS" which is herein incorporated by reference in its entirety. This application also claims the benefit of U.S. Provisional Application No. 62/768,921, filed Nov. 18, 2018 entitled "SYNTHESIS, CHARACTERIZATION, AND EVALUATION OF METAL COMPLEXES FOR SELECTIVE TARGETING AND ANTI-PROLIFERATIVE EFFECT ON CANCER CELLS AND THEIR HYDROGEN EVOLUTION CATALYTIC PROPERTIES" which is herein incorporated by reference in its entirety.

GOVERNMENT RIGHTS

This invention was made with government support under CHE-1361728 awarded by National Science Foundation. The government has certain rights in the invention.

BACKGROUND

Several compounds are known to treat diseases, such as cancer, but do so inadequately. For example, some platinum-containing drugs can be effective anticancer therapies, but they can sometimes have side effects, such as toxicity. Attempts to design compounds (e.g., compounds containing metals) have not yielded effective anticancer agents and are not always as less toxic to non-cancer cells as would be desired.

Certain embodiments of the invention address one or more of the deficiencies described above. Some embodiments of the invention include inventive compounds (e.g., compounds of Formula (I) or (Ia)). Other embodiments include compositions (e.g., pharmaceutical compositions) comprising the inventive compound. Still other embodiments of the invention include compositions (e.g., pharmaceutical compositions) for treating, for example, certain diseases using the inventive compounds. Some embodiments include methods of using the inventive compound (e.g., in compositions or in pharmaceutical compositions) for administering and treating (e.g., diseases such as cancer). Further embodiments include methods for making the inventive compounds. Additional embodiments of the invention are also discussed herein.

SUMMARY

Some embodiments of the present invention include a compound selected from
(a) Formula (Ia)

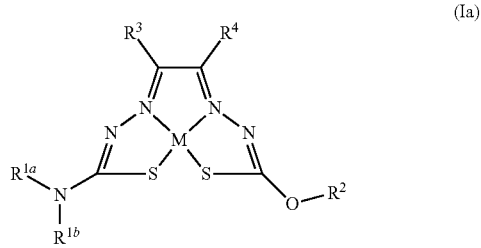

and salts, optical isomers, geometric isomers, salts of isomers, and derivatives thereof; and
(b) Formula (Ib)

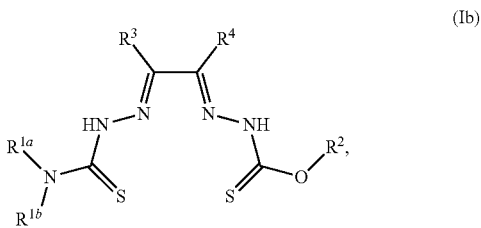

and salts, optical isomers, geometric isomers, salts of isomers, and derivatives thereof. In some embodiments, $R^{1a}$ is H, halogen, —CN, hydroxy (—OH), methanoyl (—COH), carboxy (—CO$_2$H), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl, which methanoyl (—COH), carboxy (—CO$_2$H), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, —CF$_3$, —OCF$_3$, or $C_1$-$C_3$ alkoxy. In other embodiments, $R^{1b}$ is H, halogen, —CN, hydroxy (—OH), methanoyl (—COH), carboxy (—CO$_2$H), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl, which methanoyl (—COH), carboxy (—CO$_2$H), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, —CF$_3$, —OCF$_3$, or $C_1$-$C_3$ alkoxy. In yet other embodiments, $R^{1a}$ and $R^{1b}$ are optionally bonded together with their attached nitrogen to form heterocyclyl or heteroaryl, which heterocyclyl or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy. In certain embodiments, R$^2$ is H, halogen, —CN, hydroxy (—OH), methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl, which methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy. In some embodiments, R$^3$ is H, halogen, —CN, hydroxy (—OH), methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl, which methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy. In other embodiments, R$^4$ is H, halogen, —CN, hydroxy (—OH), methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl, which methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy. In some embodiments, R$^3$ and R$^4$ are optionally bonded together to form a ring with their attached carbons that is fused to the attached carbons of R$^3$ and R$^4$, where the ring that is fused is cycloalkyl, heterocyclyl, aryl, or heteroaryl, which cycloalkyl, heterocyclyl, aryl, or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy. In certain embodiments, M is a divalent cation.

In some embodiments, R$^{1a}$ is H, methyl, ethyl, C$_{1-5}$ alkyl, C$_3$ alkyl, n-propyl, isopropyl, ethoxy, methoxy, 5-hydroxy pyridyl, indolyl, 1,2,3,4-tetrahydroisoquinolyl, furyl, 1,2-methylenedioxyphenyl, 2,3-methylenedioxyphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl. In other embodiments, R$^{1a}$ is H, methyl, ethyl, n-propyl, or phenyl. In yet other embodiments, R$^{1a}$ is not H.

In some embodiments, R$^{1b}$ is H, Cl, hydroxy (—OH), methyl, ethyl, C$_{1-5}$ alkyl, C$_3$ alkyl, C$_4$ alkyl, —CN, ethynyl, —CONH$_2$, —CON(CH$_3$)$_2$, 2-(morpholinyl)ethoxy, —CO-morpholin-4-yl, ethoxy, methoxy, 5-hydroxy pyridyl, indolyl, 1,2,3,4-tetrahydroisoquinolyl, 1,2-methylenedioxyphenyl, 2,3-methylenedioxyphenyl, furyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl. In other embodiments, R$^{1b}$ is H, methyl, ethyl, n-propyl, or phenyl. In still other embodiments, R$^{1b}$ is not H.

In some embodiments, R$^2$ is methyl, ethyl, C$_3$ alkyl, n-propyl, isopropyl, ethoxy, methoxy, 5-hydroxy pyridyl, indolyl, 1,2,3,4-tetrahydroisoquinolyl, furyl, 1,2-methylenedioxyphenyl, 2,3-methylenedioxyphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl. In other embodiments, R$^2$ is methyl, ethyl, n-propyl, or phenyl.

In some embodiments, R$^3$ is H, Cl, hydroxy (—OH), methyl, ethyl, C$_{1-5}$ alkyl, C$_3$ alkyl, —CN, ethynyl, —CONH$_2$, —CON(CH$_3$)$_2$, 2-(morpholinyl)ethoxy, —CO-morpholin-4-yl, ethoxy, methoxy, 5-hydroxy pyridyl, indolyl, 1,2,3,4-tetrahydroisoquinolyl, 1,2-methylenedioxyphenyl, 2,3-methylenedioxyphenyl, furyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl. In other embodiments, $R^3$ is H, methyl, ethyl, n-propyl, or phenyl.

In some embodiments, $R^4$ is H, Cl, hydroxy (—OH), methyl, ethyl, $C_{1-5}$ alkyl, $C_3$ alkyl, —CN, ethynyl, —CONH$_2$, —CON(CH$_3$)$_2$, 2-(morpholinyl)ethoxy, —CO-morpholin-4-yl, ethoxy, methoxy, 5-hydroxy pyridyl, indolyl, 1,2,3,4-tetrahydroisoquinolyl, 1,2-methylenedioxyphenyl, 2,3-methylenedioxyphenyl, furyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl. In other embodiments, $R^4$ is H, methyl, ethyl, n-propyl, or phenyl.

In some embodiments, M is iron (Fe), nickel (Ni), palladium (Pd), cadmium (Cd), manganese (Mn), cobalt (Co), copper (Cu), or zinc (Zn). In other embodiments, M is Cu, Ni, or Zn. In still other embodiments, M is Cu.

In some embodiments, the compound of Formula (I) is I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-53, I-54, I-55, I-56, I-57, I-58, I-59, I-60, I-61, I-62, I-63, I-64, I-65, I-66, I-67, I-68, I-69, I-70, or I-71. In other embodiments, the compound of Formula (I) is I-1, I-3, I-4, I-5, I-7, I-8, I-9, I-11, I-12, or I-22. In still other embodiments, the compound of Formula (I) is I-1 or I-5. In yet other embodiments, (a) $R^{1a}$ is H, $R^{1b}$ is methyl, $R^2$ is ethyl, $R^3$ is methyl, $R^4$ is methyl, M is Cu, or combinations thereof; (b) $R^{1a}$ is methyl, $R^{1b}$ is H, $R^2$ is ethyl, $R^3$ is methyl, $R^4$ is methyl, M is Cu, or combinations thereof; (c) $R^{1a}$ is H, $R^{1b}$ is methyl, $R^2$ is ethyl, $R^3$ is methyl, $R^4$ is methyl, M is Zn, or combinations thereof; or (d) $R^{1a}$ is methyl, $R^{1b}$ is H, $R^2$ is ethyl, $R^3$ is methyl, $R^4$ is methyl, M is Zn, or combinations thereof. In still other embodiments, $R^{1a}$ is H or $R^{1b}$ is H, but both $R^{1a}$ and $R^{1b}$ are not H.

Some embodiments of the invention include a composition comprising a compound, as disclosed herein (e.g., Formula (I)). In certain embodiments, the amount of the compound is from about 0.0001% (by weight total composition) to about 99%. In other embodiments, the composition further comprises a formulary ingredient, an adjuvant, or a carrier.

Some embodiments of the invention include a pharmaceutical composition comprising a compound, as disclosed herein (e.g., Formula (I)). In some embodiments, the amount of the compound is from about 0.0001% (by weight total composition) to about 50%. In other embodiments, the pharmaceutical composition further comprises a formulary ingredient, an adjuvant, or a carrier.

Some embodiments of the invention include a method for providing an animal with a compound comprising one or more administrations of one or more compositions comprising a compound as disclosed herein (e.g., Formula (I)), wherein the compositions may be the same or different if there is more than one administration. In other embodiments, at least one of the one or more compositions further comprises a formulary ingredient. In still other embodiments, at least one of the one or more compositions comprises a composition (e.g., as disclosed herein) or a pharmaceutical composition (e.g., as disclosed herein). In certain embodiments, at least one of the one or more administrations comprises parenteral administration, a mucosal administration, intravenous administration, subcutaneous administration, topical administration, intradermal administration, oral administration, sublingual administration, intranasal administration, or intramuscular administration. In other embodiments, if there is more than one administration at least one composition used for at least one administration is different from the composition of at least one other administration. In still other embodiments, the compound of at least one of the one or more compositions is administered to the animal in an amount of from about 0.01 mg/kg animal body weight to about 15 mg/kg animal body weight. In yet other embodiments, the animal is a human, a rodent, or a primate.

Some embodiments of the invention include a method for treating an animal for a disease, comprising one or more administrations of one or more compositions comprising a compound as disclosed herein (e.g., Formula (I)), wherein the compositions may be the same or different if there is more than one administration. In some embodiments, at least one of the one or more compositions further comprises a formulary ingredient. In other embodiments, at least one of the one or more compositions comprises a composition (e.g., as disclosed herein) or a pharmaceutical composition (e.g., as disclosed herein). In yet other embodiments, at least one of the one or more administrations comprises parenteral administration, a mucosal administration, intravenous administration, subcutaneous administration, topical administration, intradermal administration, oral administration, sublingual administration, intranasal administration, or intramuscular administration. In still other embodiments, if there is more than one administration at least one composition used for at least one administration is different from the composition of at least one other administration. In certain embodiments, the compound of at least one of the one or more compositions is administered to the animal in an amount of from about 0.005 mg/kg animal body weight to about 50 mg/kg animal body weight. In other embodiments, the animal is a human, a rodent, or a primate. In some embodiments, the animal is in need of the treatment. In other embodiments, the method is for treating cancer. In still other embodiments, the method is for treating acute lymphoblastic leukemia, astrocytoma, basal cell carcinoma, bladder cancer, bone marrow cancer, breast cancer, chronic lymphocytic leukemia (CLL), CNS cancer, colon cancer, colorectal cancer, endometrial cancer, gastric cancer, glioblastoma, glioblastoma multiforme, glioma, gliosarcoma, hepatocellular carcinoma, kidney cancer, leukemia, liver cancer, lung cancer, lymphoma, melanoma, malignant nerve sheath tumors, medulloblastoma, meningioma, multiple myeloma, nasopharyngeal carcinoma, neuroblastoma, non-Hodgkin lymphoma, non-small cell lung cancer, oral cancer, ovarian cancer, pancreatic cancer, prostate cancer, rectal cancer, renal cancer, renal cell carcinoma, rhabdomyosarcoma, squamous cell carcinoma, stomach cancer, thyroid cancer, uterine cancer, cancers that can result in metastasis, cancers resulting from metastasis, or cancerous tumors thereof. In some embodiments, the method is for treating leukemia, lung cancer, non-small cell lung cancer, colorectal cancer, colon cancer, rectal cancer, CNS cancer, glioblastoma, glioblastoma multiforme, gliosarcoma, astrocytoma, melanoma, cutaneous malignant melanoma, melanoma tumorigenesis, ovarian cancer, kidney cancer, prostate cancer, breast cancer, or cancerous tumors thereof. In other embodiments, the method does not include treating leukemia. In yet other embodiments, the method is for treating lung cancer, non-small cell lung cancer, colorectal cancer, colon cancer, rectal cancer, CNS cancer, glioblastoma, glioblastoma multiforme, gliosarcoma, astrocytoma, melanoma, cutaneous malignant melanoma, melanoma tumorigenesis, ovarian cancer, kidney cancer, prostate cancer, breast cancer, or cancerous tumors thereof. In other embodiments, the method is for treating cancerous tumors.

Some embodiments of the invention include a method for preparing a compound disclosed herein (e.g., Formula (I)) comprising (a) reacting a compound of Formula (II) with a compound of Formula (III) to result in a mixture comprising a compound of Formula (IV) and (b) reacting a compound of Formula (IV) with a compound of Formula (V) to result in a mixture comprising a compound of Formula (Ib). In other embodiments, the method further comprises recovering a compound of Formula (Ib). In some embodiments, the method further comprises (c) reacting a compound of Formula (Ib) with a compound of Formula (VI) and (d) recovering a compound of Formula (Ia). In some embodiments, Formula (II) is

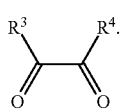
(II)

In other embodiments, Formula (III) is

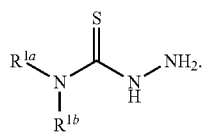
(III)

In other embodiments, Formula (IV) is

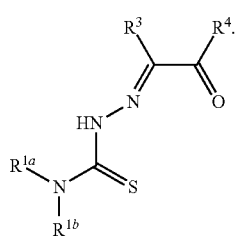
(IV)

In yet other embodiments, Formula (V) is

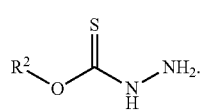
(V)

In still other embodiments, Formula (VI) is M:anion (VI). In some embodiments, the anion is a weak base, acetate, acetate monohydrate, acetate dihydrate, or acetate tetrahydrate. In other embodiments, the Formula (VI) is copper (II) acetate monohydrate, nickel (II) acetate tetrahydrate, or zinc (II) acetate dihydrate.

Other embodiments of the invention are also discussed herein.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

DETAILED DESCRIPTION

Figure 1:
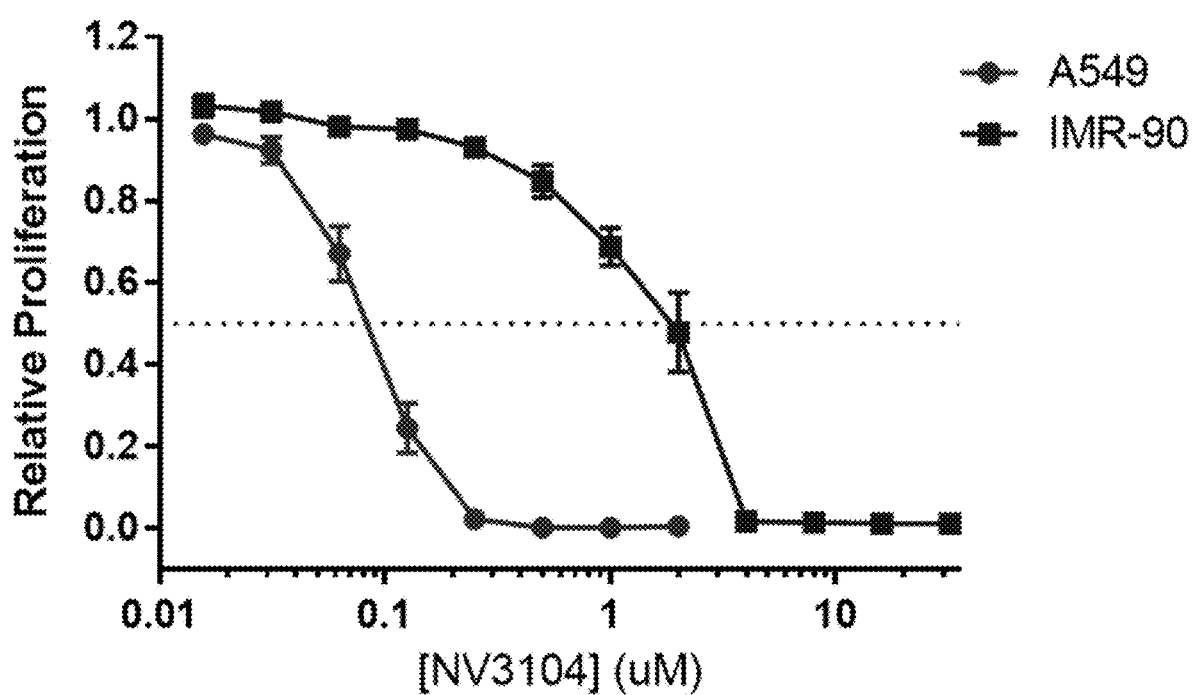
FIG. 1: Anti-proliferative activity of compound I-1 (NV3104) using MTT assay.
Figure 2:
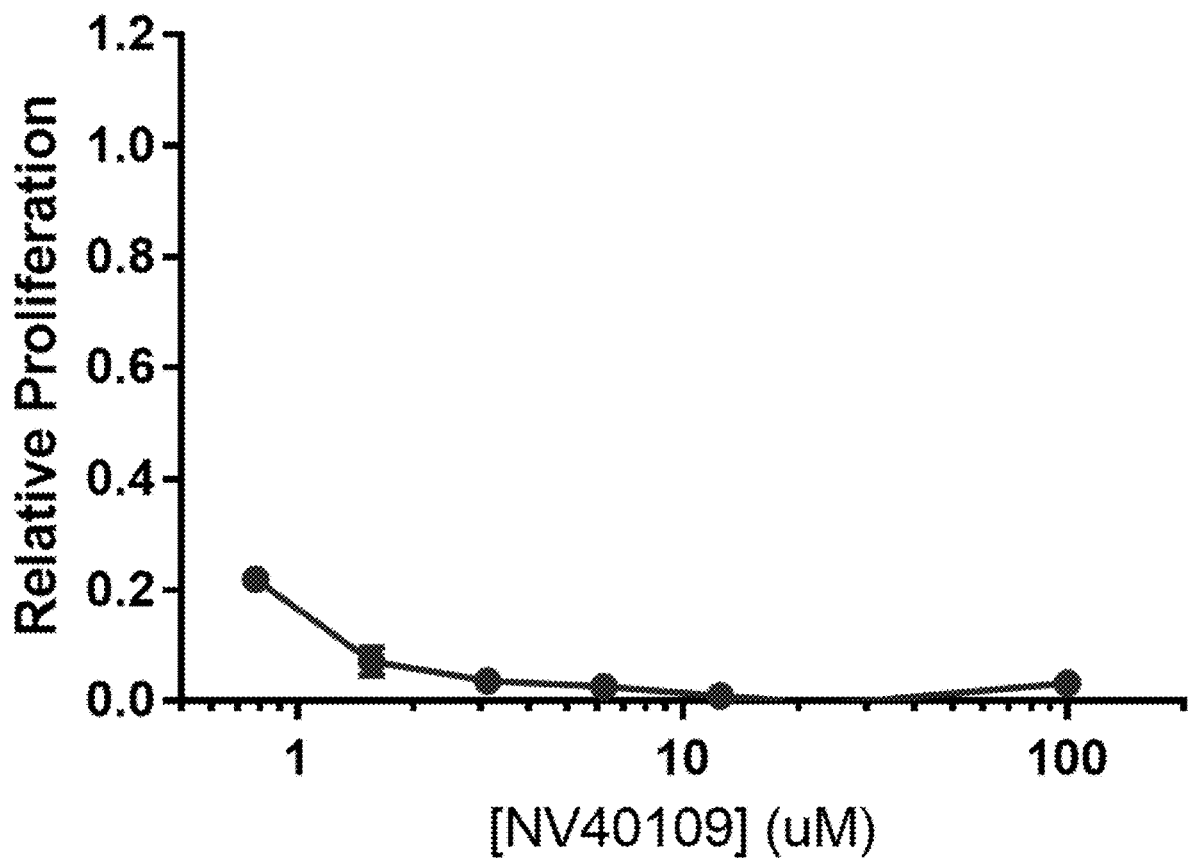
FIG. 2: Anti-proliferative activity of compound I-3 (NV40109) using MTT assay.
Figure 3:
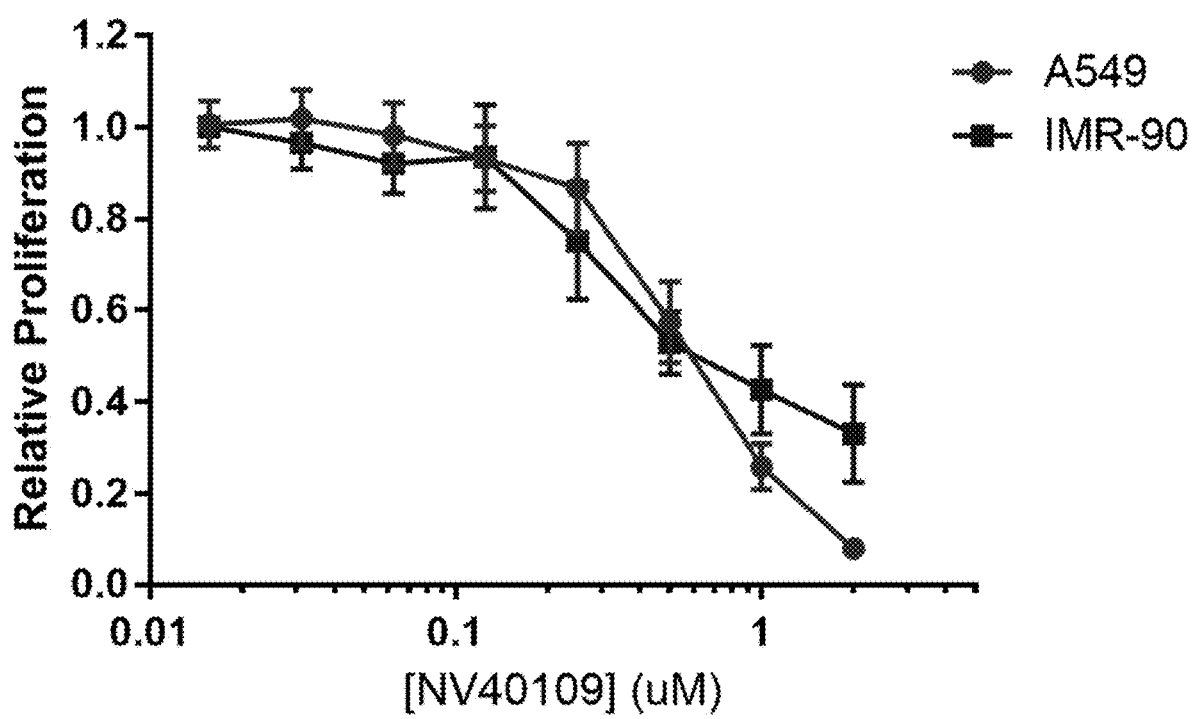
FIG. 3: Anti-proliferative activity of compound I-3 (NV40109) using MTT assay.
Figure 4:
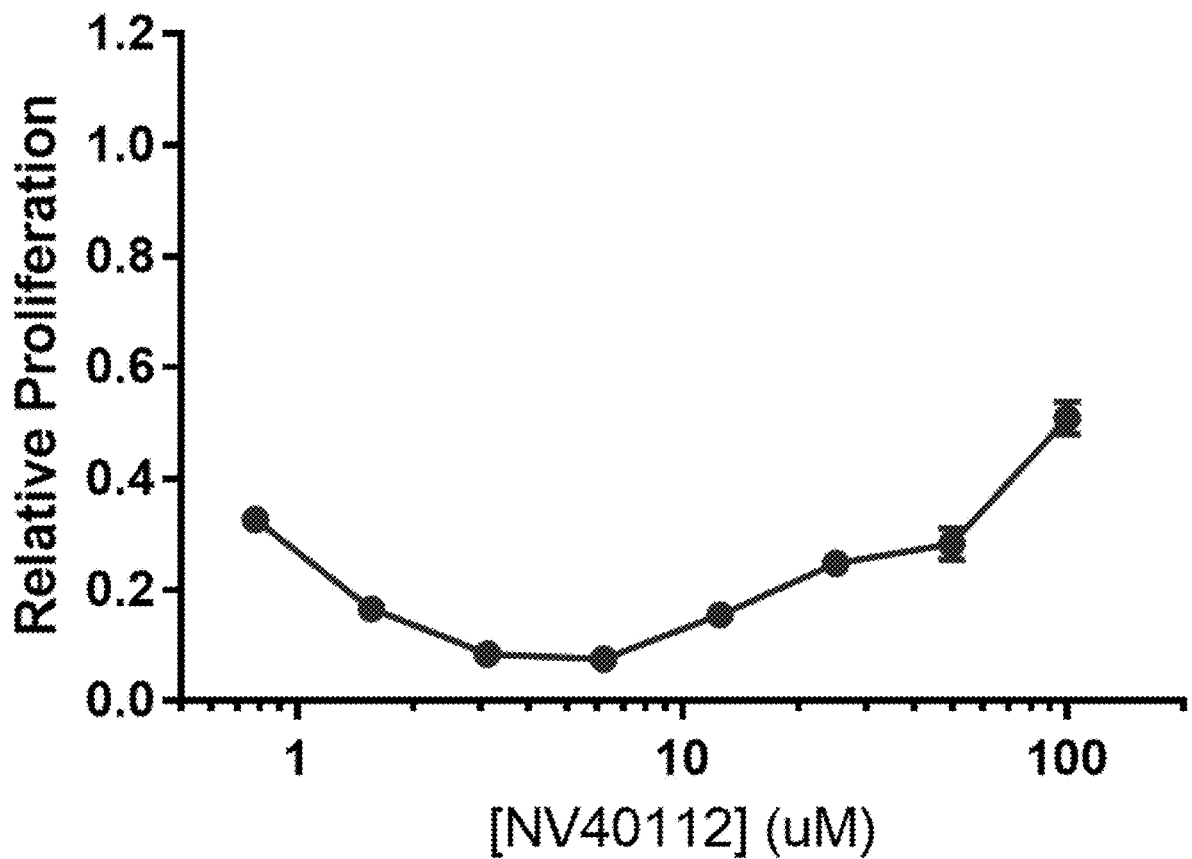
FIG. 4: Anti-proliferative activity of compound I-4 (NV40122) using MTT assay.
Figure 5:
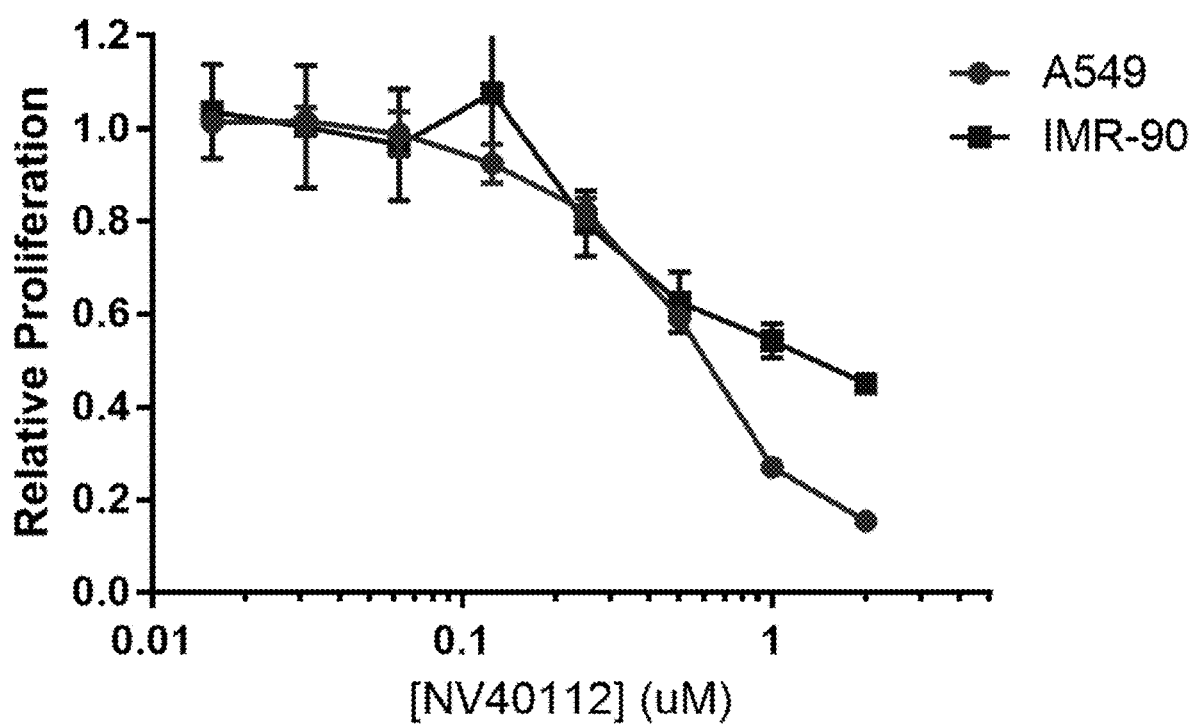
FIG. 5: Anti-proliferative activity of compound I-4 (NV40122) using MTT assay.
Figure 6:
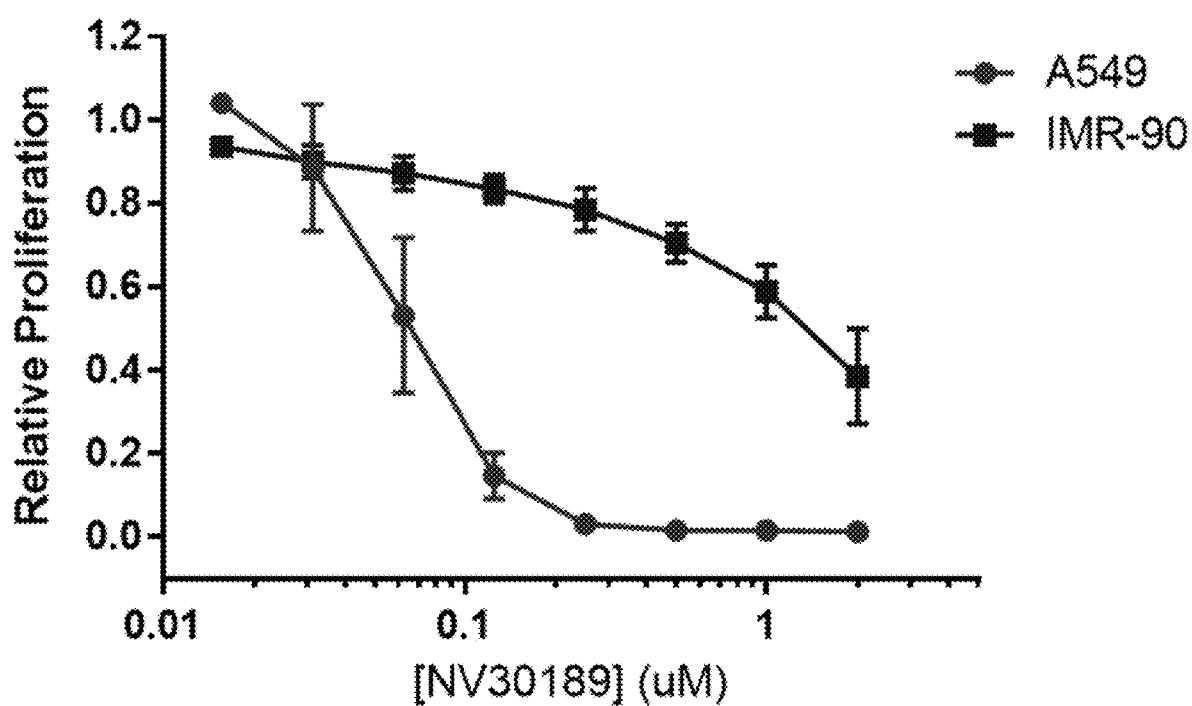
FIG. 6: Anti-proliferative activity of compound I-5 (NV30189) using MTT assay.
Figure 7:
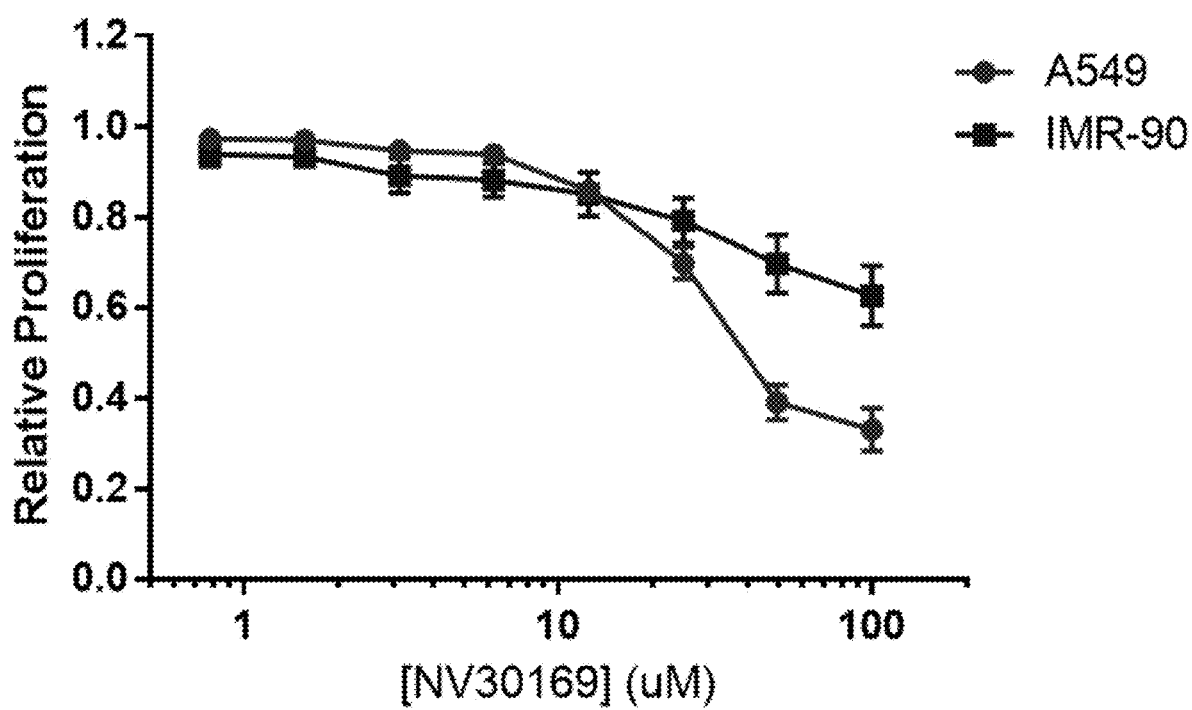
FIG. 7: Anti-proliferative activity of compound I-6 (NV30169) using MTT assay.
Figure 8:
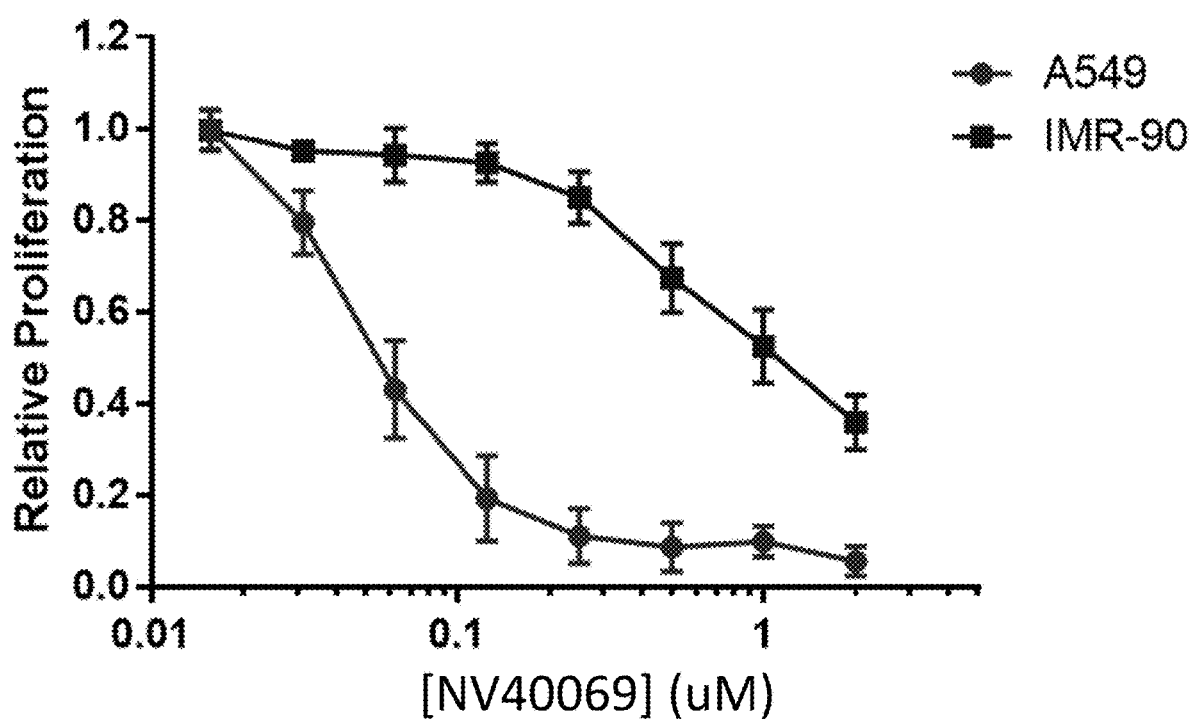
FIG. 8: Anti-proliferative activity of compound I-7 (NV40069) using MTT assay.
Figure 9:
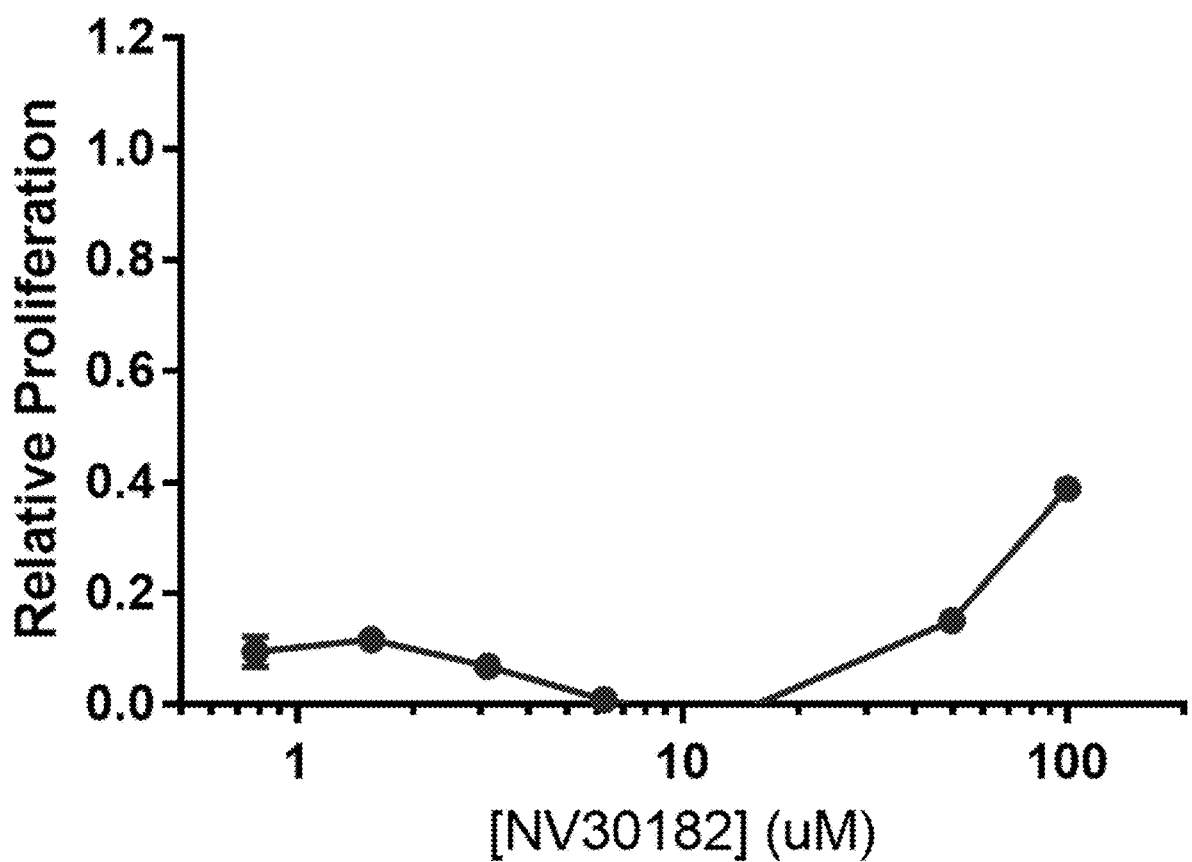
FIG. 9: Anti-proliferative activity of compound I-8 (NV30182) using MTT assay.
Figure 10:
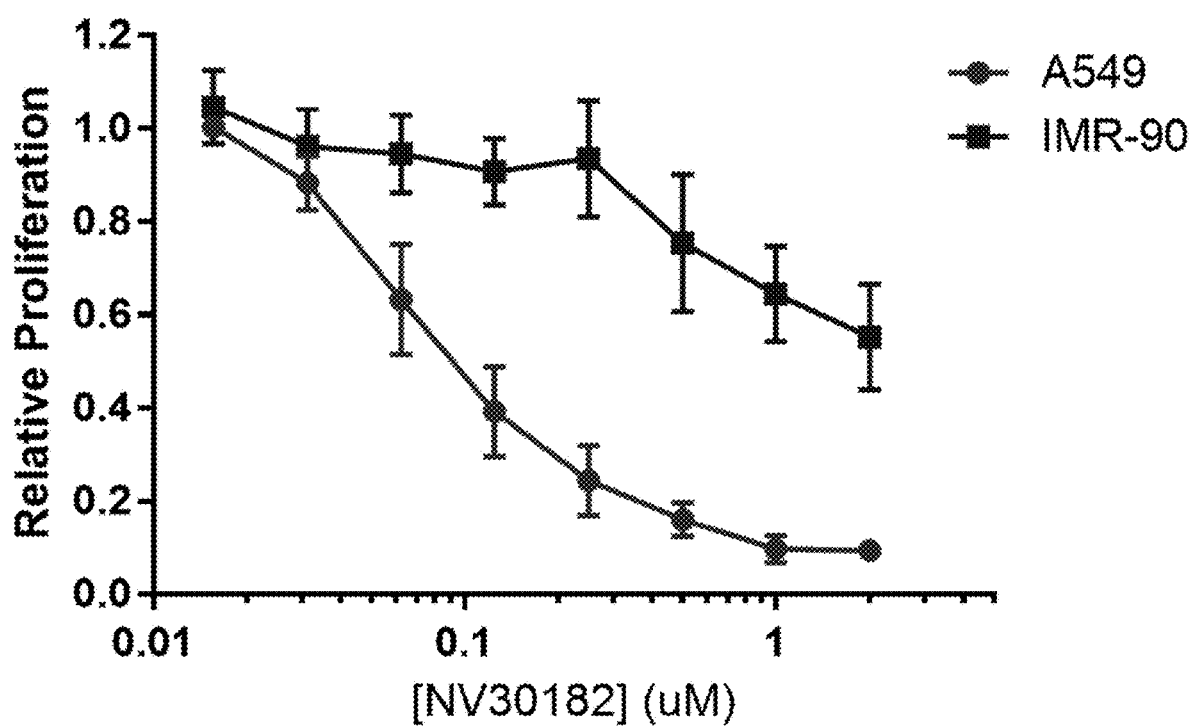
FIG. 10: Anti-proliferative activity of compound I-8 (NV30182) using MTT assay.
Figure 11:
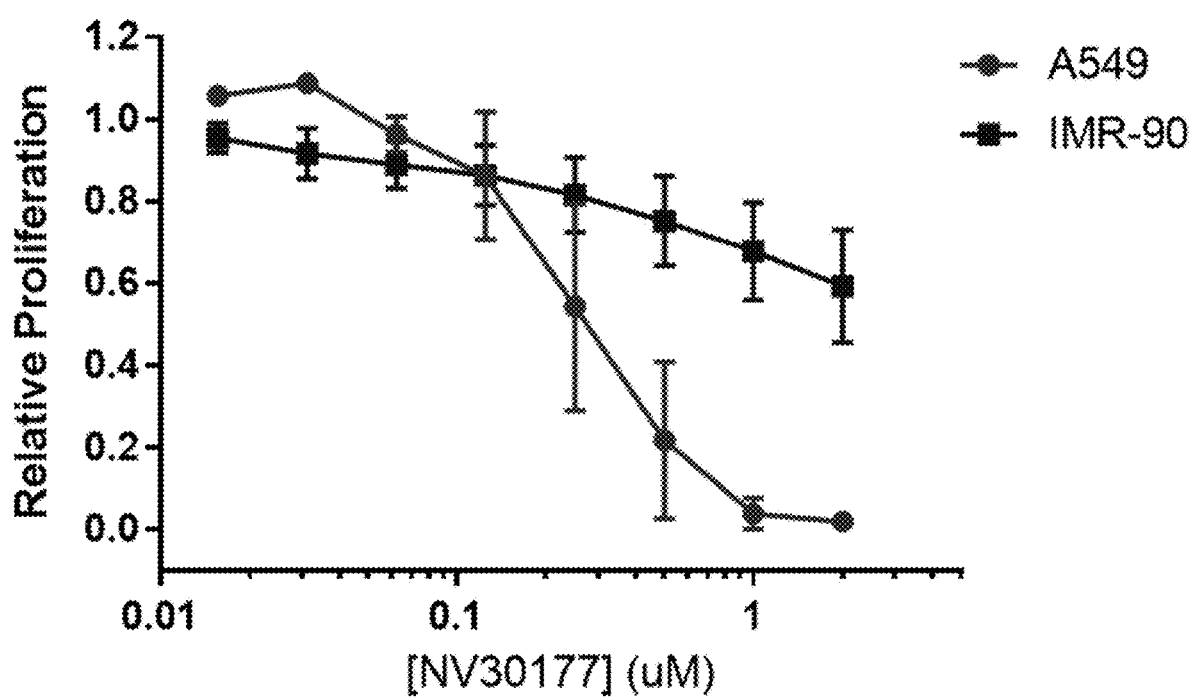
FIG. 11: Anti-proliferative activity of compound I-9 (NV30177) using MTT assay.
Figure 12:
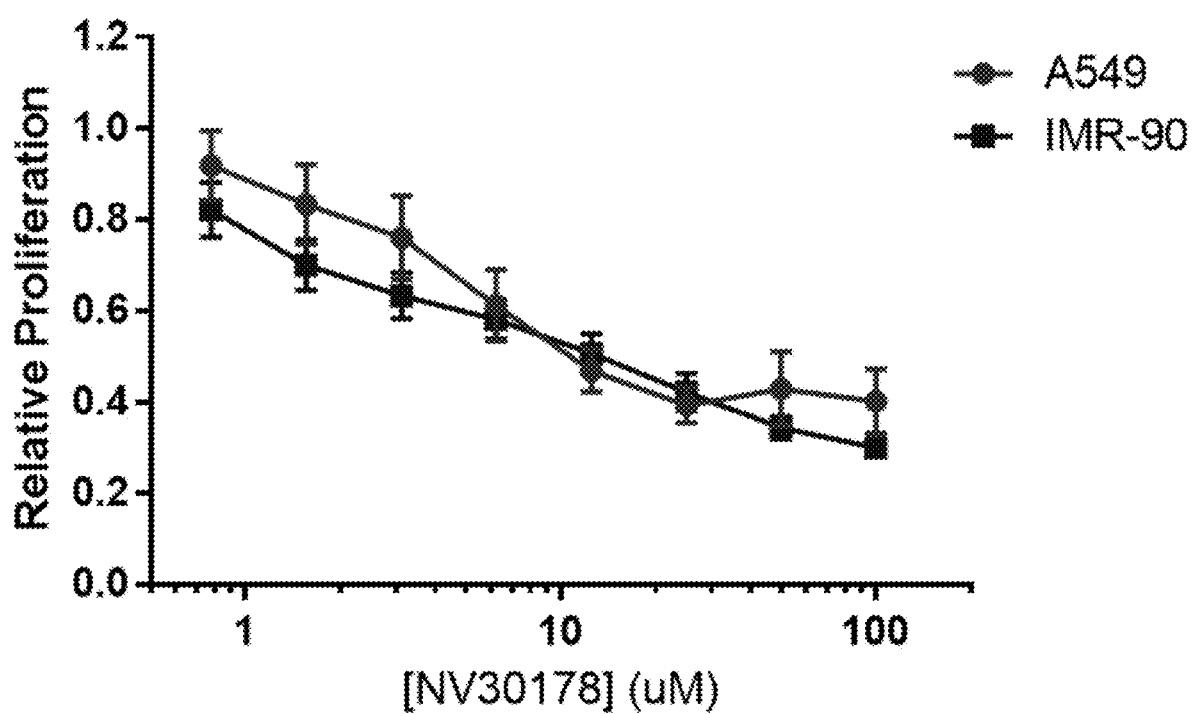
FIG. 12: Anti-proliferative activity of compound I-10 (NV30178) using MTT assay.
Figure 13:
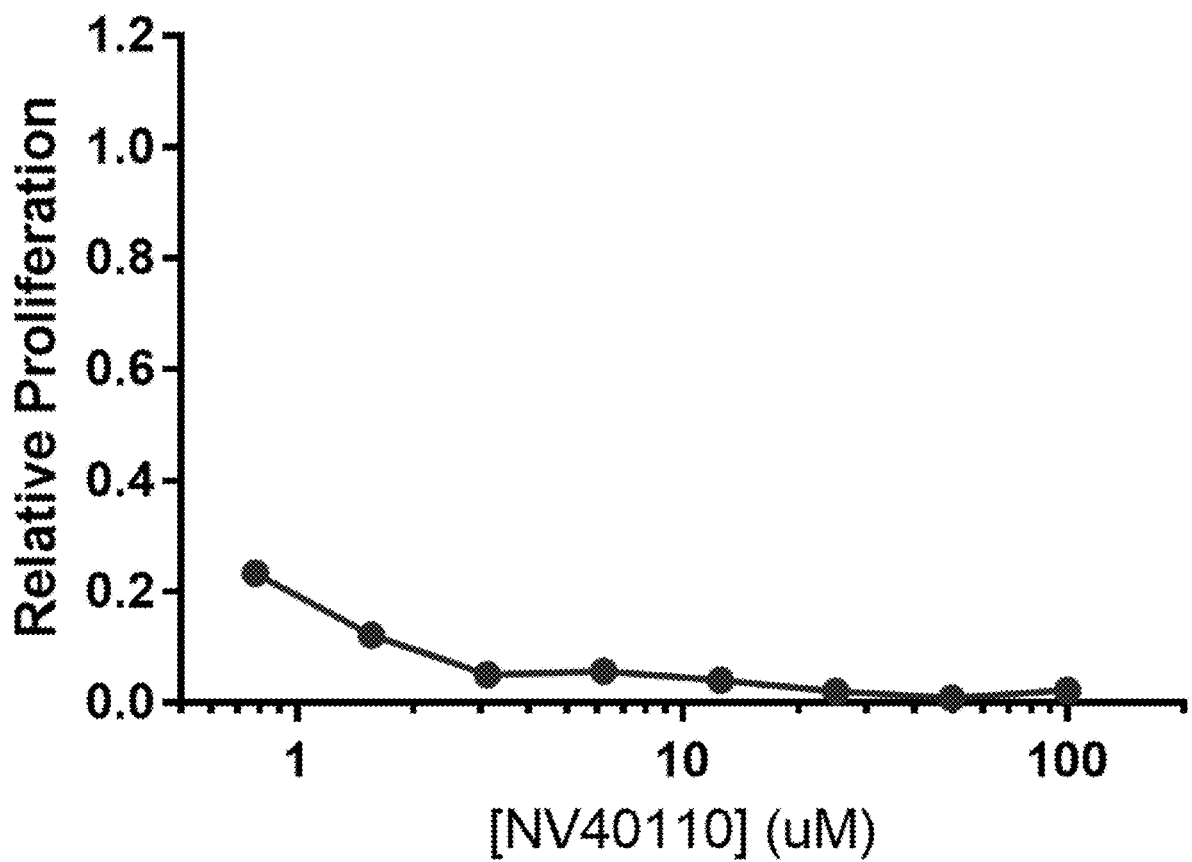
FIG. 13: Anti-proliferative activity of compound I-11 (NV40110) using MTT assay.
Figure 14:
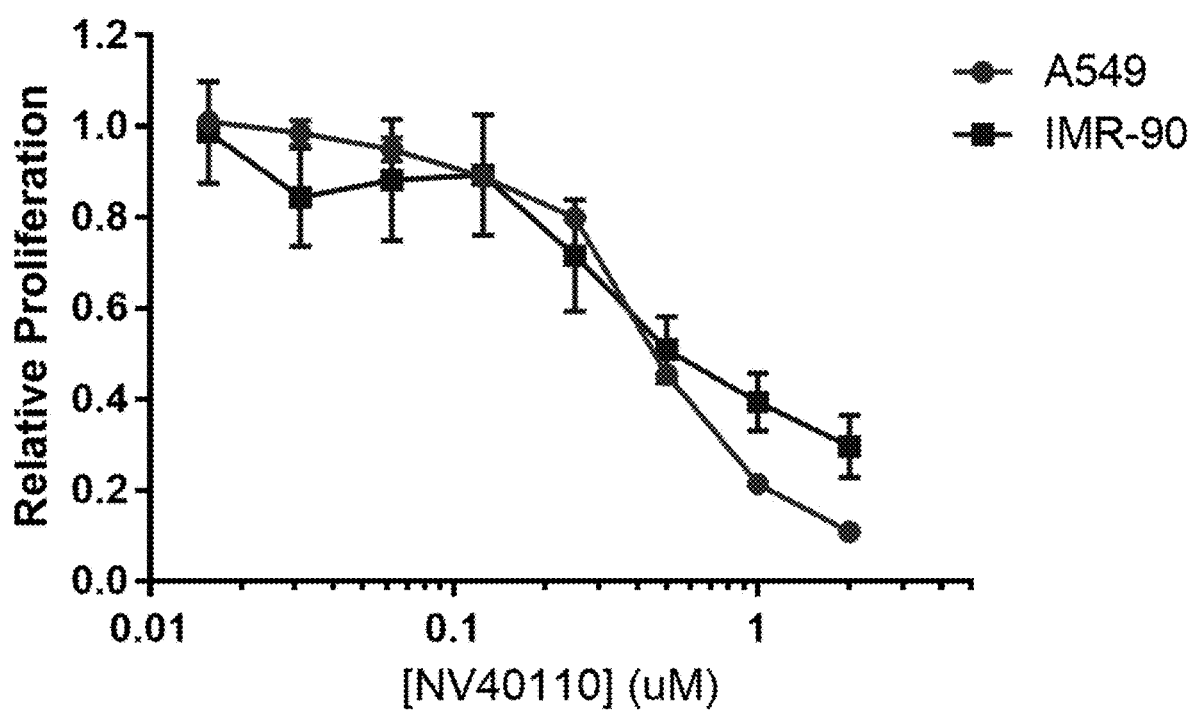
FIG. 14: Anti-proliferative activity of compound I-11 (NV40110) using MTT assay.
Figure 15:
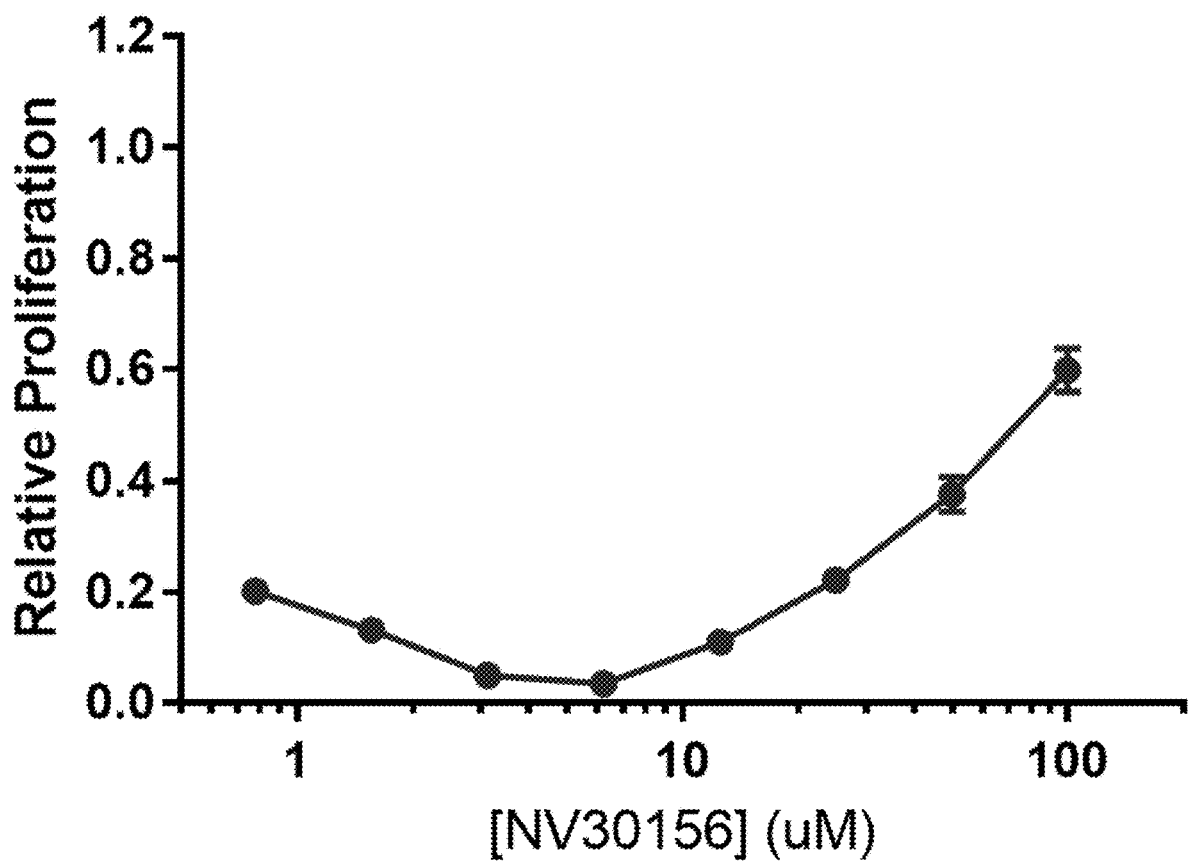
FIG. 15: Anti-proliferative activity of compound I-12 (NV30156) using MTT assay.
Figure 16:
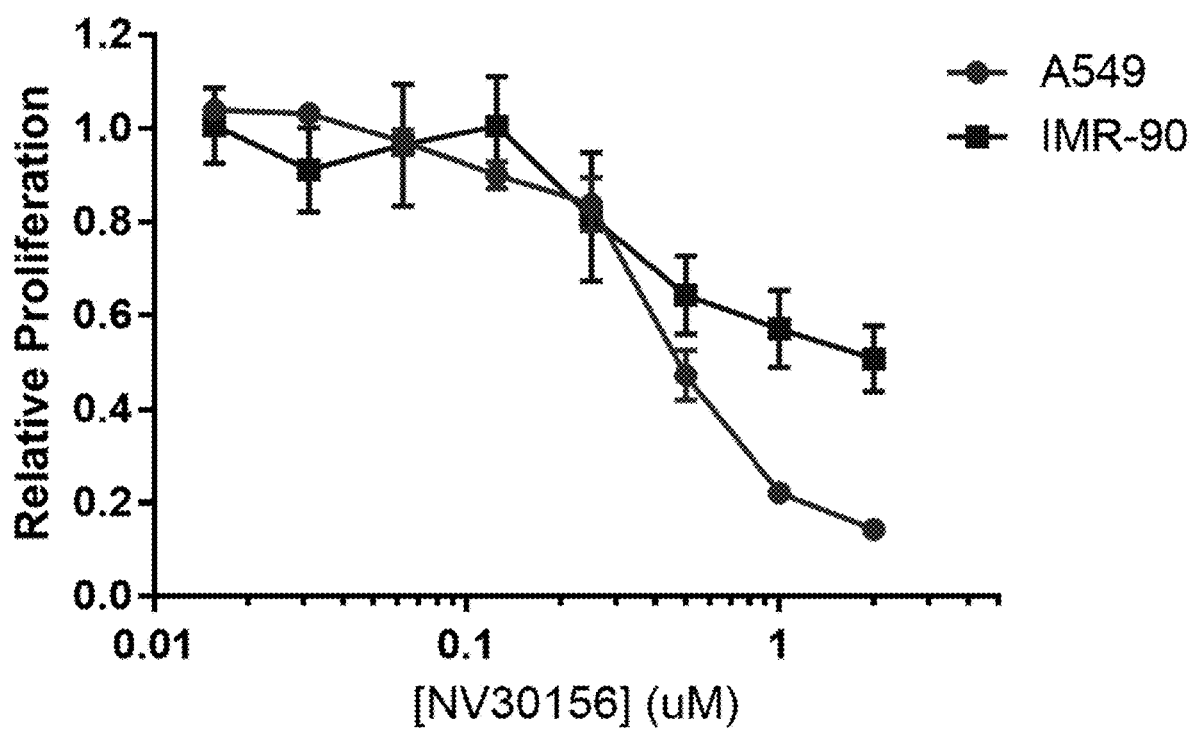
FIG. 16: Anti-proliferative activity of compound I-12 (NV30156) using MTT assay.
Figure 17:
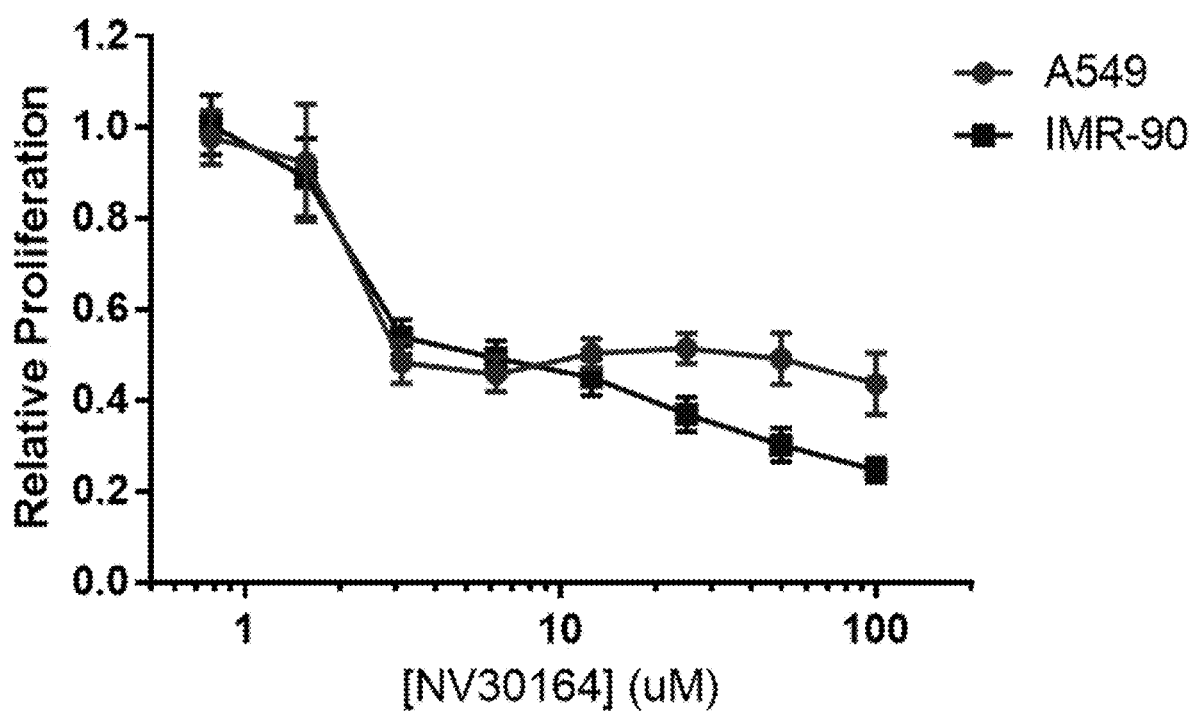
FIG. 17: Anti-proliferative activity of compound I-14 (NV30164) using MTT assay.
Figure 18:
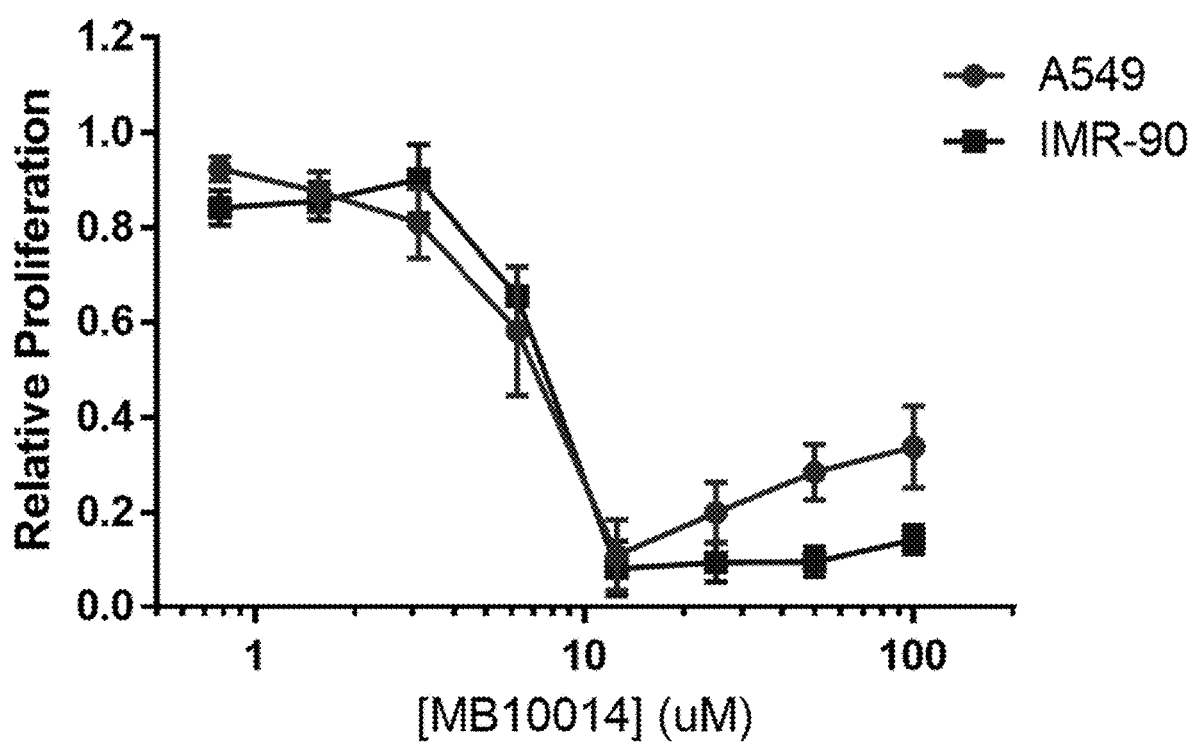
FIG. 18: Anti-proliferative activity of compound I-22 (MB 10014) using MTT assay.

While embodiments encompassing the general inventive concepts may take diverse forms, various embodiments will be described herein, with the understanding that the present disclosure is to be considered merely exemplary, and the general inventive concepts are not intended to be limited to the disclosed embodiments.

Some embodiments of the invention include inventive compounds (e.g., compounds of Formula (I) or (Ia)). Other embodiments include compositions (e.g., pharmaceutical compositions) comprising the inventive compound. Still other embodiments of the invention include compositions (e.g., pharmaceutical compositions) for treating, for example, certain diseases using the inventive compounds. Some embodiments include methods of using the inventive compound (e.g., in compositions or in pharmaceutical compositions) for administering and treating (e.g., diseases such as cancer). Further embodiments include methods for making the inventive compounds. Additional embodiments of the invention are also discussed herein.

As used herein (unless otherwise specified), the term "alkyl" means a monovalent, straight or branched hydrocarbon chain. For example, the terms "$C_1$-$C_7$ alkyl" or "$C_1$-$C_4$ alkyl" refer to straight- or branched-chain saturated hydrocarbon groups having from 1 to 7 (e.g., 1, 2, 3, 4, 5, 6, or 7), or 1 to 4 (e.g., 1, 2, 3, or 4), carbon atoms, respectively. Examples of $C_1$-$C_7$ alkyl groups include, but are not limited to, methyl, ethyl, n-propyl, i-propyl, n-butyl, s-butyl, t-butyl, n-pentyl, s-pentyl, n-hexyl, and n-septyl. Examples of $C_1$-$C_4$ alkyl groups include, but are not limited to, methyl, ethyl, n-propyl, i-propyl, n-butyl, s-butyl, and t-butyl.

As used herein (unless otherwise specified), the term "alkenyl" means a monovalent, straight or branched hydrocarbon chain that includes one or more (e.g., 1, 2, 3, or 4) double bonds. Examples of alkenyl groups include, but are not limited to, vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, and 5-hexenyl.

As used herein (unless otherwise specified), the term "alkoxy" means any of the above alkyl groups which is attached to the remainder of the molecule by an oxygen atom (alkyl-O—). Examples of alkoxy groups include, but are not limited to, methoxy (sometimes shown as MeO—), ethoxy, isopropoxy, propoxy, and butyloxy.

As used herein (unless otherwise specified), the term "alkynyl" means a monovalent, straight or branched hydrocarbon chain that includes one or more (e.g., 1, 2, 3, or 4) triple bonds and that also may optionally include one or more (e.g. 1, 2, 3, or 4) double bonds in the chain. Examples of alkynyl groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

As used herein (unless otherwise specified), the term "aryl" means a monovalent, monocyclic or bicyclic, 5, 6, 7, 8, 9, 10, 11, or 12 membered aromatic hydrocarbon group which, when unsubstituted. Examples of aryl groups include, but are not limited to, phenyl, naphthyl, tolyl, and xylyl. For a bicyclic aryl that is designated as substituted, one or both rings can be substituted.

As used herein (unless otherwise specified), the term "cycloalkyl" means a monovalent, monocyclic or bicyclic, 3, 4, 5, 6, 7, 8, 9, 10, 11, or 12 membered hydrocarbon group. The rings can be saturated or partially unsaturated. Examples of cycloalkyl groups include, but are not limited to, cyclopropyl, cyclobutyl, cyclopentyl, cyclohexyl, cycloheptyl, cyclooctyl, and bicycloalkyls (e.g., bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds). For a monocyclic cycloalkyl, the ring is not aromatic. For a bicyclic cycloalkyl, if one ring is aromatic, then the other is not aromatic. For a bicyclic cycloalkyl that is designated as substituted, one or both rings can be substituted.

As used herein (unless otherwise specified), the term "halogen" means monovalent Cl, F, Br, or I.

As used herein (unless otherwise specified), the term "heteroaryl" means a monovalent, monocyclic or bicyclic, 5, 6, 7, 8, 9, 10, 11, or 12 membered, hydrocarbon group, where 1, 2, 3, 4, 5, or 6 carbon atoms are replaced by a hetero atom independently selected from nitrogen, oxygen, or sulfur atom, and the monocyclic or bicyclic ring system is aromatic. Examples of heteroaryl groups include, but are not limited to, thienyl (or thiophenyl), furyl, indolyl, pyrrolyl, pyridinyl, pyrazinyl, oxazolyl, thiaxolyl, quinolinyl, pyrimidinyl, imidazolyl, triazolyl, tetrazolyl, 1H-pyrazol-4-yl, 1-Me-pyrazol-4-yl, pyridin-3-yl, pyridin-4-yl, 3,5-dimethyl-isoxazolyl, 1H-pyrrol-3-yl, 3,5-di-Me-pyrazolyl, and 1H-pyrazol-4-yl. For a bicyclic heteroaryl, if one ring is aryl, then the other is heteroaryl. For a bicyclic heteroaryl, one or both rings can have one or more hetero atoms. For a bicyclic heteroaryl that is designated as substituted, one or both rings can be substituted.

As used herein (unless otherwise specified), the term "heterocyclyl" means a monovalent, monocyclic or bicyclic, 5, 6, 7, 8, 9, 10, 11, or 12 membered, hydrocarbon, where 1, 2, 3, 4, 5, or 6 carbon atoms are replaced by a hetero atom independently selected from nitrogen atom, oxygen atom, or sulfur atom, and the monocyclic or bicyclic ring system is not aromatic. Examples of heterocyclyl groups include, but are not limited to, tetrahydropyran, pyrolidinyl (e.g., pyrrolidin-1-yl, pyrrolidin-2-yl, pyrrolidin-3-yl, or pyrrolidin-4-yl), piperazinyl (e.g., piperazin-1-yl, piperazin-2-yl, piperazin-3-yl, or piperazin-4-yl), piperidinyl (e.g., piperadin-1-yl, piperadin-2-yl, piperadin-3-yl, or piperadin-4-yl), and morpholinyl (e.g., morpholin-1-yl, morpholin-2-yl, morpholin-3-yl, or morpholin-4-yl). For a bicyclic heterocyclyl, if one ring is aromatic (e.g., monocyclic aryl or heteroaryl), then the other ring is not aromatic. For a bicyclic heterocyclyl, one or both rings can have one or more hetero atoms. For a bicyclic heterocyclyl that is designated as substituted, one or both rings can be substituted.

As used herein (unless otherwise specified), the term "hetero atom" means an atom selected from nitrogen atom, oxygen atom, or sulfur atom.

As used herein (unless otherwise specified), the terms "hydroxy" or "hydroxyl" indicates the presence of a monovalent —OH group.

As used herein (unless otherwise specified), the term "substituted" (e.g., as in substituted alkyl) means that one or more hydrogen atoms of a chemical group (with one or more hydrogen atoms) can be replaced by one or more non-hydrogen substituents selected from the specified options. The replacement can occur at one or more positions. The term "optionally substituted" means that one or more hydrogen atoms of a chemical group (with one or more hydrogen atoms) can be, but is not required to be, substituted.

Some compounds of the invention can have one or more chiral centers and can exist in and be isolated in optically active and racemic forms, for any of the one or more chiral centers. Some compounds can exhibit polymorphism. The compounds of the present invention (e.g., Formula I) encompass any optically active, racemate, stereoisomer form, polymorphism, or mixtures thereof. If a chiral center does not provide an indication of its configuration (i.e., R or S) in a chemical structure, it should be considered to represent R, S or a racemate.

Compounds and Compositions Including Pharmaceutical Compositions

Some embodiments of the invention include compounds of Formula (Ia) and (Ib) (collectively Formula (Ia) and Formula (Ib) are referred to as Formula (I)):

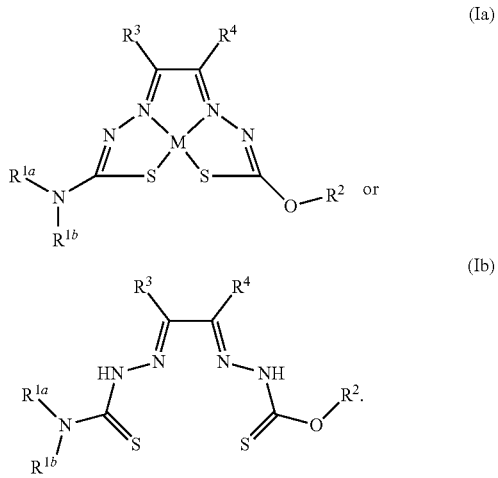

In some embodiments, $R^{1a}$ can be monovalent H, halogen (e.g., F, Cl, Br, or I), —CN, hydroxy (—OH), methanoyl (—COH), carboxy (—CO$_2$H), $C_1$-$C_{10}$ alkyl (e.g., $C_1$, $C_2$, $C_3$, $C_4$, $C_5$, $C_6$, $C_7$, $C_8$, $C_9$, or $C_{10}$ alkyl), $C_2$-$C_{10}$ alkenyl (e.g., $C_2$, $C_3$, $C_4$, $C_5$, $C_6$, $C_7$, $C_8$, $C_9$, or $C_{10}$ alkenyl), $C_2$-$C_{10}$ alkynyl (e.g., $C_2$, $C_3$, $C_4$, $C_5$, $C_6$, $C_7$, $C_8$, $C_9$, or $C_{10}$ alkynyl), $C_1$-$C_9$ alkoxy (e.g., $C_1$, $C_2$, $C_3$, $C_4$, $C_5$, $C_6$, $C_7$, $C_8$, or $C_9$ alkoxy), cycloalkyl, heterocyclyl, aryl, or heteroaryl, which methanoyl (—COH), carboxy (—CO$_2$H), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, —CF$_3$, —OCF$_3$, or $C_1$-$C_3$ alkoxy. In other embodiments, $R^{1a}$ can be monovalent H, halogen (e.g., F, Cl, Br, or I), —CN, hydroxy (—OH), methanoyl (—COH), carboxy (—CO$_2$H), $C_1$-$C_7$ alkyl (e.g., $C_1$, $C_2$, $C_3$, $C_4$, $C_5$, $C_6$, or $C_7$ alkyl), $C_1$-$C_6$ alkoxy (e.g., $C_1$, $C_2$, $C_3$, $C_4$, $C_5$, or $C_6$ alkoxy), cycloalkyl, heterocyclyl, aryl, or heteroaryl, which methanoyl (—COH), carboxy (—CO$_2$H), $C_1$-$C_7$ alkyl, $C_1$-$C_6$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, —CF$_3$, —OCF$_3$, or $C_1$-$C_3$ alkoxy. In some embodiments, $R^{1a}$ can be H, Cl, hydroxy (—OH), methyl, ethyl, $C_{1-5}$ alkyl, $C_3$ alkyl(e.g., n-propyl or isopropyl), —CN, ethynyl, —CONH$_2$, —CON(CH$_3$)$_2$, 2-(morpholinyl)ethoxy, —CO-morpholin-4-yl, ethoxy, methoxy, 5-hydroxy pyridyl (e.g., 5-hydroxy pyrid-3-yl), indolyl (e.g., 1-indolyl), 1,2,3,4-tetrahydroisoquinolyl (e.g., 2-1,2,3,4-tetrahydroisoquinolyl), 1,2-methylenedioxyphenyl, 2,3-methylenedioxyphenyl, furyl (e.g., 2-furyl), 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl. In some embodiments, $R^{1a}$ can be H, methyl, ethyl, $C_3$ alkyl, n-propyl, isopropyl, ethoxy, methoxy, 5-hydroxy pyridyl (e.g., 5-hydroxy pyrid-3-yl), indolyl (e.g., 1-indolyl), 1,2,3,4-tetrahydroisoquinolyl (e.g., 2-1,2,3,4-tetrahydroisoquinolyl), furyl (e.g., 2-furyl), 1,2-methylenedioxyphenyl, 2,3-methylenedioxyphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl. In some embodiments, $R^{1a}$ can be H, methyl, ethyl, n-propyl, or phenyl. In other embodiments, $R^{1a}$ is not H.

In some embodiments, $R^{1b}$ can be monovalent H, halogen (e.g., F, Cl, Br, or I), —CN, hydroxy (—OH), methanoyl (—COH), carboxy (—CO$_2$H), $C_1$-$C_{10}$ alkyl (e.g., $C_1$, $C_2$, $C_3$, $C_4$, $C_5$, $C_6$, $C_7$, $C_8$, $C_9$, or $C_{10}$ alkyl), $C_2$-$C_{10}$ alkenyl (e.g., $C_2$, $C_3$, $C_4$, $C_5$, $C_6$, $C_7$, $C_8$, $C_9$, or $C_{10}$ alkenyl), $C_2$-$C_{10}$ alkynyl (e.g., $C_2$, $C_3$, $C_4$, $C_5$, $C_6$, $C_7$, $C_8$, $C_9$, or $C_{10}$ alkynyl), $C_1$-$C_9$ alkoxy (e.g., $C_1$, $C_2$, $C_3$, $C_4$, $C_5$, $C_6$, $C_7$, $C_8$, or $C_9$ alkoxy), cycloalkyl, heterocyclyl, aryl, or heteroaryl, which methanoyl (—COH), carboxy (—CO$_2$H), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, —CF$_3$, —OCF$_3$, or $C_1$-$C_3$ alkoxy. In other embodiments, $R^{1b}$ can be monovalent H, halogen (e.g., F, Cl, Br, or I), —CN, hydroxy (—OH), methanoyl (—COH), carboxy (—CO$_2$H), $C_1$-$C_7$ alkyl (e.g., $C_1$, $C_2$, $C_3$, $C_4$, $C_5$, $C_6$, or $C_7$ alkyl), $C_1$-$C_6$ alkoxy (e.g., $C_1$, $C_2$, $C_3$, $C_4$, $C_5$, or $C_6$ alkoxy), cycloalkyl, heterocyclyl, aryl, or heteroaryl, which methanoyl (—COH), carboxy (—CO$_2$H), $C_1$-$C_7$ alkyl, $C_1$-$C_6$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, —CF$_3$, —OCF$_3$, or $C_1$-$C_3$ alkoxy. In some embodiments, $R^{1b}$ can be H, Cl, hydroxy (—OH), methyl, ethyl, $C_{1-5}$ alkyl, $C_3$ alkyl (e.g., n-propyl or isopropyl), $C_4$ alkyl, —CN, ethynyl, —CONH$_2$, —CON(CH$_3$)$_2$, 2-(morpholinyl)ethoxy, —CO-morpholin-4-yl, ethoxy, methoxy, 5-hydroxy pyridyl (e.g., 5-hydroxy pyrid-3-yl), indolyl (e.g., 1-indolyl), 1,2,3,4-tetrahydroisoquinolyl (e.g., 2-1,2,3,4-tetrahydroisoquinolyl), 1,2-methylenedioxyphenyl, 2,3-methylenedioxyphenyl, furyl (e.g., 2-furyl), 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl. In some embodiments, $R^{1b}$ can be H, methyl, ethyl, $C_3$ alkyl, n-propyl, isopropyl, ethoxy, methoxy, 5-hydroxy pyridyl (e.g., 5-hydroxy pyrid-3-yl), indolyl (e.g., 1-indolyl), 1,2,3,4-tetrahydroisoquinolyl (e.g., 2-1,2,3,4-tetrahydroisoquinolyl), furyl (e.g., 2-furyl), 1,2-methylenedioxyphenyl, 2,3-methylenedioxyphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl. In some embodiments, $R^{1b}$ can be H, methyl, ethyl, n-propyl, or phenyl. In other embodiments, $R^{1b}$ is not H.

In other embodiments, $R^{1a}$ and $R^{1b}$ can be bonded together (with their attached nitrogen) to form heterocyclyl or heteroaryl, which heterocyclyl or heteroaryl can optionally be substituted with one or more (e.g., 0, 1, 2, 3, 4, 5, or 6) of halogen (e.g., F, Cl, Br, or I), oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, —CF$_3$, —OCF$_3$, or $C_1$-$C_3$ alkoxy. In some embodiments, $R^{1a}$ and $R^{1b}$ can be bonded together to form pyrrolidinyl, pyrrolinyl, imidazolidinyl, pyrazolidinyl, piperidyl, piperazinyl, indolinyl, morpholinyl, pyrrolyl, pyrazolyl, isoxazolyl, pyrazinyl, pyridyl, 5-hydroxy pyridyl, indolyl, indazolyl, or 1,2,3,4-tetrahydroisoquinolyl. In some embodiments, $R^{1a}$ and $R^{1b}$ are not bonded together.

In some embodiments, $R^2$ can be monovalent H, halogen (e.g., F, Cl, Br, or I), —CN, hydroxy (—OH), methanoyl (—COH), carboxy (—CO$_2$H), $C_1$-$C_{10}$ alkyl (e.g., $C_1$, $C_2$, $C_3$, $C_4$, $C_5$, $C_6$, $C_7$, $C_8$, $C_9$, or $C_{10}$ alkyl), $C_2$-$C_{10}$ alkenyl (e.g., $C_2$, $C_3$, $C_4$, $C_5$, $C_6$, $C_7$, $C_8$, $C_9$, or $C_{10}$ alkenyl), $C_2$-$C_{10}$ alkynyl (e.g., $C_2$, $C_3$, $C_4$, $C_5$, $C_6$, $C_7$, $C_8$, $C_9$, or $C_{10}$ alkynyl), $C_1$-$C_9$ alkoxy (e.g., $C_1$, $C_2$, $C_3$, $C_4$, $C_5$, $C_6$, $C_7$, $C_8$, or $C_9$ alkoxy), cycloalkyl, heterocyclyl, aryl, or heteroaryl, which methanoyl (—COH), carboxy (—CO$_2$H), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy. In other embodiments, R$^2$ can be monovalent H, halogen (e.g., F, Cl, Br, or I), —CN, hydroxy (—OH), methanoyl (—COH), carboxy (—CO$_2$H), C$_1$-C$_7$ alkyl (e.g., C$_1$, C$_2$, C$_3$, C$_4$, C$_5$, C$_6$, or C$_7$ alkyl), C$_1$-C$_6$ alkoxy (e.g., C$_1$, C$_2$, C$_3$, C$_4$, C$_5$, or C$_6$ alkoxy), cycloalkyl, heterocyclyl, aryl, or heteroaryl, which methanoyl (—COH), carboxy (—CO$_2$H), C$_1$-C$_7$ alkyl, C$_1$-C$_6$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy. In some embodiments, R$^2$ can be Cl, hydroxy (—OH), methyl, ethyl, C$_{1-5}$ alkyl, C$_3$ alkyl (e.g., n-propyl or isopropyl), —CN, ethynyl, —CONH$_2$, —CON(CH$_3$)$_2$, 2-(morpholinyl)ethoxy, —CO-morpholin-4-yl, ethoxy, methoxy, 5-hydroxy pyridyl (e.g., 5-hydroxy pyrid-3-yl), indolyl (e.g., 1-indolyl), 1,2,3,4-tetrahydroisoquinolyl (e.g., 2-1,2,3,4-tetrahydroisoquinolyl), 1,2-methylenedioxyphenyl, 2,3-methylenedioxyphenyl, furyl (e.g., 2-furyl), 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl. In some embodiments, R$^2$ can be methyl, ethyl, C$_3$ alkyl, n-propyl, isopropyl, ethoxy, methoxy, 5-hydroxy pyridyl (e.g., 5-hydroxy pyrid-3-yl), indolyl (e.g., 1-indolyl), 1,2,3,4-tetrahydroisoquinolyl (e.g., 2-1,2,3,4-tetrahydroisoquinolyl), furyl (e.g., 2-furyl), 1,2-methylenedioxyphenyl, 2,3-methylenedioxyphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl. In some embodiments, R$^2$ can be methyl, ethyl, n-propyl, or phenyl. In other embodiments, R$^2$ is not H.

In some embodiments, R$^3$ can be monovalent H, halogen (e.g., F, Cl, Br, or I), —CN, hydroxy (—OH), methanoyl (—COH), carboxy (—CO$_2$H), C$_1$-C$_{10}$ alkyl (e.g., C$_1$, C$_2$, C$_3$, C$_4$, C$_5$, C$_6$, C$_7$, C$_8$, C$_9$, or C$_{10}$ alkyl), C$_2$-C$_{10}$ alkenyl (e.g., C$_2$, C$_3$, C$_4$, C$_5$, C$_6$, C$_7$, C$_8$, C$_9$, or C$_{10}$ alkenyl), C$_2$-C$_{10}$ alkynyl (e.g., C$_2$, C$_3$, C$_4$, C$_5$, C$_6$, C$_7$, C$_8$, C$_9$, or C$_{10}$ alkynyl), C$_1$-C$_9$ alkoxy (e.g., C$_1$, C$_2$, C$_3$, C$_4$, C$_5$, C$_6$, C$_7$, C$_8$, or C$_9$ alkoxy), cycloalkyl, heterocyclyl, aryl, or heteroaryl, which methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy. In other embodiments, R$^3$ can be monovalent H, halogen (e.g., F, Cl, Br, or I), —CN, hydroxy (—OH), methanoyl (—COH), carboxy (—CO$_2$H), C$_1$-C$_7$ alkyl (e.g., C$_1$, C$_2$, C$_3$, C$_4$, C$_5$, C$_6$, or C$_7$ alkyl), C$_1$-C$_6$ alkoxy (e.g., C$_1$, C$_2$, C$_3$, C$_4$, C$_5$, or C$_6$ alkoxy), cycloalkyl, heterocyclyl, aryl, or heteroaryl, which methanoyl (—COH), carboxy (—CO$_2$H), C$_1$-C$_7$ alkyl, C$_1$-C$_6$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy. In some embodiments, R$^3$ can be H, Cl, hydroxy (—OH), methyl, ethyl, C$_{1-5}$ alkyl, C$_3$ alkyl (e.g., n-propyl or isopropyl), —CN, ethynyl, —CONH$_2$, —CON(CH$_3$)$_2$, 2-(morpholinyl)ethoxy, —CO-morpholin-4-yl, ethoxy, methoxy, 5-hydroxy pyridyl (e.g., 5-hydroxy pyrid-3-yl), indolyl (e.g., 1-indolyl), 1,2,3,4-tetrahydroisoquinolyl (e.g., 2-1,2,3,4-tetrahydroisoquinolyl), 1,2-methylenedioxyphenyl, 2,3-methylenedioxyphenyl, furyl (e.g., 2-furyl), 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl. In some embodiments, R$^3$ can be H, methyl, ethyl, C$_3$ alkyl, n-propyl, isopropyl, ethoxy, methoxy, 5-hydroxy pyridyl (e.g., 5-hydroxy pyrid-3-yl), indolyl (e.g., 1-indolyl), 1,2,3,4-tetrahydroisoquinolyl (e.g., 2-1,2,3,4-tetrahydroisoquinolyl), furyl (e.g., 2-furyl), 1,2-methylenedioxyphenyl, 2,3-methylenedioxyphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl. In some embodiments, $R^3$ can be H, methyl, ethyl, n-propyl, or phenyl. In other embodiments, $R^3$ is not H.

In some embodiments, $R^4$ can be monovalent H, halogen (e.g., F, Cl, Br, or I), —CN, hydroxy (—OH), methanoyl (—COH), carboxy (—CO$_2$H), $C_1$-$C_{10}$ alkyl (e.g., $C_1$, $C_2$, $C_3$, $C_4$, $C_5$, $C_6$, $C_7$, $C_8$, $C_9$, or $C_{10}$ alkyl), $C_2$-$C_{10}$ alkenyl (e.g., $C_2$, $C_3$, $C_4$, $C_5$, $C_6$, $C_7$, $C_8$, $C_9$, or $C_{10}$ alkenyl), $C_2$-$C_{10}$ alkynyl (e.g., $C_2$, $C_3$, $C_4$, $C_5$, $C_6$, $C_7$, $C_8$, $C_9$, or $C_{10}$ alkynyl), $C_1$-$C_9$ alkoxy (e.g., $C_1$, $C_2$, $C_3$, $C_4$, $C_5$, $C_6$, $C_7$, $C_8$, or $C_9$ alkoxy), cycloalkyl, heterocyclyl, aryl, or heteroaryl, which methanoyl (—COH), carboxy (—CO$_2$H), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, —CF$_3$, —OCF$_3$, or $C_1$-$C_3$ alkoxy. In other embodiments, $R^4$ can be monovalent H, halogen (e.g., F, Cl, Br, or I), —CN, hydroxy (—OH), methanoyl (—COH), carboxy (—CO$_2$H), $C_1$-$C_7$ alkyl (e.g., $C_1$, $C_2$, $C_3$, $C_4$, $C_5$, $C_6$, or $C_7$ alkyl), $C_1$-$C_6$ alkoxy (e.g., $C_1$, $C_2$, $C_3$, $C_4$, $C_5$, or $C_6$ alkoxy), cycloalkyl, heterocyclyl, aryl, or heteroaryl, which methanoyl (—COH), carboxy (—CO$_2$H), $C_1$-$C_7$ alkyl, $C_1$-$C_6$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, —CF$_3$, —OCF$_3$, or $C_1$-$C_3$ alkoxy. In some embodiments, $R^4$ can be H, Cl, hydroxy (—OH), methyl, ethyl, $C_{1-5}$ alkyl, $C_3$ alkyl(e.g., n-propyl or isopropyl), —CN, ethynyl, —CONH$_2$, —CON(CH$_3$)$_2$, 2-(morpholinyl)ethoxy, —CO-morpholin-4-yl, ethoxy, methoxy, 5-hydroxy pyridyl (e.g., 5-hydroxy pyrid-3-yl), indolyl (e.g., 1-indolyl), 1,2,3,4-tetrahydroisoquinolyl (e.g., 2-1,2,3,4-tetrahydroisoquinolyl), 1,2-methylenedioxyphenyl, 2,3-methylenedioxyphenyl, furyl (e.g., 2-furyl), 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl. In some embodiments, $R^4$ can be H, methyl, ethyl, $C_3$ alkyl, n-propyl, isopropyl, ethoxy, methoxy, 5-hydroxy pyridyl (e.g., 5-hydroxy pyrid-3-yl), indolyl (e.g., 1-indolyl), 1,2,3,4-tetrahydroisoquinolyl (e.g., 2-1,2,3,4-tetrahydroisoquinolyl), furyl (e.g., 2-furyl), 1,2-methylenedioxyphenyl, 2,3-methylenedioxyphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl. In some embodiments, $R^4$ can be H, methyl, ethyl, n-propyl, or phenyl. In other embodiments, $R^4$ is not H.

In other embodiments, $R^3$ and $R^4$ can be bonded together (with their attached carbons) to form a ring that is fused to the attached carbons of $R^3$ and $R^4$, where the ring that is fused can be cycloalkyl, heterocyclyl, aryl, or heteroaryl, which cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, —CF$_3$, —OCF$_3$, or $C_1$-$C_3$ alkoxy. In some embodiments, $R^3$ and $R^4$ can be bonded together to form a ring that is fused to the attachments of $R^3$ and $R^4$, where the ring that is fused can be cyclobutyl, cyclopentyl, cyclohexyl, chlorocyclohexyl, fluorocyclohexyl, methoxycyclohexyl, ethoxycyclohexyl, methylcyclohexyl, trifluoromethylcyclohexyl, cycloheptyl, cyclooctyl, pyrrolidinyl, pyrrolinyl, imidazolidinyl, pyrazolidinyl, piperidyl, piperazinyl, indolinyl, morpholinyl, 5-hydroxy pyridyl, indolyl, 1,2,3,4-tetrahydroisoquinolyl, furyl, 1,2-methylenedioxyphenyl, 2,3-methylenedioxyphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, or methylenedioxyphenyl. In some embodiments, $R^3$ and $R^4$ are not bonded together.

In other embodiments, M can be a divalent cation. In certain embodiments, M can be iron (Fe), nickel (Ni), palladium (Pd), cadmium (Cd), manganese (Mn), cobalt (Co), copper (Cu), or zinc (Zn). In some embodiments, M can be nickel (Ni), copper (Cu), or zinc (Zn). In other embodiments, M can be nickel (Ni). In some embodiments, M can be zinc (Zn). In some embodiments, M can be copper (Cu).

In certain embodiments, Formula (I) is only Formula (Ia) (i.e., Formula (Ib) is excluded from Formula (I)). In other embodiments, Formula (I) is only Formula (Ib) (i.e., Formula (Ia) is excluded from Formula (I)).

In some embodiments, the compounds of Formula (I) can be selected from those specified in Table 1.

TABLE 1

| Compound Number (alternative designation) | Compound Structure |
| --- | --- |
| I-1 (NV3104) | 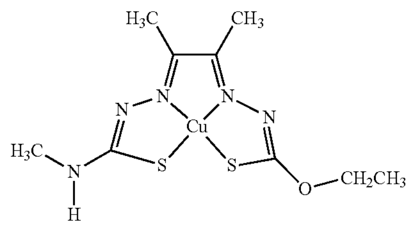 |
| I-2 | 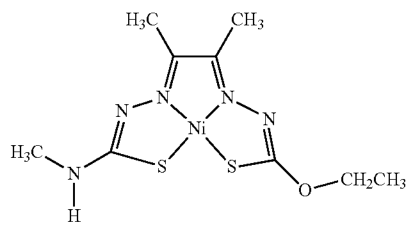 |
| I-3 (NV40109) | 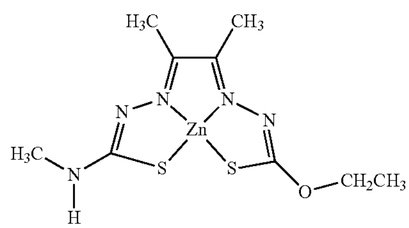 |
| I-4 (NV40112) | 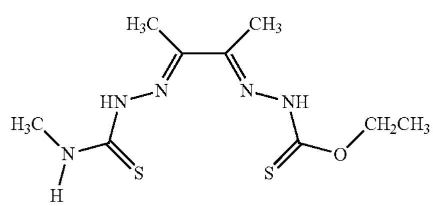 [SMILES: CCOC(=S)N/N=C(C)/C(C)=N/NC(=S)NC] |
| I-5 (NV30189) | 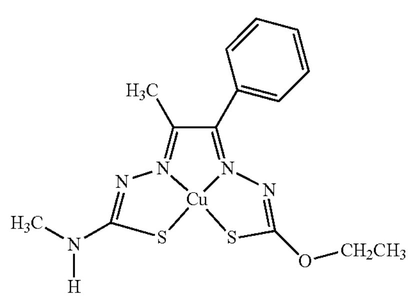 |
| I-6 (NV30169) | 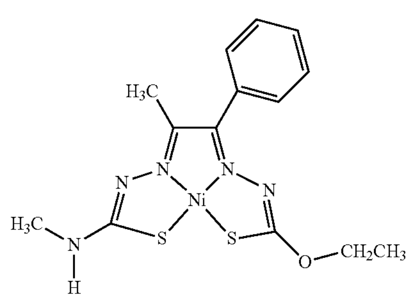 |

TABLE 1-continued

| Compound Number (alternative designation) | Compound Structure |
|---|---|
| I-7 (NV40069) | Zn complex with methyl/phenyl substituted bis(thiosemicarbazone), N-methyl and O-ethyl groups |
| I-8 (NV30182) | Free ligand: methyl/phenyl bis(thiosemicarbazone), N-methyl thiosemicarbazide and O-ethyl xanthate ester |
| I-9 (NV30177) | Cu complex with dimethyl bis(thiosemicarbazone), N-methyl and O-propyl (O—(CH$_2$)$_2$CH$_3$) groups |
| I-10 (NV30178) | Ni complex with dimethyl bis(thiosemicarbazone), N-methyl and O-propyl (O—(CH$_2$)$_2$CH$_3$) groups |
| I-11 (NV40110) | Zn complex with dimethyl bis(thiosemicarbazone), N-methyl and O-propyl (O—(CH$_2$)$_2$CH$_3$) groups |
| I-12 (NV30156) | Free ligand: dimethyl bis(thiosemicarbazone), N-methyl thiosemicarbazide and O-propyl (O—(CH$_2$)$_2$CH$_3$) xanthate ester |

TABLE 1-continued

| Compound Number (alternative designation) | Compound Structure |
|---|---|
| I-13 | (Cu complex with methylthiourea and ethoxy dithiocarbonate ligands bridged by dimethyl diimine) |
| I-14 (NV30164) | (Ni complex analogous to I-13) |
| I-15 | (Zn complex analogous to I-13) |
| I-16 | (Free ligand: methylthiosemicarbazone / O-ethyl dithiocarbonate of 2,3-butanedione) |
| I-17 | (Cu complex with methylthiourea and methoxy dithiocarbonate ligands) |
| I-18 | (Ni complex with methylthiourea and methoxy dithiocarbonate ligands) |

TABLE 1-continued
| Compound Number (alternative designation) | Compound Structure |
|---|---|
| I-19 | 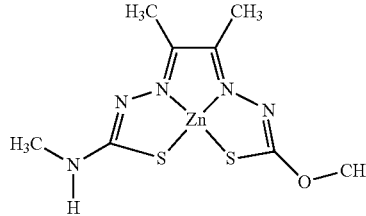 |
| I-20 | 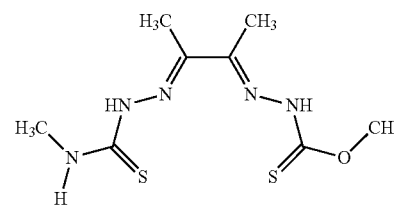 |
| I-21 | 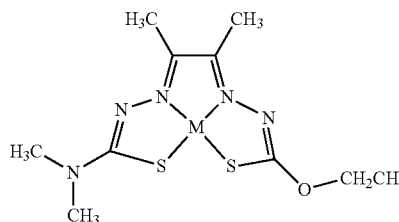 |
| I-22 (MB10014) | 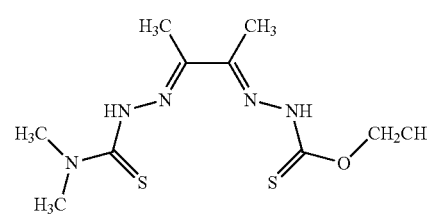 |
| I-23 | 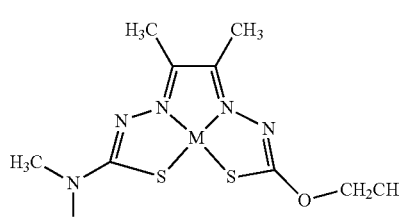 |
| I-24 | 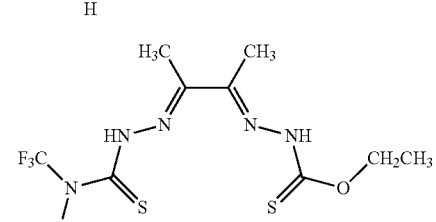 |
| I-25 | 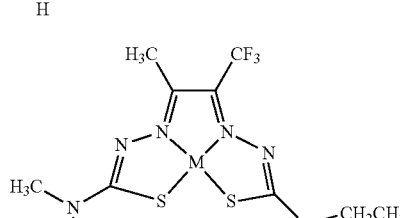 |

TABLE 1-continued

| Compound Number (alternative designation) | Compound Structure |
|---|---|
| I-26 | (structure) |
| I-27 | (structure) |
| I-28 | (structure) |
| I-29 | (structure) |
| I-30 | (structure) |
| I-31 | (structure) |
| I-32 | (structure) |

TABLE 1-continued
| Compound Number (alternative designation) | Compound Structure |
|---|---|
| I-33 | 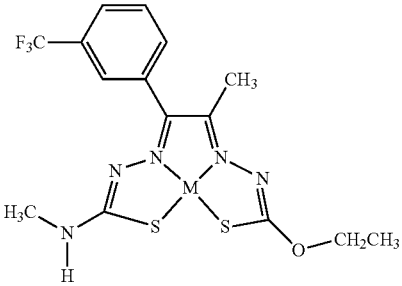 |
| I-34 | 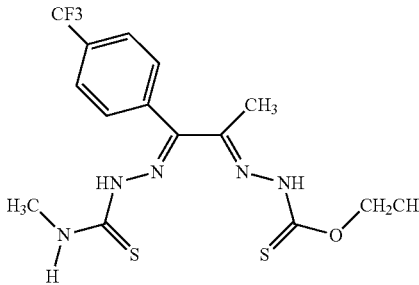 [SMILES: CCOC(=S)N/N=C(C)/C(=N/NC(=S)NC)c1ccc(C(F)(F)F)cc1] |
| I-35 | 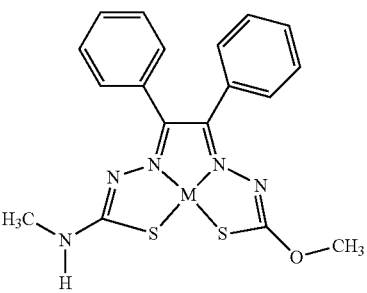 |
| I-36 | 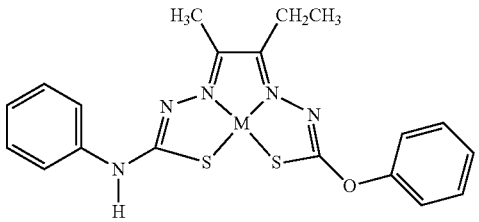 |
| I-37 | 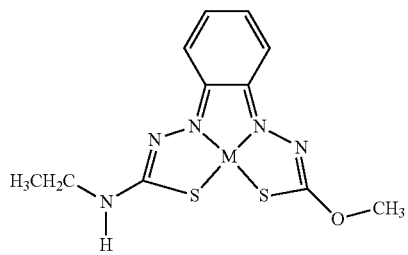 |

TABLE 1-continued

| Compound Number (alternative designation) | Compound Structure |
|---|---|
| I-38 | 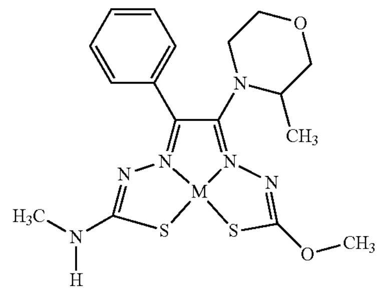 |
| I-39 | 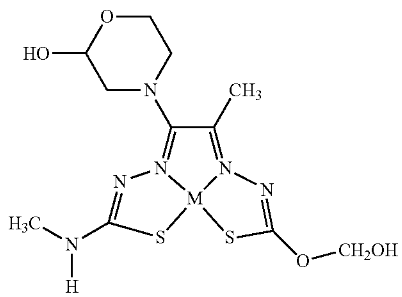 |
| I-40 | 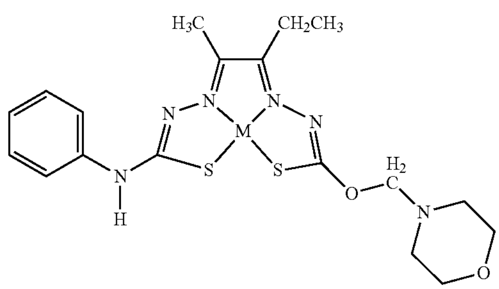 |
| I-41 | 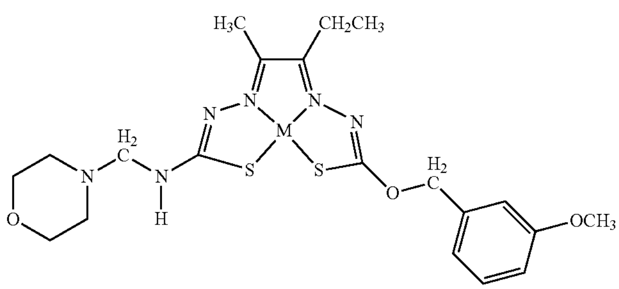 |
| I-42 | 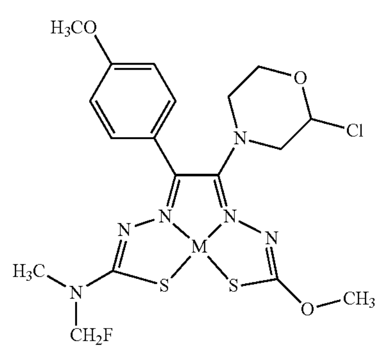 |

TABLE 1-continued

| Compound Number (alternative designation) | Compound Structure |
|---|---|
| I-43 | 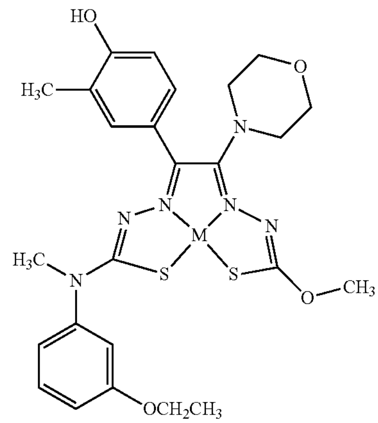 |
| I-44 | 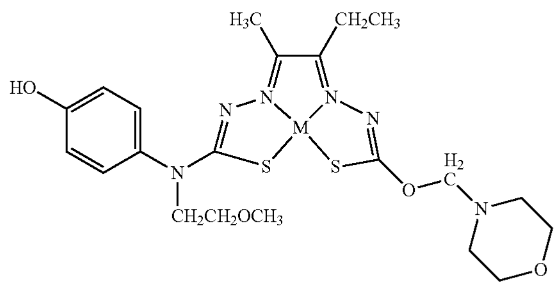 |
| I-45 | 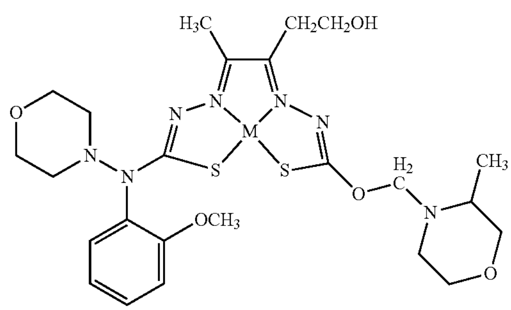 |
| I-46 | 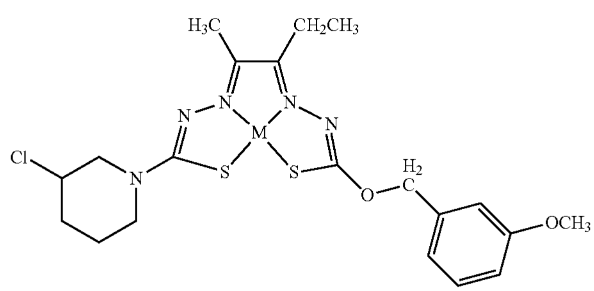 |
| I-47 | 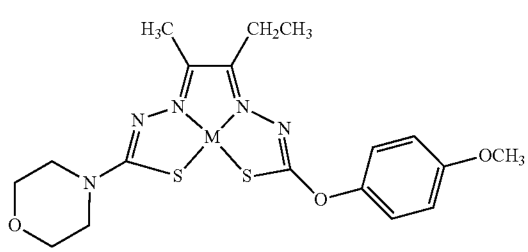 |

TABLE 1-continued

| Compound Number (alternative designation) | Compound Structure |
|---|---|
| I-48 | [Structure: metal complex with M center, methylthiourea and ethoxy-substituted bis-hydrazone ligand with CH_3 and H substituents] |
| I-49 | [Structure: Cu complex with methylthiourea and ethoxy-substituted bis-hydrazone ligand with CH_3 and H substituents] |
| I-50 | [Structure: free ligand, bis-hydrazone with methylthiourea on left and ethoxy thiocarbonate on right, with H and CH_3 on backbone] |
| I-51 | [Structure: metal complex with M center, methylthiourea and ethoxy-substituted bis-hydrazone ligand with H_3C and H substituents (reversed orientation)] |
| I-52 | [Structure: Cu complex with methylthiourea and ethoxy-substituted bis-hydrazone ligand with H_3C and H substituents (reversed orientation)] |
| I-53 | [Structure: free ligand, bis-hydrazone with methylthiourea on left and ethoxy thiocarbonate on right, with H_3C and H on backbone] |

TABLE 1-continued

| Compound Number (alternative designation) | Compound Structure |
|---|---|
| I-54 | 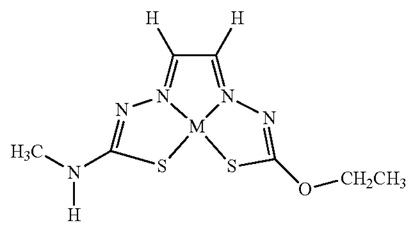 |
| I-55 | 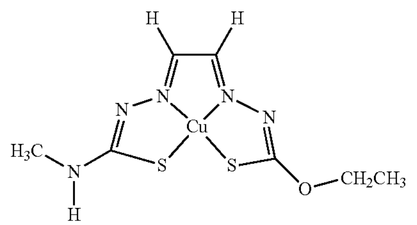 |
| I-56 | 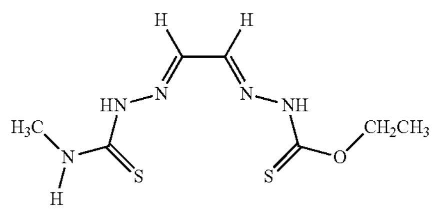 |
| I-57 | 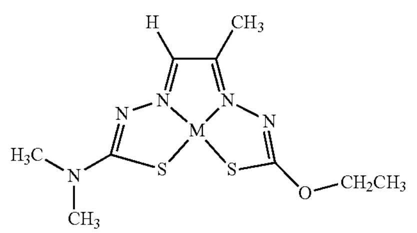 |
| I-58 | 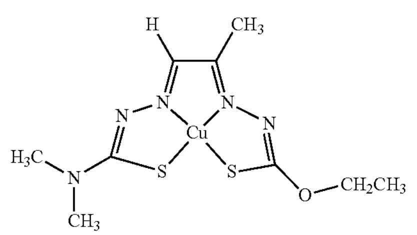 |
| I-59 | 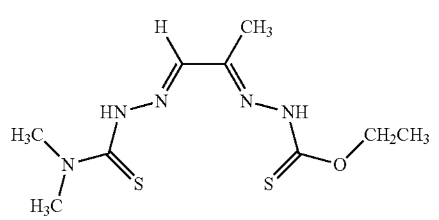 [SMILES: CCOC(=S)N/N=C(C)/C=N/NC(=S)N(C)C] |

TABLE 1-continued

| Compound Number (alternative designation) | Compound Structure |
|---|---|
| I-60 | [Structure: mixed bis(thiosemicarbazonato) metal complex with methyl-substituted backbone; one side N,N-dimethylthiosemicarbazone, other side ethoxy-thiocarbamate; central metal M] |
| I-61 | [Structure: same as I-60 but central metal is Cu] |
| I-62 | [Structure: free ligand form - methyl-substituted diimine backbone with N,N-dimethylthiosemicarbazide on one side and O-ethyl thiocarbamate on the other] |
| I-63 | [Structure: unsubstituted (H,H) backbone bis-complex with N,N-dimethylthiosemicarbazonato on one side, ethoxy-thiocarbamato on the other, central metal M] |
| I-64 | [Structure: same as I-63 but central metal is Cu] |
| I-65 | [Structure: free ligand form with H,H backbone, N,N-dimethylthiosemicarbazide on one side, O-ethyl thiocarbamate on the other] |

TABLE 1-continued
| Compound Number (alternative designation) | Compound Structure |
|---|---|
| I-66 | 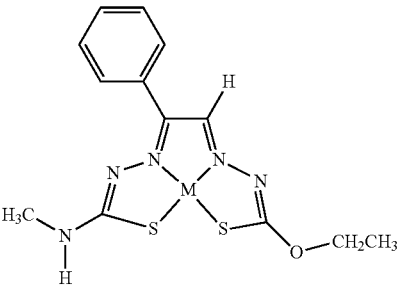 |
| I-67 | 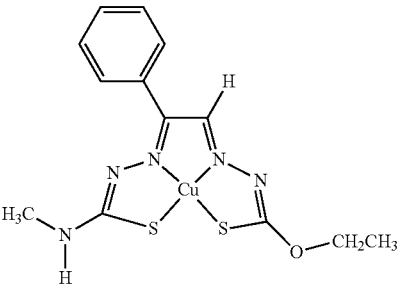 |
| I-68 | 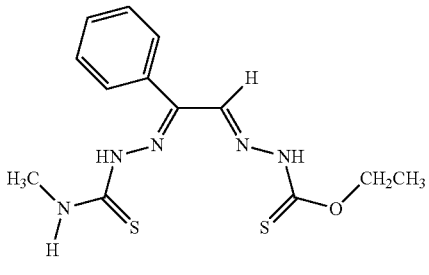 [SMILES: CCOC(=S)N/N=C/C(=N/NC(=S)NC)c1ccccc1] |
| I-69 | 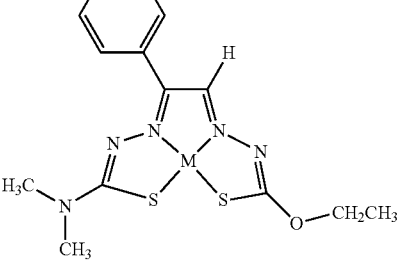 |
| I-70 | 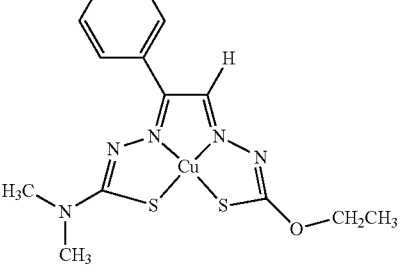 |

TABLE 1-continued

| Compound Number (alternative designation) | Compound Structure |
|---|---|
| I-71 | (structure: phenyl-C(=N-NH-C(=S)-N(CH3)2)-CH=N-NH-C(=S)-O-CH2CH3) |
| I-72 | (Cu complex of bis(thiosemicarbazone)-type ligand with phenyl, CH3 substituents; one side NHCH3, other side OCH2CH3) |
| I-73 | (Ni complex, analogous to I-72) |
| I-74 | (Zn complex, analogous to I-72) |
| I-75 | (structure: phenyl-C(=N-NH-C(=S)-NHCH3)-C(CH3)=N-NH-C(=S)-O-CH2CH3) |

TABLE 1-continued

| Compound Number (alternative designation) | Compound Structure |
|---|---|
| I-76 | (structure) |
| I-77 | (structure) |
| I-78 | (structure) |
| I-79 | (structure) |
| I-80 | (structure) |

TABLE 1-continued

| Compound Number (alternative designation) | Compound Structure |
|---|---|
| I-81 | 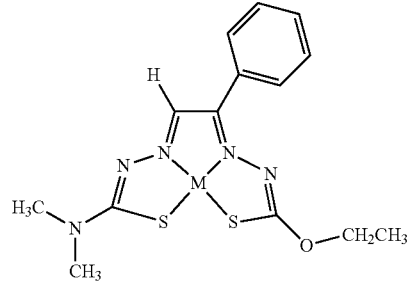 |
| I-82 | 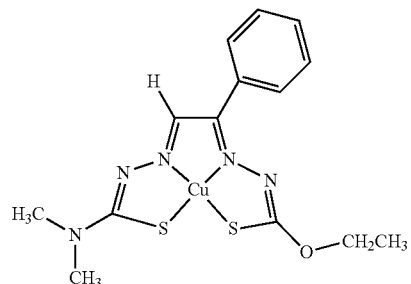 |
| I-83 | 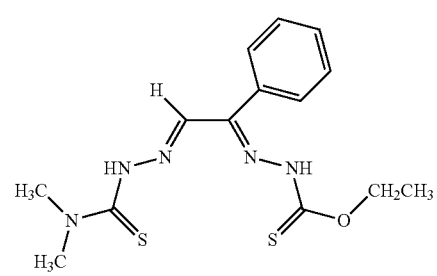 [SMILES: CCOC(=S)N/N=C(/C=N/NC(=S)N(C)C)c1ccccc1] |

In some embodiments, one or more of compounds I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-53, I-54, I-55, I-56, I-57, I-58, I-59, I-60, I-61, I-62, I-63, I-64, I-65, I-66, I-67, I-68, I-69, I-70, I-71, I-72, I-73, I-74, I-75, I-76, I-77, I-78, I-79, I-80, I-81, I-82, or I-83 are excluded from the compounds of the invention (e.g., Formula (I)).

In some embodiments, one or more of compounds I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-53, I-54, I-55, I-56, I-57, I-58, I-59, I-60, I-61, I-62, I-63, I-64, I-65, I-66, I-67, I-68, I-69, I-70, or 1-71 are excluded from the compounds of the invention (e.g., Formula (I)).

In some embodiments, the compounds of the invention include one or more of I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-53, I-54, I-55, I-56, I-57, I-58, I-59, I-60, I-61, I-62, I-63, I-64, I-65, I-66, I-67, I-68, I-69, I-70, I-71, I-72, I-73, I-74, I-75, I-76, I-77, I-78, I-79, I-80, I-81, I-82, or I-83. In some embodiments, the compounds of the invention include one or more of I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-53, I-54, I-55, I-56, I-57, I-58, I-59, I-60, I-61, I-62, I-63, I-64, I-65, I-66, I-67, I-68, I-69, I-70, or I-71. In some embodiments, the compounds of the invention include one or more of I-1, I-3, I-4, I-5, I-7, I-8, I-9, I-11, I-12, or I-22. In some embodiments, the compounds of the invention include one or more of I-1, I-3, I-4, I-5, I-7, I-8, I-9, I-11, I-12, I-22, I-49, I-52, I-55, I-58, I-61, I-64, I-67, or I-70. In some embodiments, the compounds of the invention include one or more of I-1, I-3, I-4, I-5, I-7, I-8, I-9, I-11, I-12, I-22, I-49, or I-52. In some embodiments, the compounds of the invention include one or more of I-1 or I-5. In some embodiments, the compounds of the invention include one or more of I-1, I-5, I-49, or I-52.

In some embodiments, the compounds of the invention include I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-53, I-54, I-55, I-56, I-57, I-58, I-59, I-60, I-61, I-62, I-63, I-64, I-65, I-66, I-67, I-68, I-69, I-70, I-71, I-72, I-73, I-74, I-75, I-76, I-77, I-78, I-79, I-80, I-81, I-82, and I-83. In some embodiments, the compounds of the invention include I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-53, I-54, I-55, I-56, I-57, I-58, I-59, I-60, I-61, I-62, I-63, I-64, I-65, I-66, I-67, I-68, I-69, I-70, and I-71. In some embodiments, the compounds of the invention include I-1, I-3, I-4, I-5, I-7, I-8, I-9, I-11, I-12, and I-22. In some embodiments, the compounds of the invention include I-1, I-3, I-4, I-5, I-7, I-8, I-9, I-11, I-12, I-22, I-49, I-52, I-55, I-58, I-61, I-64, I-67, and I-70. In some embodiments, the compounds of the invention include I-1, I-3, I-4, I-5, I-7, I-8, I-9, I-11, I-12, I-22, I-49, and I-52. In some embodiments, the compounds of the invention include I-1 and I-5. In some embodiments, the compounds of the invention include I-1, I-5, I-49, and I-52.

In some embodiments, one or more (e.g., one, two, three, four, five, or six) of the following apply to Formula (I): $R^{1a}$ is H, $R^{1b}$ is methyl, $R^2$ is ethyl, $R^3$ is methyl, $R^4$ is methyl, or M is Cu. In some embodiments, one or more (e.g., one, two, three, four, five, or six) of the following apply to Formula (I): $R^{1a}$ is methyl, $R^{1b}$ is H, $R^2$ is ethyl, $R^3$ is methyl, $R^4$ is methyl, or M is Cu. In some embodiments, one or more (e.g., one, two, three, four, five, or six) of the following apply to Formula (I): $R^{1a}$ is H, $R^{1b}$ is methyl, $R^2$ is ethyl, $R^3$ is methyl, $R^4$ is methyl, or M is Zn. In some embodiments, one or more (e.g., one, two, three, four, five, or six) of the following apply to Formula (I): $R^{1a}$ is methyl, $R^{1b}$ is H, $R^2$ is ethyl, $R^3$ is methyl, $R^4$ is methyl, or M is Zn.

In some embodiments, one or more (e.g., one, two, three, four, five, or six) of the following apply to Formula (I): $R^{1a}$ is H, $R^{1b}$ is methyl, $R^2$ is ethyl, $R^3$ is phenyl, $R^4$ is methyl, or M is Cu. In some embodiments, one or more (e.g., one, two, three, four, five, or six) of the following apply to Formula (I): $R^{1a}$ is methyl, $R^{1b}$ is H, $R^2$ is ethyl, $R^3$ is phenyl, $R^4$ is methyl, or M is Cu. In some embodiments, one or more (e.g., one, two, three, four, five, or six) of the following apply to Formula (I): $R^{1a}$ is H, $R^{1b}$ is methyl, $R^2$ is ethyl, $R^3$ is phenyl, $R^4$ is methyl, or M is Zn. In some embodiments, one or more (e.g., one, two, three, four, five, or six) of the following apply to Formula (I): $R^{1a}$ is methyl, $R^{1b}$ is H, $R^2$ is ethyl, $R^3$ is phenyl, $R^4$ is methyl, or M is Zn.

In some embodiments, one or more (e.g., one, two, three, four, five, or six) of the following apply to Formula (I): $R^{1a}$ is H, $R^{1b}$ is methyl, $R^2$ is ethyl, $R^3$ is methyl, $R^4$ is phenyl, or M is Cu. In some embodiments, one or more (e.g., one, two, three, four, five, or six) of the following apply to Formula (I): $R^{1a}$ is methyl, $R^{1b}$ is H, $R^2$ is ethyl, $R^3$ is methyl, $R^4$ is phenyl, or M is Cu. In some embodiments, one or more (e.g., one, two, three, four, five, or six) of the following apply to Formula (I): $R^{1a}$ is H, $R^{1b}$ is methyl, $R^2$ is ethyl, $R^3$ is methyl, $R^4$ is phenyl, or M is Zn. In some embodiments, one or more (e.g., one, two, three, four, five, or six) of the following apply to Formula (I): $R^{1a}$ is methyl, $R^{1b}$ is H, $R^2$ is ethyl, $R^3$ is methyl, $R^4$ is phenyl, or M is Zn.

In some embodiments, $R^{1a}$ is H, $R^{1b}$ is H, or both. In other embodiments, $R^{1a}$ is H or $R^{1b}$ is H, but both $R^{1a}$ and $R^{1b}$ are not H. In some embodiments, $R^{1a}$ is H. In some embodiments, $R^{1b}$ is H. In some embodiments, $R^{1a}$ is H and $R^{1b}$ is methyl. In some embodiments, $R^{1a}$ is methyl and $R^{1b}$ is H. In some embodiments, $R^{1a}$ is methyl and $R^{1b}$ is methyl. In some embodiments, $R^2$ is H, methyl, or ethyl. In some embodiments, $R^2$ is ethyl. In some embodiments, $R^3$ is H, methyl, or phenyl. In some embodiments, $R^3$ is methyl or phenyl. In some embodiments, $R^3$ is methyl. In some embodiments, $R^3$ is H. In some embodiments, $R^4$ is H, methyl, or phenyl. In some embodiments, $R^4$ is methyl or phenyl. In some embodiments, $R^4$ is methyl. In some embodiments, $R^4$ is H.

In some embodiments, the compounds of Formula (I) (e.g., (e.g., Formula (Ia), (Ib), I-1, I-2, I-3, I-4, I-5, I-6, I-7, or I-8)) can be in the form of salts, optical and geometric isomers, and salts of isomers. In other embodiments, the compounds can be in various forms, such as uncharged molecules, components of molecular complexes, or non-irritating pharmacologically acceptable salts, including but not limited to hydrochloride, hydrobromide, sulphate, phosphate, nitrate, borate, acetate, maleate, tartrate, and salicylate. In some instances, for acidic compounds, salts can include metals, amines, or organic cations (e.g. quaternary ammonium). In yet other embodiments, derivatives of the compounds (e.g., ethers, esters, or amides) which have desirable retention and release characteristics, but which are hydrolyzed (e.g., easily hydrolyzed) by body pH, enzymes, or other suitable means, can be employed.

In some embodiments, the compounds of the invention having a chiral center and can exist in and be isolated in optically active and racemic forms. In other embodiments, compounds may exhibit polymorphism. Some embodiments of the present invention encompass any racemic, optically active, polymorphic, or stereoisomeric form, or mixtures thereof, of a compound described herein. The preparation of optically active forms can be accomplished by any suitable method, including but not limited to, resolution of the racemic form by recrystallization techniques, synthesis from optically-active starting materials, chiral synthesis, or chromatographic separation using a chiral stationary phase.

In other embodiments, compounds of the invention encompass Formula (I) and salts, optical isomers, geometric isomers, salts of isomers, and derivatives thereof. In yet other embodiments, compounds of the invention encompass Formula (Ia) and salts, optical isomers, geometric isomers, salts of isomers, and derivatives thereof. In still other embodiments, compounds of the invention encompass Formula (Ib) and salts, optical isomers, geometric isomers, salts of isomers, and derivatives thereof.

In some embodiments, the compounds of the invention (e.g., Formula (I), (Ia), (Ib), I-1, I-3, I-4, I-5, I-7, I-8, I-9, I-11, I-12, or I-22) do not use cellular production of Reactive Oxygen Species (ROS) to kill the cell or decrease the cell viability. In some embodiments, the compounds of the invention (e.g., Formula (I), (Ia), (Ib), I-1, I-3, I-4, I-5, I-7, I-8, I-9, I-11, I-12, or I-22) use a mechanism to kill the cell or decrease the cell viability that is different than the mechanism for increasing production of ROS in the cells. In some embodiments, a compound from Formula (Ib) can combine with a divalent metal (e.g., Cu or Zn) (e.g., in the composition or the pharmaceutical composition) to form a compound from Formula (Ia). In some embodiments, a compound from Formula (Ib) can combine with a divalent metal (e.g., Cu or Zn) that is endogenous to an animal to form a compound from Formula (Ia). In certain embodiments, a compound from Formula (Ia) can switch divalent metals (e.g., transmetalation) in the composition or the pharmaceutical composition to form a compound from Formula (Ia) that has a different divalent metal. For example, in some embodiments, a Cu can replace the Zn in compound I-3, so that compound I-3 becomes compound I-1. In other embodiments, a compound from Formula (Ia) can switch divalent metals (e.g., transmetalation) and the divalent metal that replaces the previous divalent metal is endogenous to the animal. In the example above, Cu would be endogenous to the animal.

In certain embodiments, one or more compounds of the invention (e.g., Formula (I), (Ia), (Ib), I-1, I-3, I-4, I-5, I-7, I-8, I-9, I-11, I-12, or I-22) can be part of a composition and can be in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, or no more than about 99.99%, from about 0.0001% to about 99%, from about 0.0001% to about 50%, from about 0.01% to about 95%, from about 1% to about 95%, from about 10% to about 90%, or from about 25% to about 75%.

In some embodiments, one or more compounds of the invention (e.g., Formula (I), (Ia), (Ib), I-1, I-3, I-4, I-5, I-7, I-8, I-9, I-11, I-12, or I-22) can be purified or isolated in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.0001% to about 99%, from about 0.0001% to about 50%, from about 0.01% to about 95%, from about 1% to about 95%, from about 10% to about 90%, or from about 25% to about 75%.

Some embodiments of the present invention include compositions comprising one or more compounds of the invention (e.g., Formula (I), (Ia), (Ib), I-1, I-3, I-4, I-5, I-7, I-8, I-9, I-11, I-12, or I-22). In certain embodiments, the composition is a pharmaceutical composition, such as compositions that are suitable for administration to animals (e.g., mammals, primates, monkeys, humans, canine, feline, porcine, mice, rabbits, or rats). In some instances, the pharmaceutical composition is non-toxic, does not cause side effects, or both. In some embodiments, there may be inherent side effects (e.g., it may harm the patient or may be toxic or harmful to some degree in some patients).

"Therapeutically effective amount" means an amount effective to achieve a desired and/or beneficial effect. An effective amount can be administered in one or more administrations. For some purposes of this invention, a therapeutically effective amount is an amount appropriate to treat an indication. By treating an indication is meant achieving any desirable effect, such as one or more of palliate, ameliorate, stabilize, reverse, slow, or delay disease progression, increase the quality of life, or to prolong life. Such achievement can be measured by any suitable method, such as measurement of tumor size.

In certain embodiments, one or more compounds of the invention (e.g., Formula (I), (Ia), (Ib), I-1, I-3, I-4, I-5, I-7, I-8, I-9, I-11, I-12, or I-22) can be part of a pharmaceutical composition and can be in an amount of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.001% to about 99%, from about 0.001% to about 50%, from about 0.1% to about 99%, from about 1% to about 95%, from about 10% to about 90%, or from about 25% to about 75%. In some embodiments, the pharmaceutical composition can be presented in a dosage form which is suitable for the topical, subcutaneous, intrathecal, intraperitoneal, oral, parenteral, rectal, cutaneous, nasal, vaginal, or ocular administration route. In other embodiments, the pharmaceutical composition can be presented in a dosage form which is suitable for parenteral administration, a mucosal administration, intravenous administration, subcutaneous administration, topical administration, intradermal administration, oral administration, sublingual administration, intranasal administration, or intramuscular administration. The pharmaceutical composition can be in the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols or other suitable forms.

In some embodiments, the pharmaceutical composition can include one or more formulary ingredients. A "formulary ingredient" can be any suitable ingredient (e.g., suitable for the drug(s), for the dosage of the drug(s), for the timing of release of the drugs(s), for the disease, for the disease state, or for the delivery route) including, but not limited to, water (e.g., boiled water, distilled water, filtered water, pyrogen-free water, or water with chloroform), sugar (e.g., sucrose, glucose, mannitol, sorbitol, xylitol, or syrups made therefrom), ethanol, glycerol, glycols (e.g., propylene glycol), acetone, ethers, DMSO, surfactants (e.g., anionic surfactants, cationic surfactants, zwitterionic surfactants, or nonionic surfactants (e.g., polysorbates)), oils (e.g., animal oils, plant oils (e.g., coconut oil or *arachis* oil), or mineral oils), oil derivatives (e.g., ethyl oleate, glyceryl monostearate, or hydrogenated glycerides), excipients, preservatives (e.g., cysteine, methionine, antioxidants (e.g., vitamins (e.g., A, E, or C), selenium, retinyl palmitate, sodium citrate, citric acid, chloroform, or parabens, (e.g., methyl paraben or propyl paraben)), or combinations thereof.

In certain embodiments, pharmaceutical compositions can be formulated to release the active ingredient (e.g., one or more compounds of the invention such as Formula (I), (Ia), (Ib), I-1, I-2, I-3, I-4, I-5, I-6, I-7, or I-8) substantially immediately upon the administration or any substantially predetermined time or time after administration. Such formulations can include, for example, controlled release formulations such as various controlled release compositions and coatings.

Other formulations (e.g., formulations of a pharmaceutical composition) can, in certain embodiments, include those incorporating the drug (or control release formulation) into food, food stuffs, feed, or drink.

In some embodiments, a compound from Formula (Ib) can combine with a divalent metal (e.g., Cu or Zn) in the composition or the pharmaceutical composition to form a compound from Formula (Ia). In some embodiments, a compound from Formula (Ib) can combine with a divalent metal (e.g., Cu or Zn) that is endogenous to the animal to form a compound from Formula (Ia).

In certain embodiments, a compound from Formula (Ia) can switch divalent metals (e.g., transmetalation) in the composition or the pharmaceutical composition to form a compound from Formula (Ia) that has a different divalent metal. For example, in some embodiments, a Cu can replace the Zn in compound I-3, so that compound I-3 becomes compound I-1. In other embodiments, a compound from Formula (Ia) can switch divalent metals (e.g., transmetalation) and the divalent metal that replaces the previous divalent metal is endogenous to the animal. In the example above, Cu would be endogenous to the animal.

Other embodiments of the invention can include methods of administering or treating an organism, which can involve treatment with an amount of at least one compound of the invention (e.g., Formula (I), (Ia), (Ib), I-1, I-3, I-4, I-5, I-7, I-8, I-9, I-11, I-12, or I-22) that is effective to treat the disease, condition, or disorder that the organism has, or is suspected of having, or is susceptible to, or to bring about a desired physiological effect. In some embodiments, the composition or pharmaceutical composition comprises at least one compound of the invention (e.g., Formula (I), (Ia), (Ib), I-1, I-3, I-4, I-5, I-7, I-8, I-9, I-11, I-12, or I-22) which can be administered to an animal (e.g., mammals, primates, monkeys, or humans) in an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some conditions, the dosage can be about 0.5 mg/kg human body weight or about 6.5 mg/kg human body weight. In some instances, some animals (e.g., mammals, mice, rabbits, feline, porcine, or canine) can be administered a dosage of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. Of course, those skilled in the art will appreciate that it is possible to employ many concentrations in the methods of the present invention, and using, in part, the guidance provided herein, will be able to adjust and test any number of concentrations in order to find one that achieves the desired result in a given circumstance. In other embodiments, the compounds of the invention (e.g., Formula (I), (Ia), (Ib), I-1, I-3, I-4, I-5, I-7, I-8, I-9, I-11, I-12, or I-22) can be administered in combination with one or more other therapeutic agents for a given disease, condition, or disorder.

In some embodiments, the compositions can include a unit dose of one or more compounds of the invention (e.g., Formula (I), (Ia), (Ib), I-1, I-3, I-4, I-5, I-7, I-8, I-9, I-11, I-12, or I-22) in combination with a pharmaceutically acceptable carrier and, in addition, can include other medicinal agents, pharmaceutical agents, carriers, adjuvants, diluents, and excipients. In certain embodiments, the carrier, vehicle or excipient can facilitate administration, delivery and/or improve preservation of the composition. In other embodiments, the one or more carriers, include but are not limited to, saline solutions such as normal saline, Ringer's solution, PBS (phosphate-buffered saline), and generally mixtures of various salts including potassium and phosphate salts with or without sugar additives such as glucose. Carriers can include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents. In other embodiments, the one or more excipients can include, but are not limited to water, saline, dextrose, glycerol, ethanol, or the like, and combinations thereof. Nontoxic auxiliary substances, such as wetting agents, buffers, or emulsifiers may also be added to the composition. Oral formulations can include such normally employed excipients as, for example, pharmaceutical grades of mannitol, lactose, starch, magnesium stearate, sodium saccharine, cellulose, and magnesium carbonate.

Administration Routes and Treatments of Disease

The compounds of the invention (e.g., Formula (I), (Ia), (Ib), I-1, I-3, I-4, I-5, I-7, I-8, I-9, I-11, I-12, or I-22) can be administered to animals by any number of suitable administration routes or formulations. The compounds of the invention (e.g., Formula (I), (Ia), (Ib), I-1, I-3, I-4, I-5, I-7, I-8, I-9, I-11, I-12, or I-22) can also be used to treat animals for a variety of diseases. Animals include but are not limited to mammals, primates, monkeys (e.g., macaque, rhesus macaque, or pig tail macaque), humans, canine, feline, bovine, porcine, avian (e.g., chicken), mice, rabbits, and rats. As used herein, the term "subject" refers to both human and animal subjects.

The route of administration of the compounds of the invention (e.g., Formula (I), (Ia), (Ib), I-1, I-3, I-4, I-5, I-7, I-8, I-9, I-11, I-12, or I-22) can be of any suitable route. Administration routes can be, but are not limited to the oral route, the parenteral route, the cutaneous route, the nasal route, the rectal route, the vaginal route, and the ocular route. In other embodiments, administration routes can be parenteral administration, a mucosal administration, intravenous administration, subcutaneous administration, topical administration, intradermal administration, oral administration, sublingual administration, intranasal administration, or intramuscular administration. The choice of administration route can depend on the compound identity (e.g., the physical and chemical properties of the compound) as well as the age and weight of the animal, the particular disease (e.g., cancer), and the severity of the disease (e.g., stage or severity of cancer). Of course, combinations of administration routes can be administered, as desired.

Some embodiments of the invention include a method for providing a subject with a composition comprising one or more compounds of the invention (e.g., Formula (I), (Ia), (Ib), I-1, I-3, I-4, I-5, I-7, I-8, I-9, I-11, I-12, or I-22) described herein (e.g., a pharmaceutical composition) which comprises one or more administrations of one or more such compositions; the compositions may be the same or different if there is more than one administration. In some embodiments, a compound from Formula (Ib) can combine with a divalent metal (e.g., Cu or Zn) to form a compound from Formula (Ia). In some embodiments, a compound from Formula (Ib) can combine with a divalent metal (e.g., Cu or Zn) that is endogenous to the animal to form a compound from Formula (Ia). In certain embodiments, a compound from Formula (Ia) can switch divalent metals (e.g., transmetalation) in the composition or the pharmaceutical composition to form a compound from Formula (Ia) that has a different divalent metal. For example, in some embodiments, a Cu can replace the Zn in compound I-3, so that compound I-3 becomes compound I-1. In other embodiments, a compound from Formula (Ia) can switch divalent metals (e.g., transmetalation) and the divalent metal that replaces the previous divalent metal is endogenous to the animal. In the example above, Cu would be endogenous to the animal.

Diseases that can be treated in an animal (e.g., mammals, porcine, canine, avian (e.g., chicken), bovine, feline, primates, rodents, monkeys, rabbits, mice, rats, and humans) using a compound of the invention (e.g., Formula (I), (Ia), (Ib), I-1, I-3, I-4, I-5, I-7, I-8, I-9, I-11, I-12, or I-22) include, but are not limited to cancers.

In some embodiments, cancers that can be treated in an animal (e.g., mammals, porcine, canine, avian (e.g., chicken), bovine, feline, primates, rodents, monkeys, rabbits, mice, rats, and humans) using a compound of the invention (e.g., Formula (I), (Ia), (Ib), I-1, I-3, I-4, I-5, I-7, I-8, I-9, I-11, I-12, or I-22) include, but are not limited to, acute lymphoblastic leukemia, astrocytoma, basal cell carcinoma, bladder cancer, bone marrow cancer, breast cancer, chronic lymphocytic leukemia (CLL), CNS cancer (e.g., glioblastoma, glioblastoma multiforme, gliosarcoma, or astrocytoma), colon cancer, colorectal cancer (e.g., colon cancer or rectal cancer), endometrial cancer, gastric cancer, glioblastoma, glioblastoma multiforme, glioma, gliosarcoma, hepatocellular carcinoma, kidney cancer (e.g., renal cancer), leukemia, liver cancer, lung cancer (e.g., non-small cell lung cancer), lymphoma, melanoma (e.g., cutaneous malignant melanoma or melanoma tumorigenesis), malignant nerve sheath tumors, medulloblastoma, meningioma, multiple myeloma, nasopharyngeal carcinoma, neuroblastoma, non-Hodgkin lymphoma (e.g., diffuse large B-cell lymphoma), non-small cell lung cancer, oral cancer, ovarian cancer, pancreatic cancer (e.g., pancreatic ductal adenocarcinoma), prostate cancer, rectal cancer, renal cancer, renal cell carcinoma, rhabdomyosarcoma, squamous cell carcinoma (e.g., head and neck squamous cell carcinoma), stomach cancer, thyroid cancer, uterine cancer, cancers that can result in metastasis, cancers resulting from metastasis, or cancerous tumors thereof. In some embodiments, cancers that can be treated do not include leukemia. In some embodiments, cancers that can be treated include, but are not limited to, basal cell carcinoma, bladder cancer, bone marrow cancer, breast cancer, CNS cancer (e.g., glioblastoma, glioblastoma multiforme, gliosarcoma, or astrocytoma), colon cancer, colorectal cancer (e.g., colon cancer or rectal cancer), endometrial cancer, gastric cancer, glioblastoma, glioblastoma multiforme, glioma, gliosarcoma, hepatocellular carcinoma, kidney cancer (e.g., renal cancer), liver cancer, lung cancer (e.g., non-small cell lung cancer), lymphoma, melanoma (e.g., cutaneous malignant melanoma or melanoma tumorigenesis), malignant nerve sheath tumors, medulloblastoma, meningioma, multiple myeloma, nasopharyngeal carcinoma, neuroblastoma, non-Hodgkin lymphoma (e.g., diffuse large B-cell lymphoma), non-small cell lung cancer, oral cancer, ovarian cancer, pancreatic cancer (e.g., pancreatic ductal adenocarcinoma), prostate cancer, rectal cancer, renal cell carcinoma, rhabdomyosarcoma, squamous cell carcinoma (e.g., head and neck squamous cell carcinoma), stomach cancer, thyroid cancer, uterine cancer, cancers that can result in metastasis, cancers resulting from metastasis, or cancerous tumors thereof. In some embodiments, cancers that can be treated include, but are not limited to, leukemia, lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, breast cancer, or cancerous tumors thereof. In some embodiments, cancers that can be treated include, but are not limited to, lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, breast cancer, or cancerous tumors thereof. In some embodiments, cancers that can be treated include, but are not limited to, cancerous tumors. Animals that can be treated include but are not limited to mammals, rodents, primates, monkeys (e.g., macaque, rhesus macaque, pig tail macaque), humans, canine, feline, porcine, avian (e.g., chicken), bovine, mice, rabbits, and rats. As used herein, the term "subject" refers to both human and animal subjects. In some instances, the animal is in need of the treatment (e.g., by showing signs of disease or cancer, or by having a cancerous tumor).

In some embodiments, cancers that can be treated in an animal (e.g., mammals, porcine, canine, avian (e.g., chicken), bovine, feline, primates, rodents, monkeys, rabbits, mice, rats, and humans) using a compound of the invention (e.g., Formula (I), (Ia), (Ib), I-1, I-3, I-4, I-5, I-7, I-8, I-9, I-11, I-12, or I-22) include, but are not limited to cancers that do not use an increase in reactive oxidative species as a mechanism to kill cancer cells.

As used herein, the term "treating" (and its variations, such as "treatment") is to be considered in its broadest context. In particular, the term "treating" does not necessarily imply that an animal is treated until total recovery. Accordingly, "treating" includes amelioration of the symptoms, relief from the symptoms or effects associated with a condition, decrease in severity of a condition, or preventing, preventively ameliorating symptoms, or otherwise reducing the risk of developing a particular condition. As used herein, reference to "treating" an animal includes but is not limited to prophylactic treatment and therapeutic treatment. Any of the compositions (e.g., pharmaceutical compositions) described herein can be used to treat an animal.

As related to treating cancer (e.g., lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, breast cancer, or cancerous tumors thereof), treating can include but is not limited to prophylactic treatment and therapeutic treatment. As such, treatment can include, but is not limited to: preventing cancer (e.g., lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, breast cancer, or cancerous tumors thereof); reducing the risk of cancer (e.g., lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, breast cancer, or cancerous tumors thereof); ameliorating or relieving symptoms of cancer (e.g., lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, breast cancer, or cancerous tumors thereof); eliciting a bodily response against cancer (e.g., lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, breast cancer, or cancerous tumors thereof); inhibiting the development or progression of cancer (e.g., lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, breast cancer, or cancerous tumors thereof); inhibiting or preventing the onset of symptoms associated with cancer (e.g., lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, breast cancer, or cancerous tumors thereof); reducing the severity of cancer (e.g., lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, breast cancer, or cancerous tumors thereof); causing a regression of cancer (e.g., lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, breast cancer, or cancerous tumors thereof) or one or more of the symptoms associated with cancer (e.g., a decrease in tumor size); causing remission of cancer (e.g., lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, breast cancer, or cancerous tumors thereof); or preventing relapse of cancer (e.g., lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, breast cancer, or cancerous tumors thereof). In some embodiments, treating does not include prophylactic treatment of cancer (e.g., preventing or ameliorating future cancer).

Treatment of an animal can occur using any suitable administration method (such as those disclosed herein) and using any suitable amount of a compound of the invention (e.g., Formula (I), (Ia), (Ib), I-1, I-3, I-4, I-5, I-7, I-8, I-9, I-11, I-12, or 1-22). In some embodiments, methods of treatment comprise treating an animal for cancer (e.g., lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, breast cancer, or cancerous tumors thereof). Some embodiments of the invention include a method for treating a subject (e.g., an animal such as a human or primate) with a composition comprising a compound of the invention (e.g., Formula (I), (Ia), (Ib), I-1, I-3, I-4, I-5, I-7, I-8, I-9, I-11, I-12, or I-22) (e.g., a pharmaceutical composition) which comprises one or more administrations of one or more such compositions; the compositions may be the same or different if there is more than one administration.

In some embodiments, the method of treatment includes administering an effective amount of a composition comprising a compound of the invention (e.g., Formula (I), (Ia), (Ib), I-1, I-3, I-4, I-5, I-7, I-8, I-9, I-11, I-12, or I-22). As used herein, the term "effective amount" refers to a dosage or a series of dosages sufficient to affect treatment (e.g., to treat cancer, such as but not limited to lung cancer (e.g., non-small cell lung cancer), colorectal cancer (e.g., colon cancer or rectal cancer), CNS cancer (e.g., glioblastoma, glioblastoma multiforme, gliosarcoma, or astrocytoma), melanoma (e.g., cutaneous malignant melanoma or melanoma tumorigenesis), ovarian cancer, kidney cancer, prostate cancer, breast cancer, or cancerous tumors thereof) in an animal. In some embodiments, an effective amount can encompass a therapeutically effective amount, as disclosed herein. In certain embodiments, an effective amount can vary depending on the subject and the particular treatment being affected. The exact amount that is required can, for example, vary from subject to subject, depending on the age and general condition of the subject, the particular adjuvant being used (if applicable), administration protocol, and the like. As such, the effective amount can, for example, vary based on the particular circumstances, and an appropriate effective amount can be determined in a particular case. An effective amount can, for example, include any dosage or composition amount disclosed herein. In some embodiments, an effective amount of at least one compound of the invention (e.g., Formula (I), (Ia), (Ib), I-1, I-3, I-4, I-5, I-7, I-8, I-9, I-11, I-12, or I-22) (which can be administered to an animal such as mammals, primates, monkeys or humans) can be an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some embodiments, the dosage can be about 0.5 mg/kg human body weight or about 6.5 mg/kg human body weight. In some instances, an effective amount of at least one compound of the invention (e.g., Formula (I), (Ia), (Ib), I-1, I-3, I-4, I-5, I-7, I-8, I-9, I-11, I-12, or I-22) (which can be administered to an animal such as mammals, rodents, mice, rabbits, feline, porcine, or canine) can be an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. In some embodiments, an effective amount of at least one compound of the invention (e.g., Formula (I), (Ia), (Ib), I-1, I-3, I-4, I-5, I-7, I-8, I-9, I-11, I-12, or I-22) (which can be administered to an animal such as mammals, primates, monkeys or humans) can be an amount of about 1 to about 1000 mg/kg body weight, about 5 to about 500 mg/kg body weight, about 10 to about 200 mg/kg body weight, about 25 to about 100 mg/kg body weight, about 1 mg/kg, about 2 mg/kg, about 5 mg/kg, about 10 mg/kg, about 25 mg/kg, about 50 mg/kg, about 100 mg/kg, about 150 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg. In regard to some conditions, the dosage can be about 20 mg/kg human body weight or about 100 mg/kg human body weight. In some instances, an effective amount of at least one compound of the invention (e.g., Formula (I), (Ia), (Ib), I-1, I-3, I-4, I-5, I-7, I-8, I-9, I-11, I-12, or I-22) (which can be administered to an animal such as mammals, rodents, mice, rabbits, feline, porcine, or canine) can be an amount of about 1 to about 1000 mg/kg body weight, about 5 to about 500 mg/kg body weight, about 10 to about 200 mg/kg body weight, about 25 to about 100 mg/kg body weight, about 1 mg/kg, about 2 mg/kg, about 5 mg/kg, about 10 mg/kg, about 25 mg/kg, about 50 mg/kg, about 100 mg/kg, about 150 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg.

"Therapeutically effective amount" means an amount effective to achieve a desired and/or beneficial effect (e.g., decreasing tumor size). A therapeutically effective amount can be administered in one or more administrations. For some purposes of this invention, a therapeutically effective amount is an amount appropriate to treat an indication (e.g., to treat cancer). By treating an indication is meant achieving any desirable effect, such as one or more of palliate, ameliorate, stabilize, reverse, slow, or delay disease (e.g., cancer) progression, increase the quality of life, or to prolong life. Such achievement can be measured by any suitable method, such as but not limited to measurement of tumor size.

In some embodiments, the treatments can also include one or more of surgical intervention, chemotherapy, radiation therapy, hormone therapies, immunotherapy, and adjuvant systematic therapies. Adjuvants may include but are not limited to chemotherapy (e.g., temozolomide), radiation therapy, antiangiogenic therapy (e.g., bevacizumab), and hormone therapies, such as administration of LHRH agonists; antiestrogens, such as tamoxifen; high-dose progestogens; aromatase inhibitors; and/or adrenalectomy. Chemotherapy can be used as a single-agent or as a combination with known or new therapies.

In some embodiments, the administration of at least one compound of the invention (e.g., Formula (I), (Ia), (Ib), I-1, I-3, I-4, I-5, I-7, I-8, I-9, I-11, I-12, or I-22) is an adjuvant cancer therapy or part of an adjuvant cancer therapy. Adjuvant treatments include treatments by the mechanisms disclosed herein and of cancers as disclosed herein, including, but not limited to tumors. Corresponding primary therapies can include, but are not limited to, surgery, chemotherapy, or radiation therapy. In some instances, the adjuvant treatment can be a combination of chemokine receptor antagonists with traditional chemotoxic agents or with immunotherapy that increases the specificity of treatment to the cancer and potentially limits additional systemic side effects. In still other embodiments, a compound of the invention (e.g., Formula (I), (Ia), (Ib), I-1, I-3, I-4, I-5, I-7, I-8, I-9, I-11, I-12, or I-22) can be used as adjuvant with other chemotherapeutic agents. The use of a compound of the invention (e.g., Formula (I), (Ia), (Ib), I-1, I-3, I-4, I-5, I-7, I-8, I-9, I-11, I-12, or 1-22) can, in some instances, reduce the duration of the dose of both drugs and drug combinations reducing the side effects.

In some embodiments, the treatments disclosed herein can include use of other drugs (e.g., antibiotics) or therapies for treating disease. For example, antibiotics can be used to treat infections and can be combined with a compound of the invention to treat disease (e.g., infections associated with cancer). In other embodiments, intravenous immunoglobulin (IVIG) therapy can be used as part of the treatment regime (i.e., in addition to administration of the compound(s) of the invention).

Methods for Preparing Compounds of Formula (I)

Some embodiments of the present invention include methods for the preparation of compounds of Formula (I). The compounds of Formula (I) can be prepared using any suitable method. In certain embodiments, a compound of Formula (I) can be prepared comprising the step of reacting a compound of Formula (II) with a compound of Formula (III) to result in Formula (IV), which is later made into Formula (I) (e.g., using one or more synthetic steps).

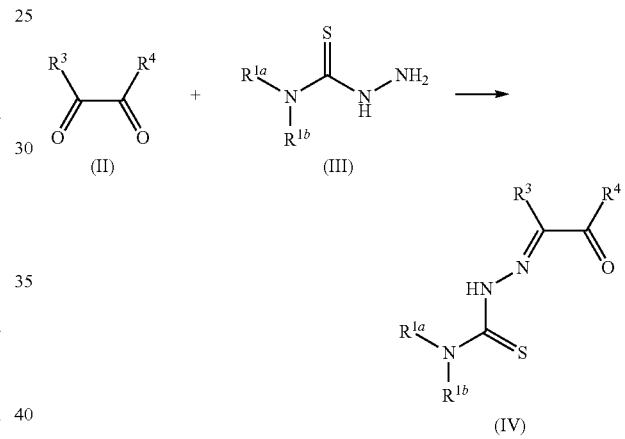

$R^{1a}$, $R^{1b}$, $R^3$, and $R^4$ of Formulas (II), (III), and (IV) are the same as that defined in Formula (I). Formula (II) can be prepared using any suitable method or can be purchased if available. Formula (III) can be prepared using any suitable method or can be purchased where available.

In some embodiments, Formula (II) can be reacted with Formula (III) under the following conditions: Formula (II) can be mixed with an acid (e.g., sulfuric acid) and Formula (III) can be dissolved in a solvent (e.g., water). The mixtures can be added to one another (e.g., by dropwise addition). Formula (IV) can then optionally be recovered using any suitable method.

In some embodiments, Formula (II) (e.g., 2.5 mL, 0.0285 mol) is mixed with concentrated sulfuric acid (e.g., 6 drops) and Formula (III) (e.g., 1.0 g, 0.0095 mol) is dissolved in water (e.g., 6 mL). Formula (III) can be added dropwise to Formula (II) (e.g., at a drop rate of 1 drop per 3 seconds) with stirring (e.g., vigorous stirring). The solution can optionally be placed under vacuum. The solution (e.g., after being placed in a vacuum) can optionally be placed in a freezer (e.g., overnight) which can in some instances result in a solid. Formula (IV) can be recovered (e.g., via filtration with an optional wash (e.g., washed one or more times with water, ethanol, or water/ethanol mixture)).

In some embodiments, Formula (IV) can be reacted with Formula (V) to provide Formula (Ib).

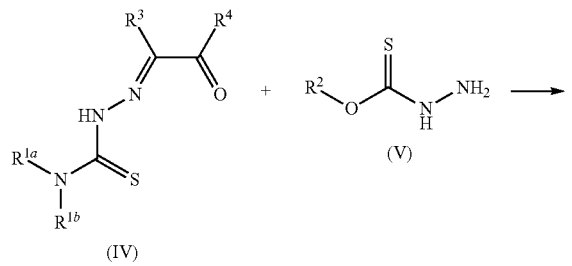

(IV)

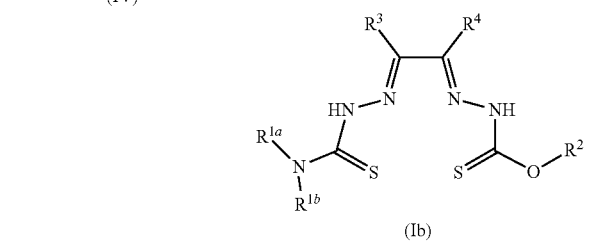

(Ib)

$R^{1a}$, $R^{1b}$, $R^2$, $R^3$, and $R^4$ of Formulas (IV) and (V) are the same as that defined in Formula (I). Formula (IV) can be prepared using any suitable method (e.g., see above) or can be purchased if available. Formula (V) can be prepared using any suitable method or can be purchased if available.

In some embodiments, Formula (IV) can be reacted with Formula (V) to provide Formula (Ib) under the following conditions: Formula (IV) can be suspended in a solvent (e.g., ethanol). Formula (V) can be added to the suspension. An acid can then be added to the suspension. Formula (Ib) can then optionally be recovered using any suitable method.

In some embodiments, Formula (IV) (e.g., 0.0063 mol, 0.011 mol, or 0.0036 mol) can be suspended in a solvent (e.g., 25 mL of ethanol). Formula (V) can then be added to the suspension (e.g., in equimolar amounts as Formula (IV), such as 0.0063 mol, 0.011 mol, or 0.0036 mol). An acid (e.g., concentrated sulfuric acid) can then be added (e.g., 6 drops) dropwise to the suspension (e.g., with stirring such as vigorous stirring) to form a precipitate. Formula (Ib) can be recovered (e.g., by filtration) which can optionally include washing the precipitate (e.g., with one or more washes of water, ethanol, or a water/ethanol mixture).

Formula (Ib) can be optionally or further recovered. Recovery can occur using any suitable method including but not limited to HPLC (e.g., reverse phase), LC, filtration, precipitation, centrifugation, column chromatography (e.g., size exclusion chromatography or ion exchange chromatography), use of silica gel, washings (e.g., one or more time with one or more solvents or solvent mixtures), or combinations thereof.

In some embodiments, Formula (Ib) can be reacted with Formula (VI) to provide Formula (Ia).

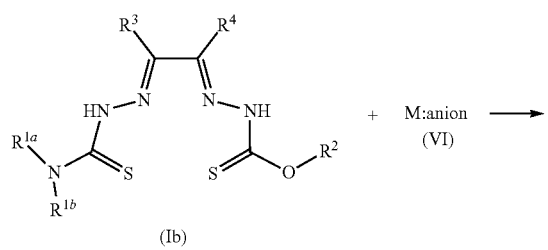 + M:anion (VI) →

(Ib)

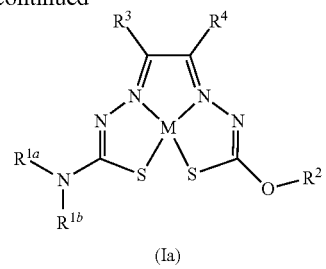

(Ia)

M of Formula (VI) is the same as that defined in Formula (I). The M:anion of Formula (VI) can be prepared using any suitable method or can be purchased if available. The term "anion" (i.e., from M:anion) can be any suitable anion including but not limited to any a non-basic anion (e.g., in the presence of a suitable base) or a suitable weak base (e.g., a weak base without any added water or a weak base with added water such as monohydrate, dihydrate, trihydrate, or tetrahydrate), acetate, acetate monohydrate, acetate dihydrate, or acetate tetrahydrate.

In some embodiments, Formula (Ib) can be reacted with Formula (VI) to provide Formula (Ia) under the following conditions: Formula (Ib) can be suspended in a solvent (e.g., methanol). Formula (VI) can be added. The mixture can be heated. Formula (Ia) can then optionally be recovered using any suitable method.

In some embodiments, Formula (Ib) (e.g., 0.00129 mol) can be suspended in about methanol. Formula (VI) (e.g., in a molar excess of Formula (Ib), such as 0.00149 mol) can be added to the suspension. The suspension can be heated (e.g., refluxed for four hours) and then cooled (e.g., to room temperature) to produce a precipitate. Formula (Ia) can be optionally recovered (e.g., by filtration) which can optionally include washing the precipitate (e.g., with one or more washes of water, ethanol, or a water/ethanol mixture).

Formula (Ia) can be optionally or further recovered. Recovery can occur using any suitable method including but not limited to HPLC (e.g., reverse phase), LC, filtration, precipitation, centrifugation, column chromatography (e.g., size exclusion chromatography or ion exchange chromatography), use of silica gel, washings (e.g., one or more time with one or more solvents or solvent mixtures), or combinations thereof.

In some embodiments, a method for the preparation of a compound of Formula (I) can comprise one or more of the above-mentioned steps. In certain embodiments, a method for preparing a compound of Formula (I) comprises (a) reacting a compound of Formula (II) with a compound of Formula (III) to result in a mixture comprising a compound of Formula (IV) and (b) reacting a compound of Formula (IV) with a compound of Formula (V) to result in a mixture comprising a compound of Formula (Ib). In other embodiments, the method further comprises recovering Formula (Ib). In yet other embodiments, the method further comprises (c) reacting a compound of Formula (Ib) with a compound of Formula (VI) and (d) recovering Formula (Ia).

The presently-disclosed subject matter is further illustrated by the following specific but non-limiting examples. The following examples may include compilations of data that are representative of data gathered at various times during the course of development and experimentation related to the present invention.

EXAMPLES

Example Set A

Anti-Proliferative Activity of Compounds Using MTT Assay—Methods

Anti-proliferative activity of the indicated compounds was evaluated for A549 (human lung adenocarcinoma) cells and IMR-90 (human non-malignant lung fibroblast) cells using a previously published 3-(4,5-dimethylthiazol-2-yl)-2,5-diphenyltetrazolium bromide (MTT) assay protocol (MORGAN, "Tetrazolium (MTT) Assay For Cellular Viability And Activity" Methods Mol. Biol. (1998) Vol. 79, pp. 179-183; BATES et al., "Antiproliferative Activity of G-rich Oligonucleotides Correlates with Protein Binding" J. Biol. Chem. (1999) Vol. 274, No. 37, pp. 26369-26377; SALIPUR et al., "A Novel Small Molecule That Induces Oxidative Stress And Selectively Kills Malignant Cells" Free Radical Biology and Medicine (2014) Vol. 68, pp. 110-121. Cells were seeded in quadruplicate wells in 96-well plates and allowed to adhere overnight. To account for intrinsic differences in growth rates, cells were plated at the following densities to achieve comparable MTT absorbance values ($OD_{570}$ between 0.5 and 1) for untreated cells: A549, 1000 cells/well; IMR-90, 5000 cells/well. After 72 hrs of treatment with test compounds, MTT (Sigma, St. Louis, Mo.) was added for 4 hrs prior to cell lysis. Each assay was performed in at least triplicate.

Anti-Proliferative Activity of Compounds Using MTT Assay—Results

FIGS. 1-3, 6, 8, 11, 13, and 14 show that some compounds containing Cu appear to have a greater activity in cancer cells (A549) compared to some compounds containing Zn. FIGS. 1-3, 6-8, 11-14, and 17 show that some compounds containing Ni did not appear to reduce cancer cell growth, as much as Cu or Zn containing compounds.

FIGS. 4, 5, 9, 10, 15, 16, and 18 indicate that the ligands themselves appear to reduce cancer cell growth. Without being bound by theory, this could occur by self-assembling with trace metals (e.g., Cu) in the medium.

One Dose Data—Methods

The One-dose method can be found at <<https://dtp.cancer.gov/discovery_development/nci-60/methodology.htm>> which is herein incorporated by reference in its entirety. In general, compounds submitted to the NCI-60 human cancer cell line screen were tested initially at a single high dose (10 µM) for a fixed period of time in the panel's 60 cell lines. The list of cell lines can be found at <<https://dtp.cancer.gov/discovery_development/nci-60/cell_list.htm>> which is herein incorporated by reference in its entirety and some characteristics of these cell lines can be found at <<https://www.nature.com/articles/sdata2017157/tables/1>> which is herein incorporated by reference in its entirety. The list of cell lines is also provided in Table 2, which are listed in the same order as that found in FIGS. 19-20.

TABLE 2

| Cell Line | Related Cancer |
|---|---|
| CCRF-CEM | Leukemia |
| HL-60(TB) | Leukemia |
| K-562 | Leukemia |
| MOLT-4 | Leukemia |
| RPMI-8226 | Leukemia |
| SR | Leukemia |
| A549/ATCC | Non-Small Cell Lung |
| EKVX | Non-Small Cell Lung |
| HOP-62 | Non-Small Cell Lung |
| HOP-92 | Non-Small Cell Lung |
| NCI-H226 | Non-Small Cell Lung |
| NCI-H23 | Non-Small Cell Lung |
| NCI-H322M | Non-Small Cell Lung |
| NCI-H460 | Non-Small Cell Lung |
| NCI-H522 | Non-Small Cell Lung |
| COLO 205 | Colon |
| HCC-2998 | Colon |
| HCT-116 | Colon |
| HCT-15 | Colon |
| HT29 | Colon |
| KM12 | Colon |
| SW-620 | Colon |
| SF-268 | CNS |
| SF-295 | CNS |
| SF-539 | CNS |
| SNB-19 | CNS |
| SNB-75 | CNS |
| U251 | CNS |
| LOX IMVI | Melanoma |
| MALME-3M | Melanoma |
| M14 | Melanoma |
| MDA-MB-435 | Melanoma |
| SK-MEL-2 | Melanoma |
| SK-MEL-28 | Melanoma |
| SK-MEL-5 | Melanoma |
| UACC-257 | Melanoma |
| UACC-62 | Melanoma |
| IGR-OV1 | Ovarian |
| OVCAR-3 | Ovarian |
| OVCAR-4 | Ovarian |
| OVCAR-5 | Ovarian |
| OVCAR-8 | Ovarian |
| NCI/ADR-RES | Ovarian |
| SK-OV-3 | Ovarian |
| 786-0 | Renal |
| A498 | Renal |
| ACHN | Renal |
| CAKI-1 | Renal |
| RXF 393 | Renal |
| SN12C | Renal |
| TK-10 | Renal |
| UO-31 | Renal |
| PC-3 | Prostate |
| DU-145 | Prostate |
| MCF7 | Breast |
| MDA-MB-231/ATCC | Breast |
| HS 578T | Breast |
| BT-549 | Breast |
| T-47D | Breast |
| MDA-MB-468 | Breast |

The One-dose data is reported as a mean graph of the percent growth of treated cells. The number reported for the One-dose assay is growth relative to the no-drug control, and relative to the time zero number of cells. This allows detection of both growth inhibition (values between 0 and 100) and lethality (values less than 0). For example, a value of 100 means no growth inhibition. A value of 40 would mean 60% growth inhibition. A value of 0 means no net growth over the course of the experiment. A value of −40 would mean 40% lethality. A value of −100 means all cells are dead.

One Dose Data—Results

Figure 19:
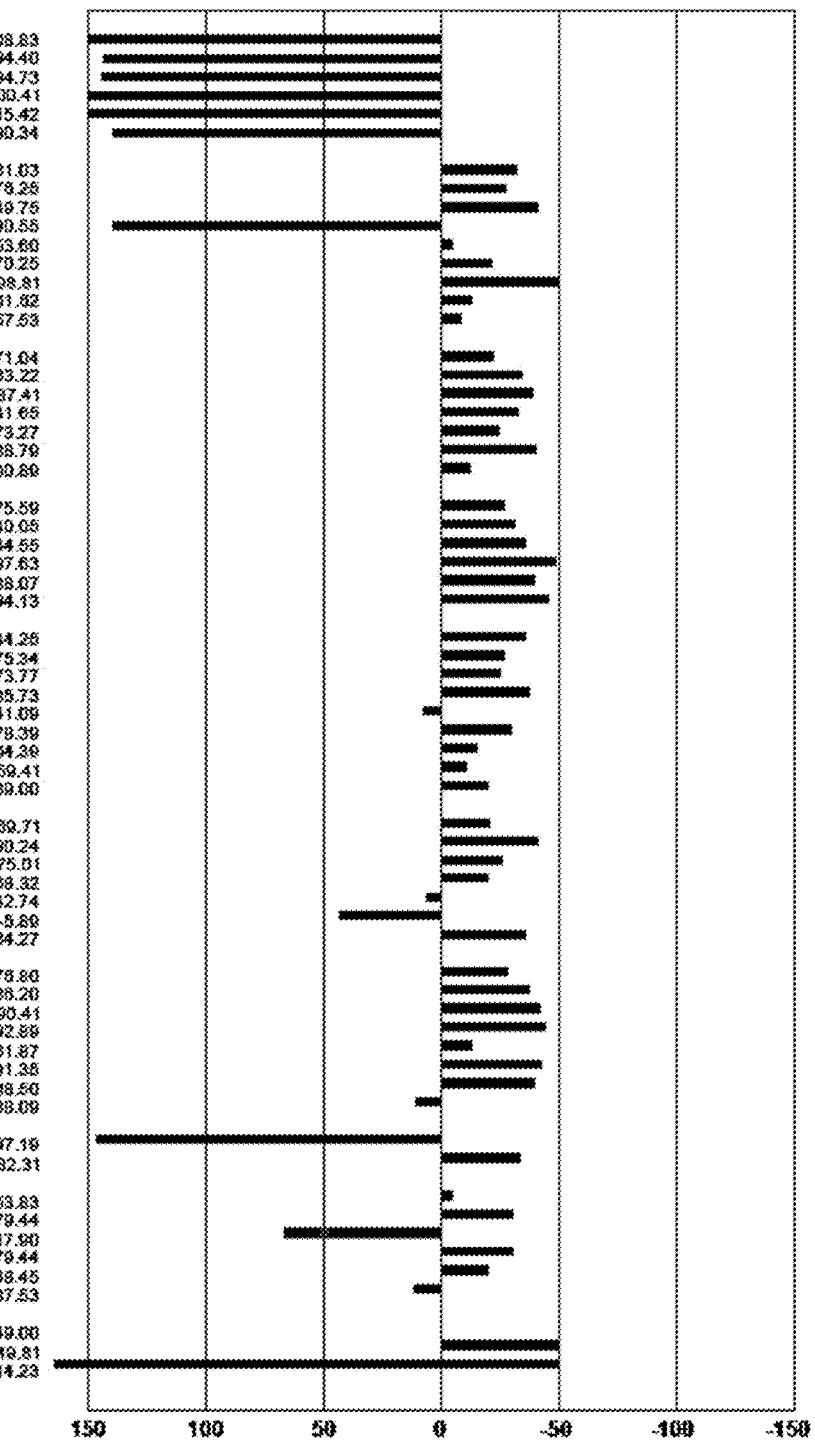
FIG. 19: One-dose data for compound I-1 (NV3104). The compound is tested at a single high dose (10 μM) in the panel's 60 cell lines.
Figure 20:
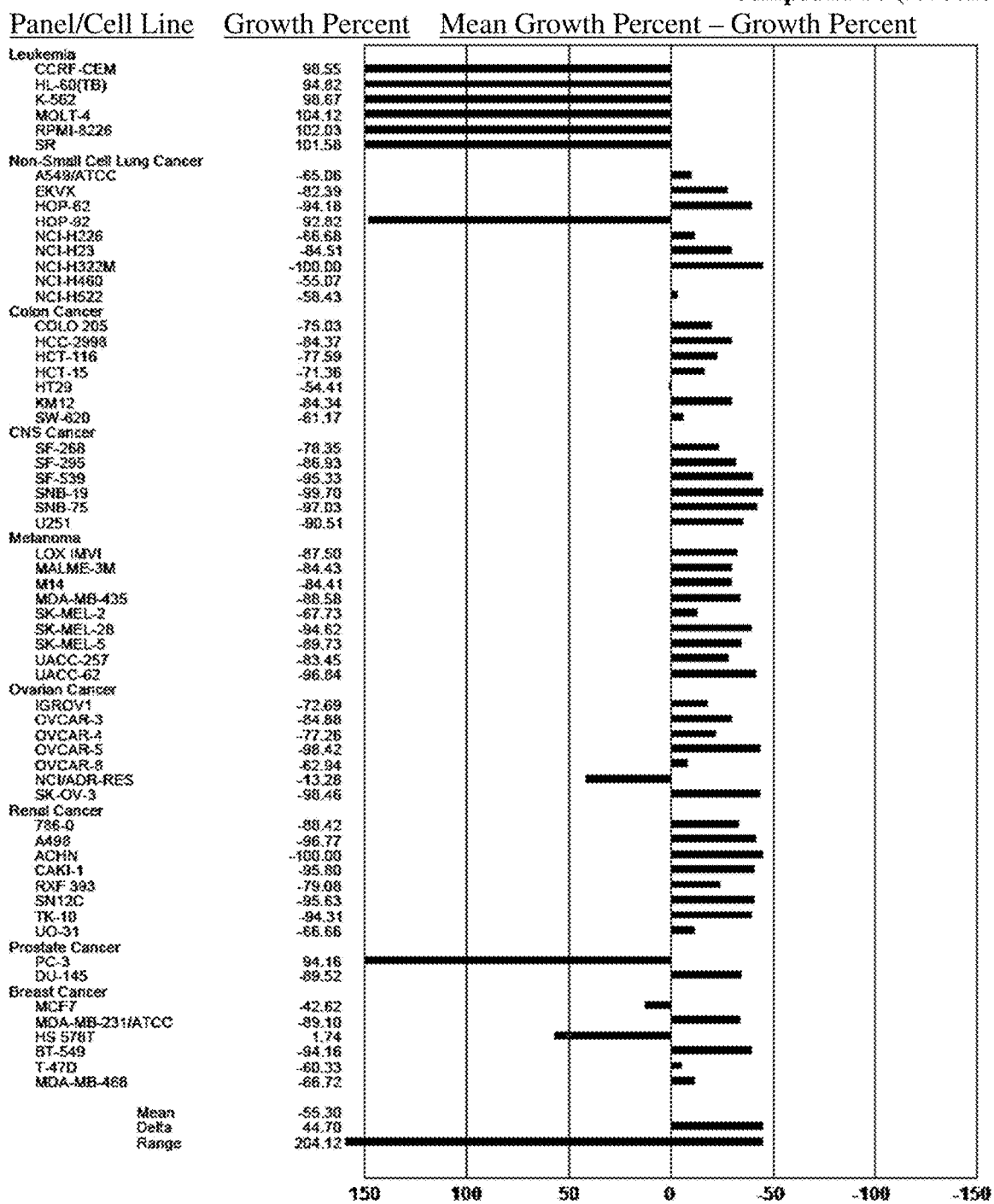
FIG. 20: One-dose data for compound I-5 (NV30189). The compound is tested at a single high dose (10 μM) in the panel's 60 cell lines.

FIGS. 19-20 indicate that the two compounds (I-1 and I-5) appear to have similar profiles; this could suggest they have the same mechanism of action. FIGS. 19-20 indicate that the two compounds provide 100% growth inhibition or better at 10 µM in most cell lines, and close to 100% cytotoxicity (all cells dead) in some cell lines. FIGS. 19-20 also appear to indicate that the growth of leukemia cells is not as inhibited as other cell types.

Cell Proliferation and Reactive Oxygen Species (ROS) Production—Methods

A549 (human lung adenocarcinoma) cells and MDA-MB-231 (human breast adenocarcinoma) cells were cultured in DMEM medium containing 10% FBS and 1% Penicillin/Streptomycin. IMR-90 (human non-malignant lung fibroblast) cells were cultured in EMEM medium containing 10% FBS and 1% Penicillin/Streptomycin. MCF10A (human non-malignant breast epithelial) cells in MEBM containing 10% FBS. Cell viability after treatment was determined using 3-(4,5-dimethylthiazol-2-yl)-2,5-diphenyltetrazolium bromide (MTT). After 72 h treatment with compound, a 5 mg/ml solution MTT of (Sigma, St. Louis, Mo.) was added in at 1/10 total sample volume. Cells were then incubated for 4 h. Lysis buffer (10% SDS in 0.01 N HCl) was added at half of the original sample volume and incubated overnight. Plates were read at 570 nm. Graphs indicate average of one or two experiments (performed in quadruplet wells)±SEM. Cell death in A549 cells was assessed by trypan blue exclusion. Average of one or two experiments (each performed in triplicate)±SEM displayed on graphs. ROS production in A549 lung cancer cells after 48 h treatment with the compounds was assayed using ROS-Glo™ $H_2O_2$ Assay Kit (Promega). Graph displays mean of three experiments performed ±SEM as percent of vehicle.

Cell Proliferation and Reactive Oxygen Species (ROS) Production—Results

Figure 21:
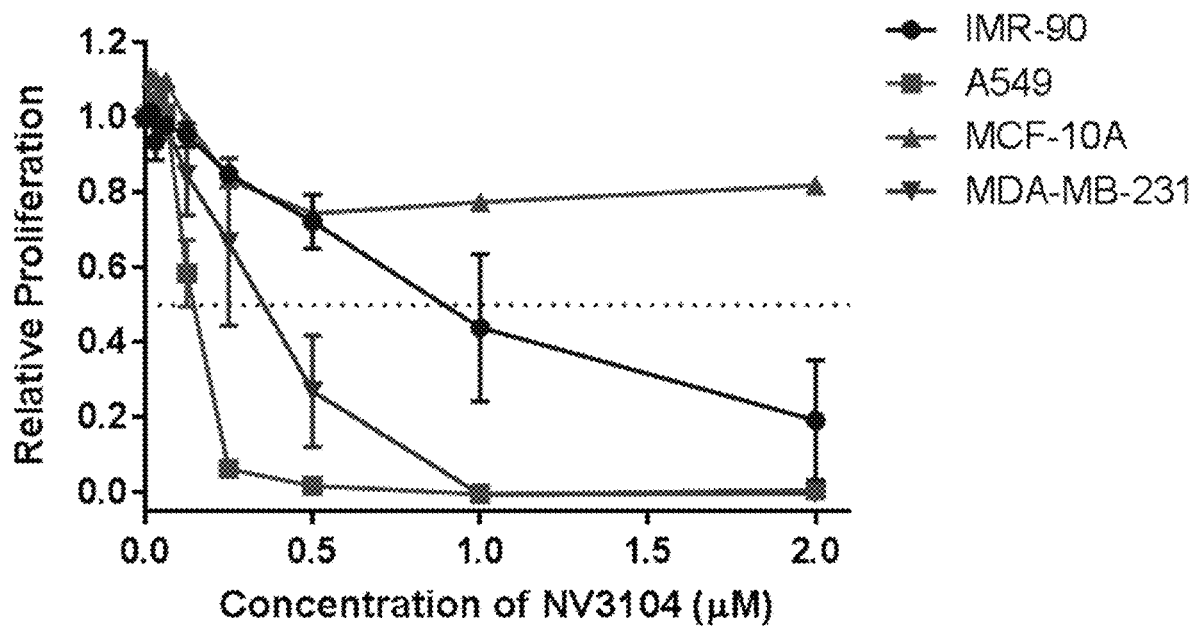
FIG. 21: Cell proliferation for several cell lines using MTT assays for compound I-1 (NV3104).
Figure 22:
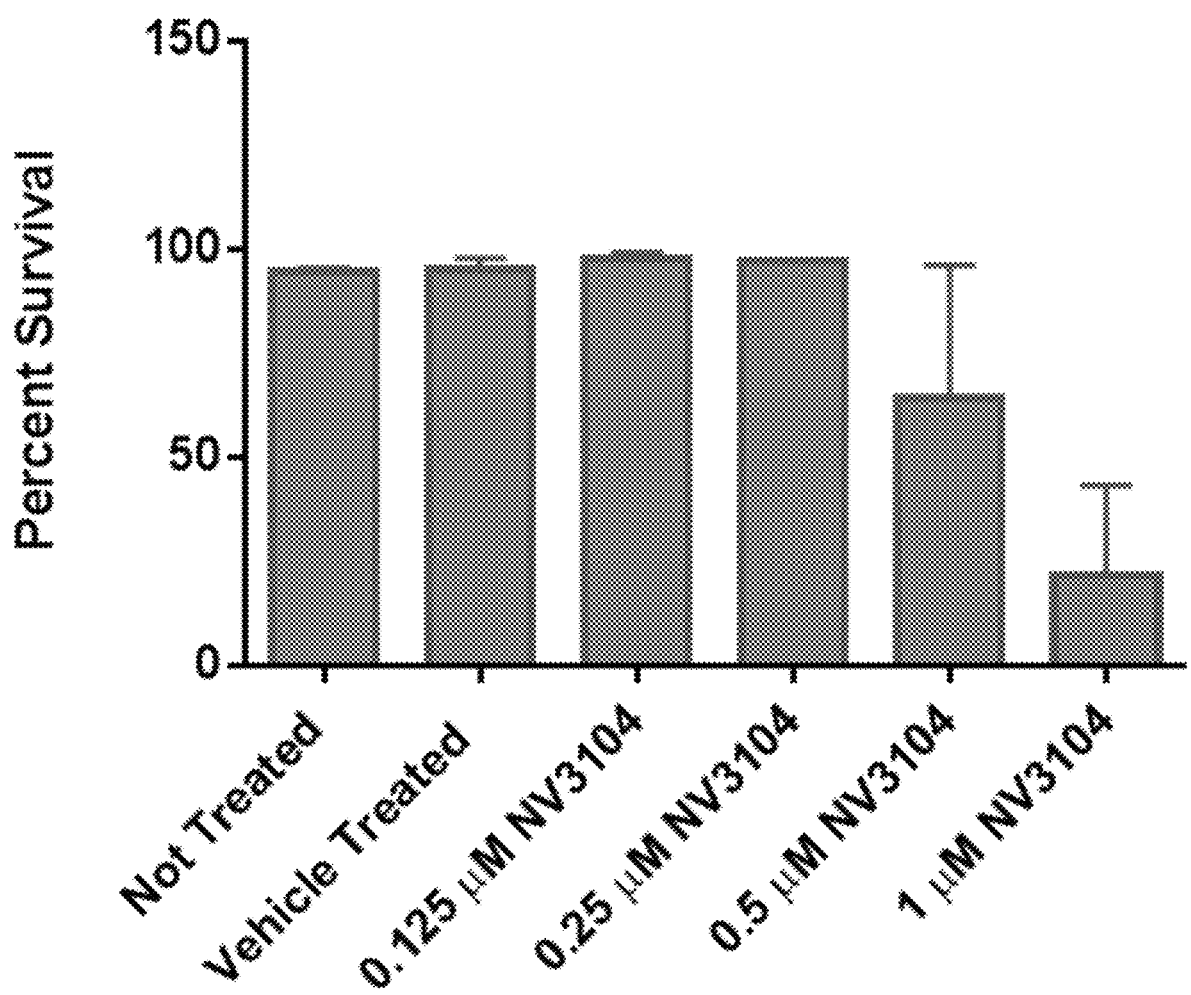
FIG. 22: Cell survival assays of A549 lung cancer cells for compound I-1 (NV3104) at several concentrations.

FIGS. 21-22 indicate that compound I-1 was able to inhibit proliferation of cancer cells at lower concentrations than in non-malignant cells. The $GI_{50}$ values (concentration needed to inhibit cell proliferation by 50%) for compound I-1 for each cell line are: A549 (0.13 µM); MDA-MB-231 (0.34 µM); IMR-90 (0.98 µM); MCF 10A (>2 µM). These results suggest that compound I-1 is selectively toxic to cancer cells.

Figure 23:
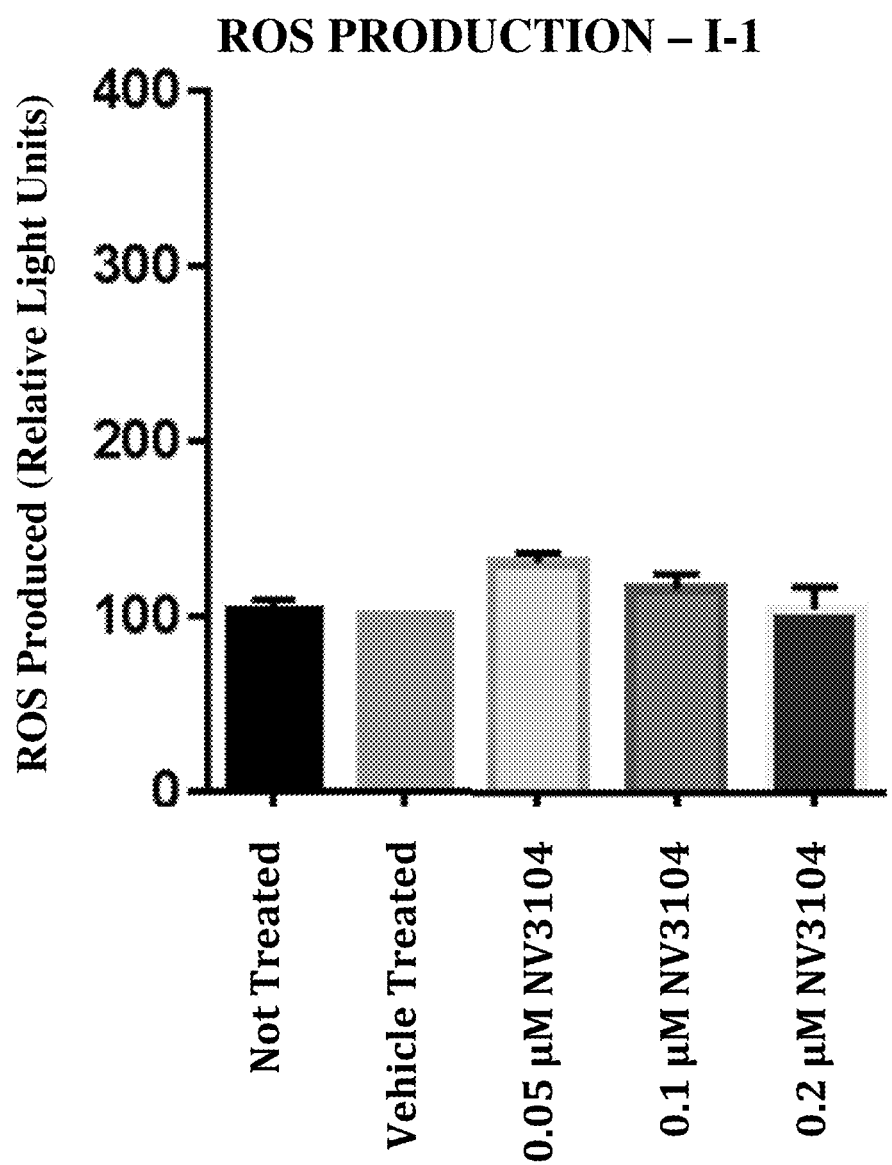
FIG. 23: Reactive Oxygen Species (ROS) production of A549 lung cancer cells for several concentrations of compound I-1 (NV3104).

FIG. 23 shows that compound I-1 does not produce a significant increase in ROS. This suggests that the mechanism for the toxicity of compound I-1 does not involve increasing ROS within cancer cells; a different mechanism could be implicated.

Example Set B—Synthetic Methods and Compound Characterization

The following reactions (A-F) are referenced in Example Set B.

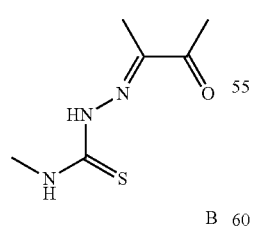

A

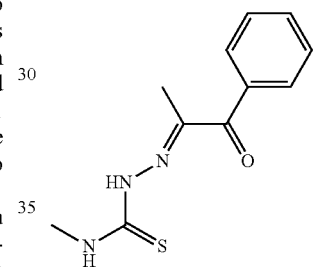

B

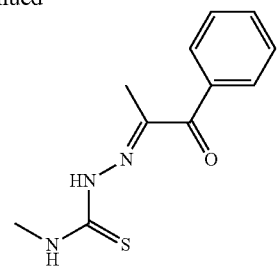

C

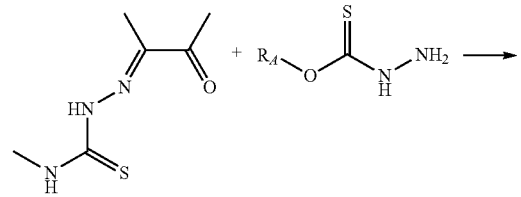

D

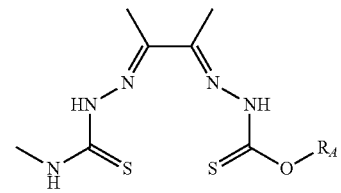

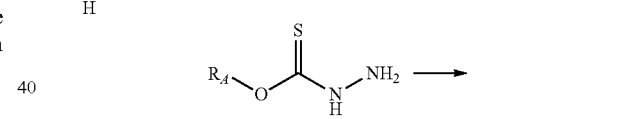

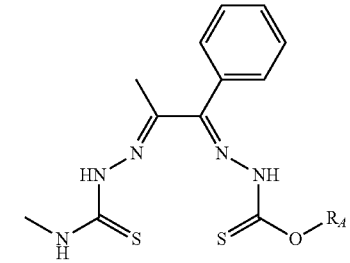

E

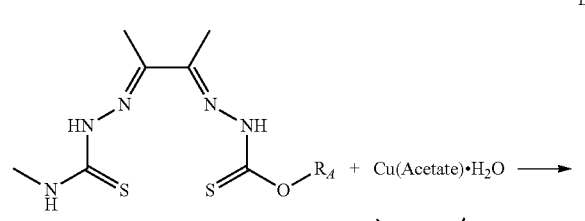

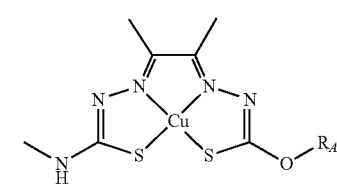

-continued

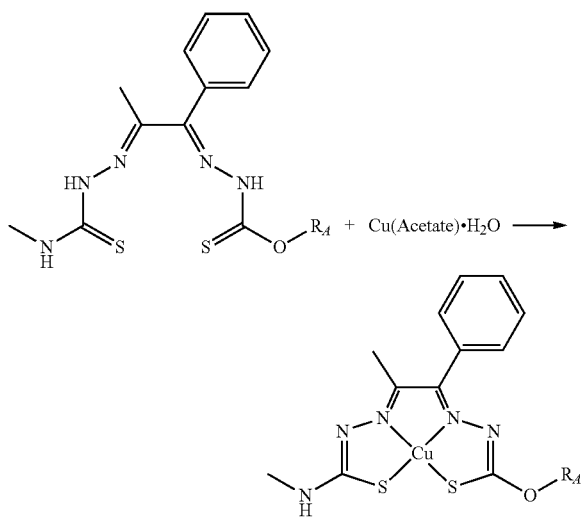

All starting materials were purchased from a commercial vendor, synthesized according to literature procedures, or otherwise described herein. The hydrazinecarbothioc acid O-alkyl esters were synthesized according to Reuifenacht 1972 (REUFENACHT, "Arbetien iber Phosphosäure-und Thiosphosphorsaiureester mit einem Heterocyclischen Substituenten Thiadiazol-Ringschluss und eine Dabei Auftretende Methyluibertragung" Helv. Chim. Acta (1972) Vol. 55, Issue 4, pp. 1178-1187). The reactions A and B are modified from Bocokic et al. 2012 (BOCOKIC et al., "Bis-(thiosemicarbazonato) Zn(ii) complexes as building blocks for construction of supramolecular catalysts" Dalton Trans. (2012) Vol. 41, Issue 13, pp. 3740-3750). The 4-methyl-3-thiosemicarbazide was purchased from Alfa Aesar, the 2,3-butane dione and 1-phenyl-1,2-propane dione were purchased from Sigma Aldrich, and the copper acetate was purchased from Lancaster.

Reaction A

Figure 24:
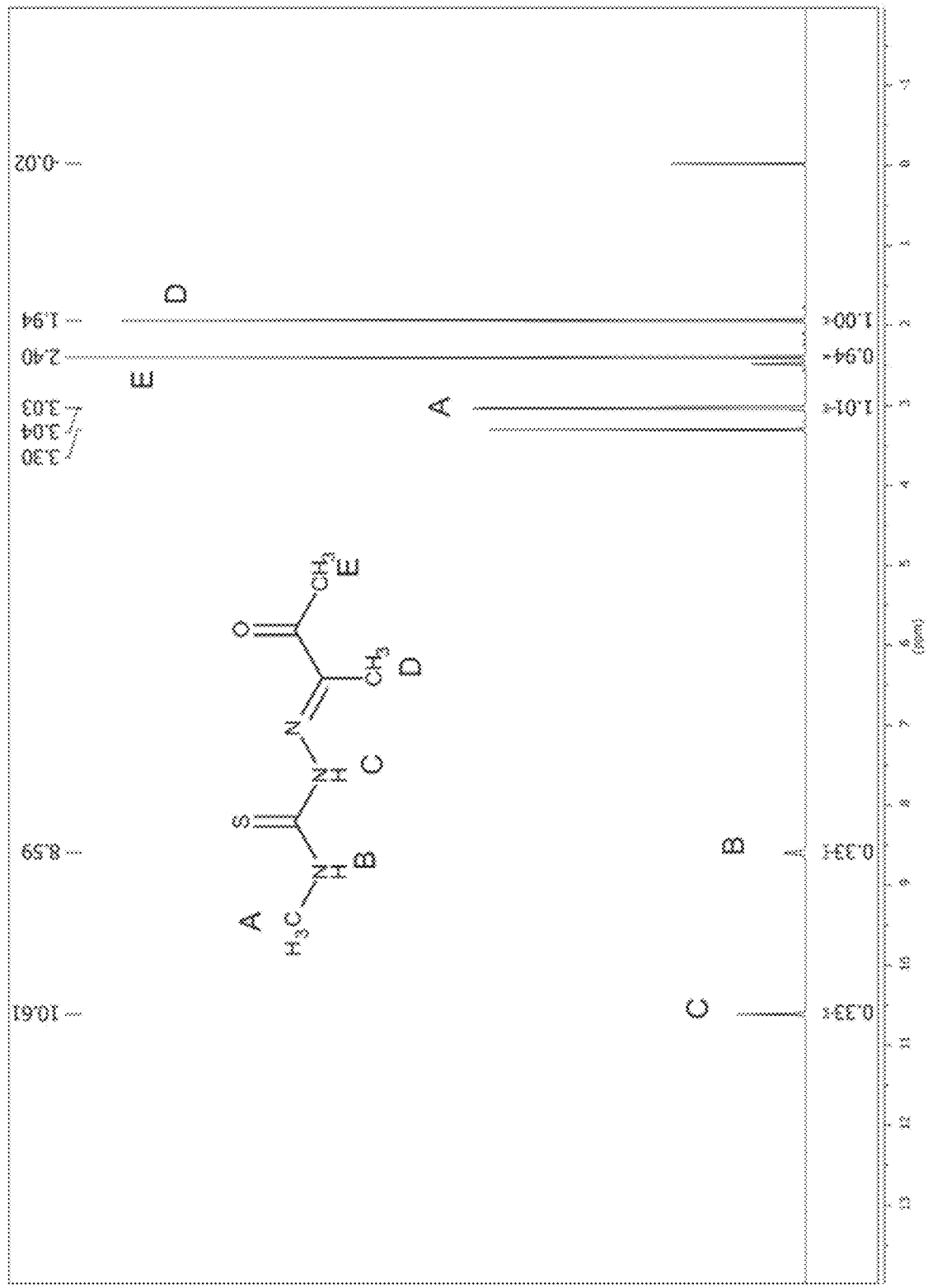
FIG. 24: The $^1$H NMR spectrum of the product of reaction A.
Figure 25:
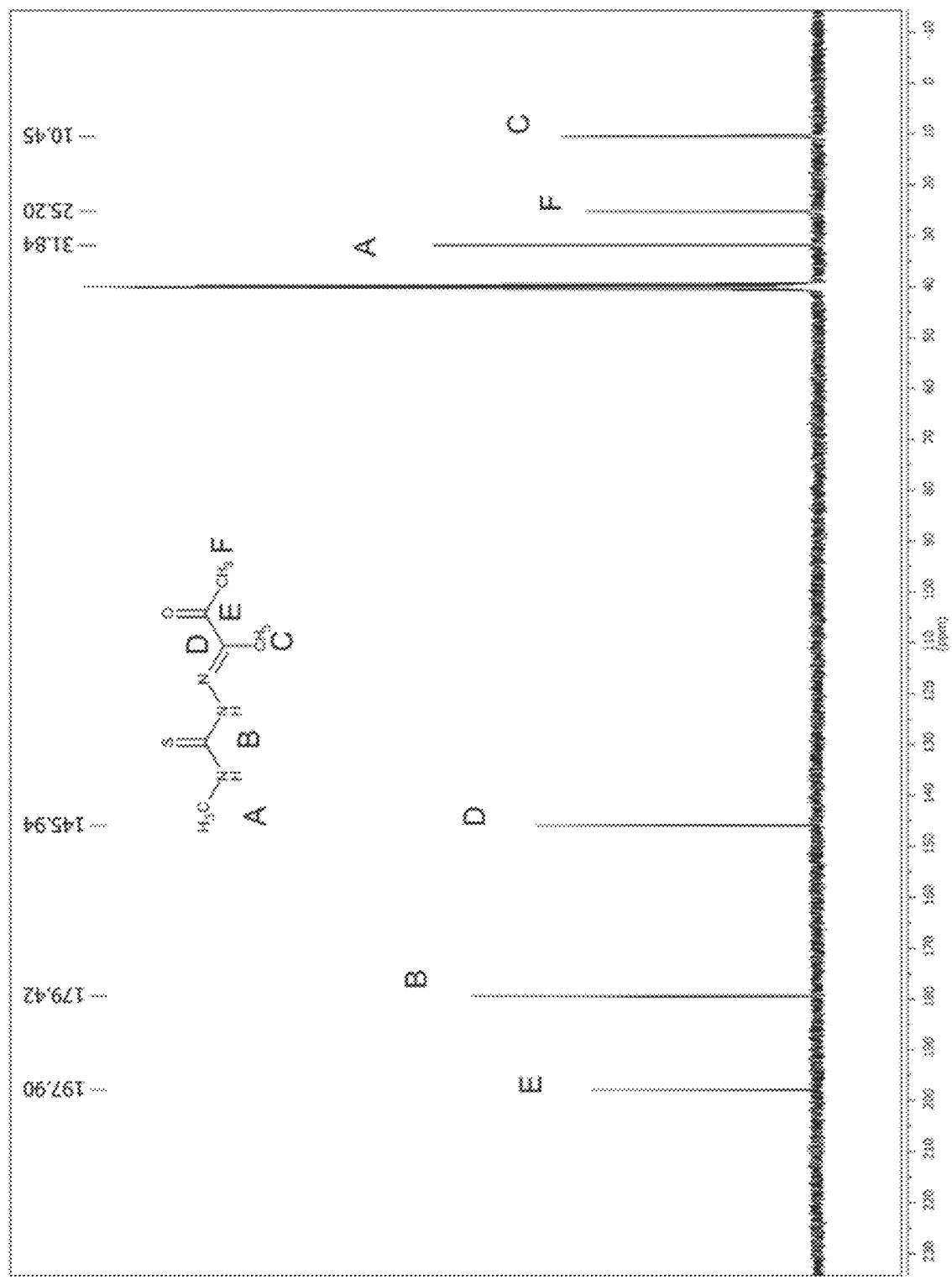
FIG. 25: The $^{13}$C NMR spectrum of the product of reaction A.

In 25 mL of water 2,3-butane dione (2.5 mL, 0.0285 mol) was mixed with 6 drops of concentrated sulfuric acid. In 100 mL of water the 4-methyl-3-thiosemicarbazide (1.0 g, 0.0095 mol) was dissolved. The solution of the 4-methyl-3-thiosemicarbazide was added to the dione solution at a drop rate of 1 drop per 3 seconds with vigorous stirring. A white precipitate formed and was isolated via filtration with a water wash. 1.55 g (95%) yield. The $^1$H NMR spectrum of the product of reaction A is shown in FIG. 24 and the $^{13}$C NMR spectrum of the product is shown in FIG. 25.

Reaction B

Figure 26:
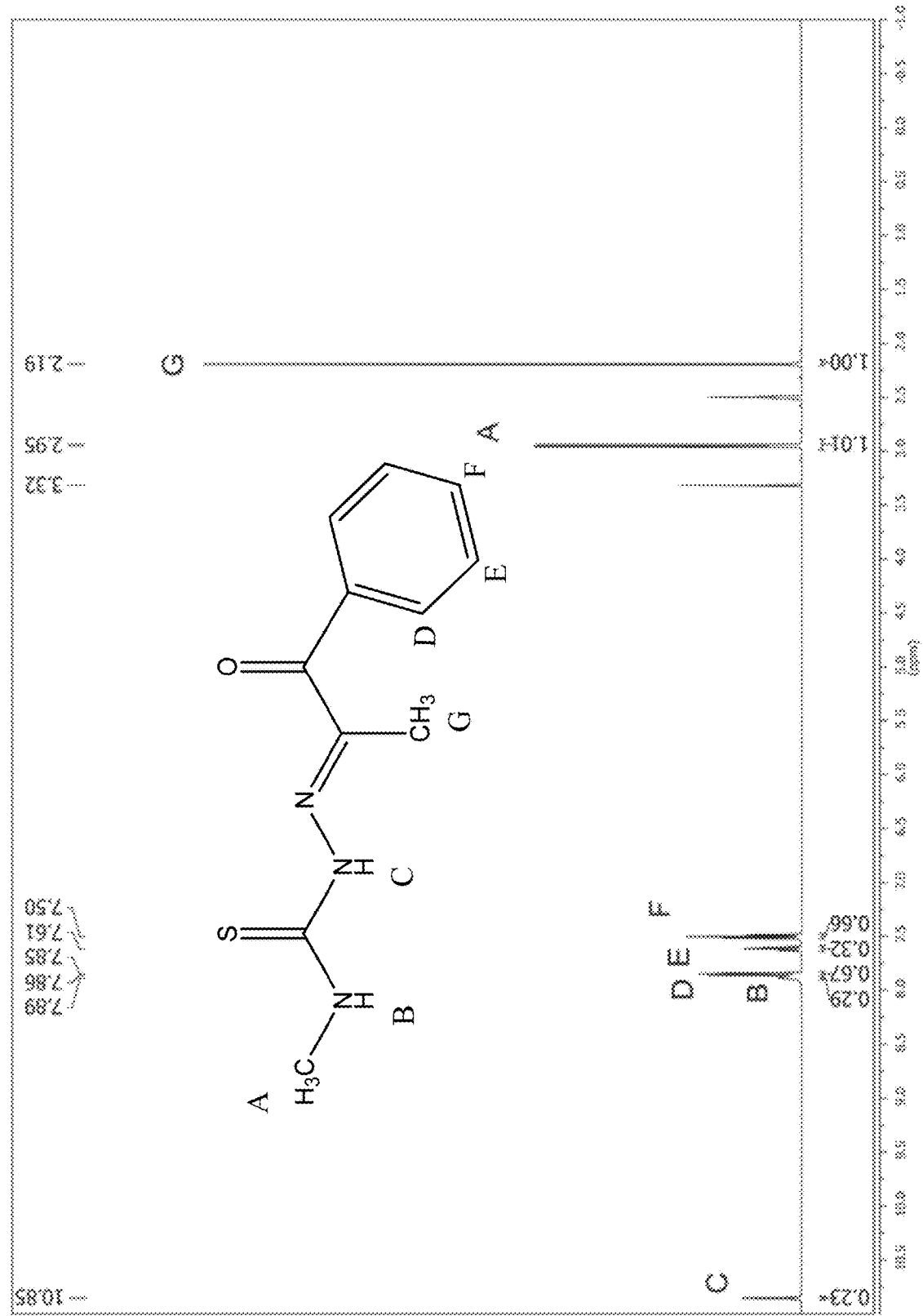
FIG. 26: The $^1$H NMR spectrum of the product of reaction B.
Figure 27:
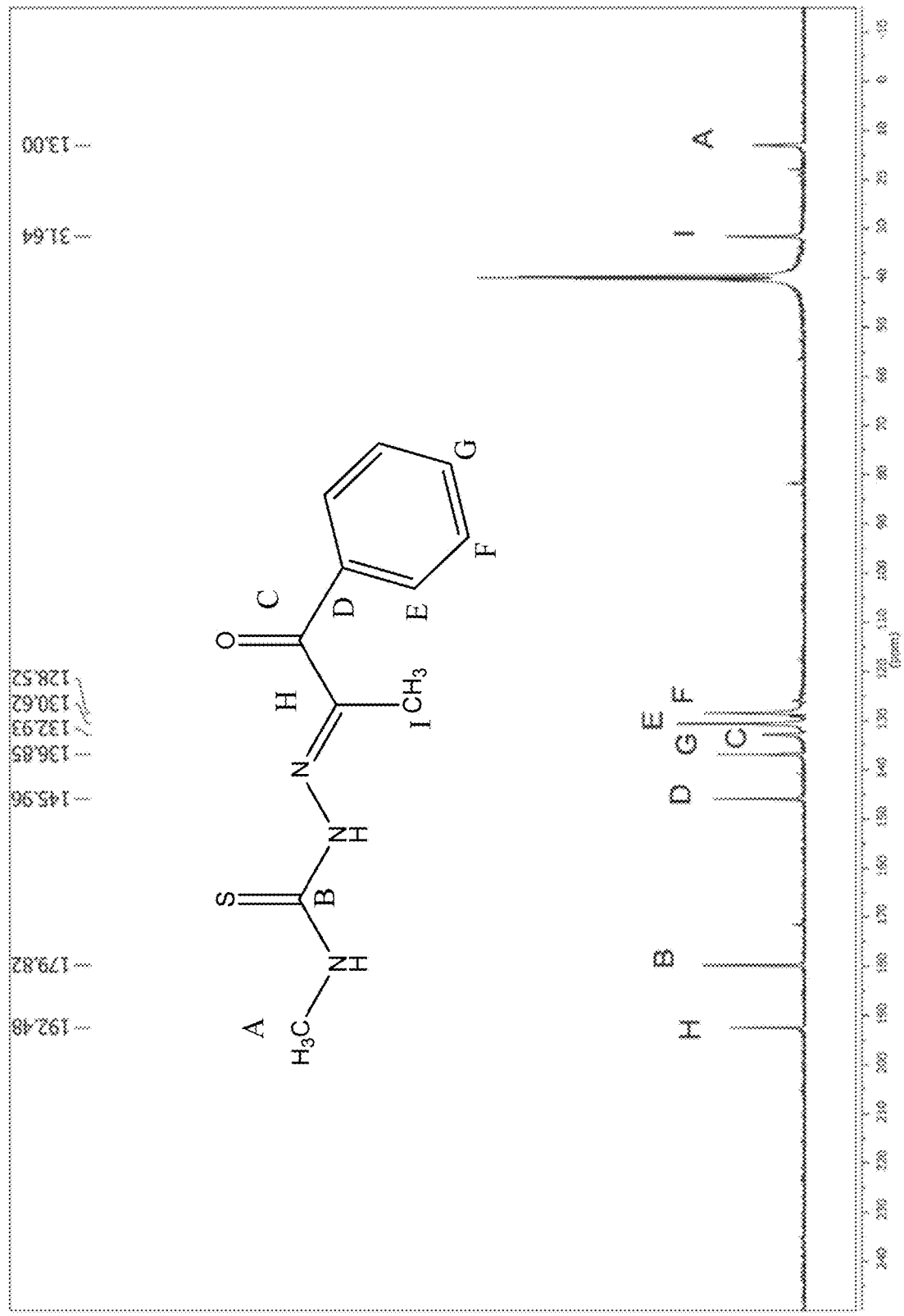
FIG. 27: The $^{13}$C NMR spectrum of the product of reaction B.

In 25 mL of ethanol 1-phenyl-2,3-propane dione (3.8 mL, 0.0285 mol) was mixed with 6 drops of concentrated sulfuric acid. In 100 mL of ethanol (1.0 g 0.0095 mol) the 4-methyl-3-thiosemicarbazide was dissolved. The solution of the 4-methyl-3-thiosemicarbazide was added to the dione solution at a drop rate of 1 drop per 3 seconds with vigorous stirring. The solution was then concentrated under vacuum and then stored in a freezer overnight. A yellow solid formed after being placed in the freezer. This yellow solid was then filtered and washed with ethanol. 1.55 g (70%) yield. The $^1$H NMR spectrum of the product of reaction B is shown in FIG. 26 and the $^{13}$C NMR spectrum of the product of reaction B is shown in FIG. 27.

Reaction C—Generic Procedure

In 25 mL of ethanol, the compound isolated from reaction A was suspended. The appropriate hydrazinecarbothioc acid O-alkyl esters ($R_A$=ethyl or propyl) was added to this suspension, followed by 6 drops of concentrated sulfuric acid. A white/creme precipitate formed and was isolated via filtration with an ethanol and water wash.

Reaction C—$R_A$=Ethyl

Figure 28:
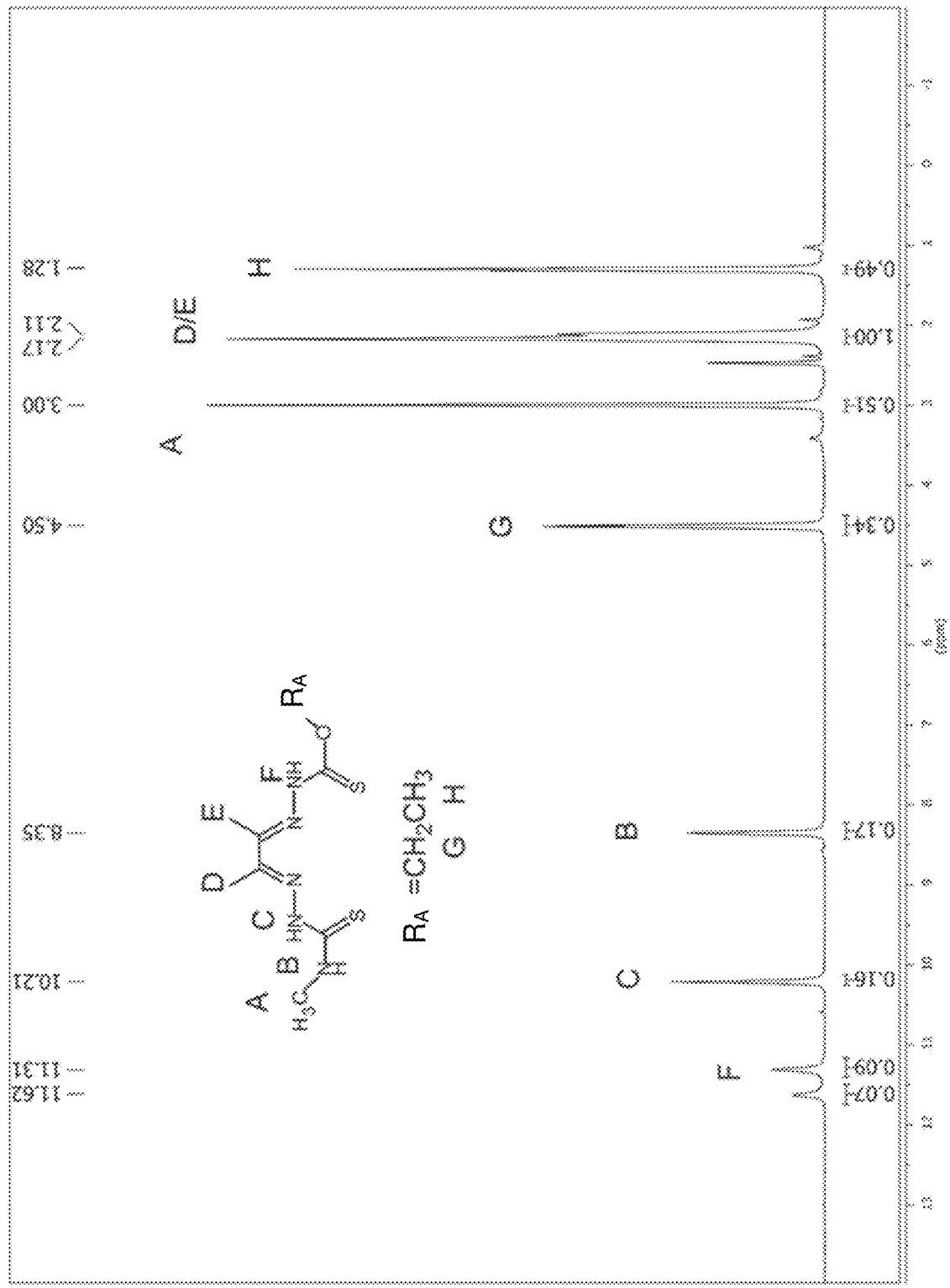
FIG. 28: The $^1$H NMR spectrum of the product of reaction C (ethyl) which is compound I-4.
Figure 29:
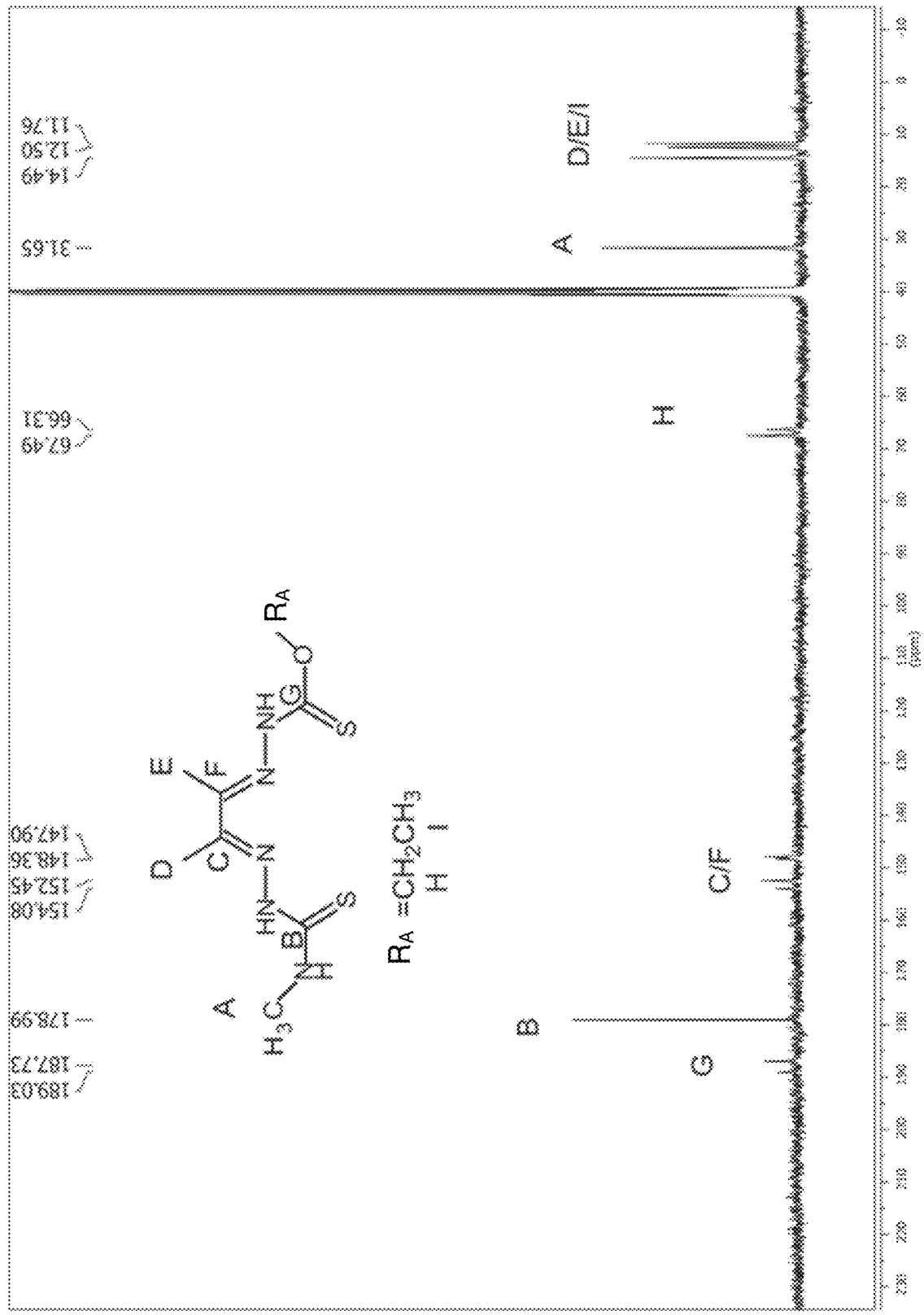
FIG. 29: The $^{13}$C NMR spectrum of the product of reaction C (ethyl) which is compound I-4.

In 25 mL of ethanol, the compound isolated from reaction A was suspended (0.894 g, 0.0063 mol). The hydrazinecarbothioc acid O-ethyl ester (0.760 g, 0.0063 mol) was added to this suspension, followed by 6 drops of concentrated sulfuric acid. A white/creme precipitate formed and was isolated via filtration with an ethanol and water wash. 1.32 g (76%) yield. Elemental analysis calculated: C: 39.25 H: 6.22 N: 25.43. Found: C: 39.12 H: 6.16 N: 25.54. The $^1$H NMR spectrum of the product of reaction C (ethyl) (compound I-4) is shown in FIG. 28 and the $^{13}$C NMR spectrum of the product of reaction C (ethyl) (compound I-4) is shown in FIG. 29.

Reaction C—$R_A$=Propyl

Figure 30:
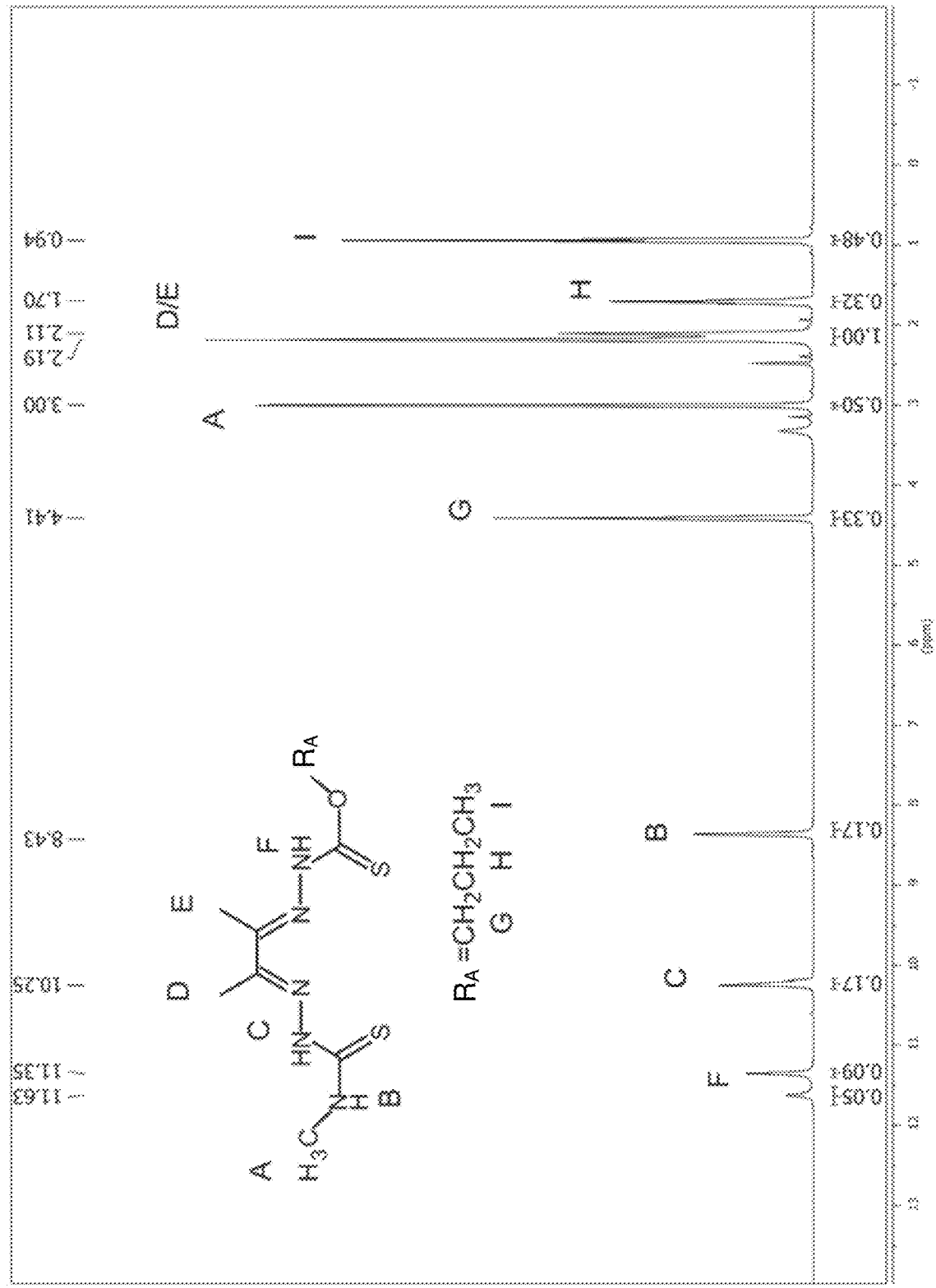
FIG. 30: The $^1$H NMR spectrum of the product of reaction C (propyl) which is compound I-12.
Figure 31:
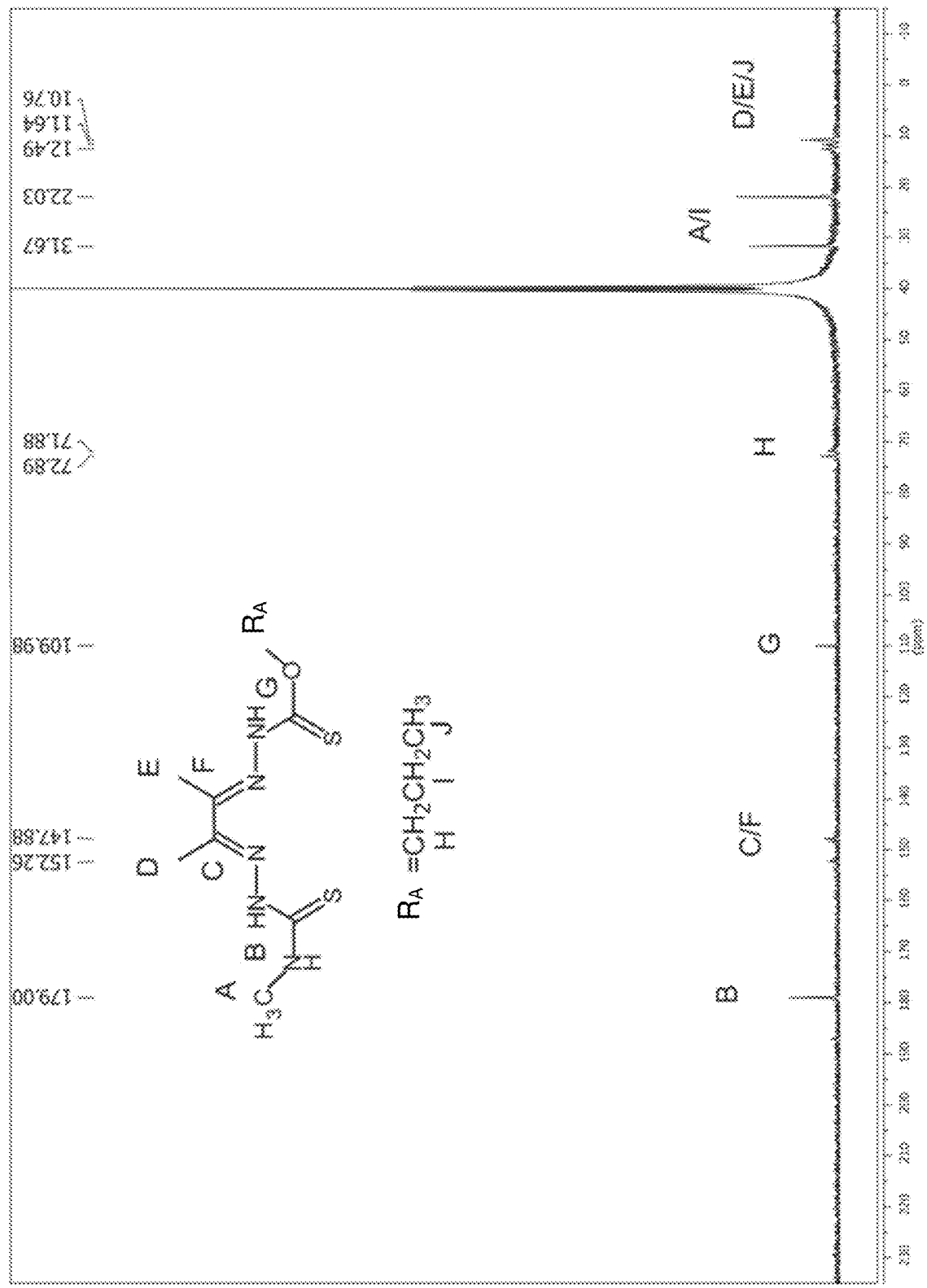
FIG. 31: The $^{13}$C NMR spectrum of the product of reaction C (propyl) which is compound I-12.

In 25 mL of ethanol, the compound isolated from reaction A was suspended (1.58 g, 0.011 mol). The hydrazinecarbothioc acid O-propyl ester (0.1.45 g, 0.011 mol) was added to this suspension, followed by 6 drops of concentrated sulfuric acid. A white/creme precipitate formed and was isolated via filtration with an ethanol and water wash. 1.32 g (75%) yield. Elemental analysis calculated: C: 41.50 H: 6.62 N: 24.20. Found: C: 41.31 H: 6.46 N: 24.02. The $^1$H NMR spectrum of the product of reaction C (propyl) (compound I-12) is shown in FIG. 30 and the $^{13}$C NMR spectrum of the product of reaction C (propyl) (compound I-12) is shown in FIG. 31.

Reaction D

Figure 32:
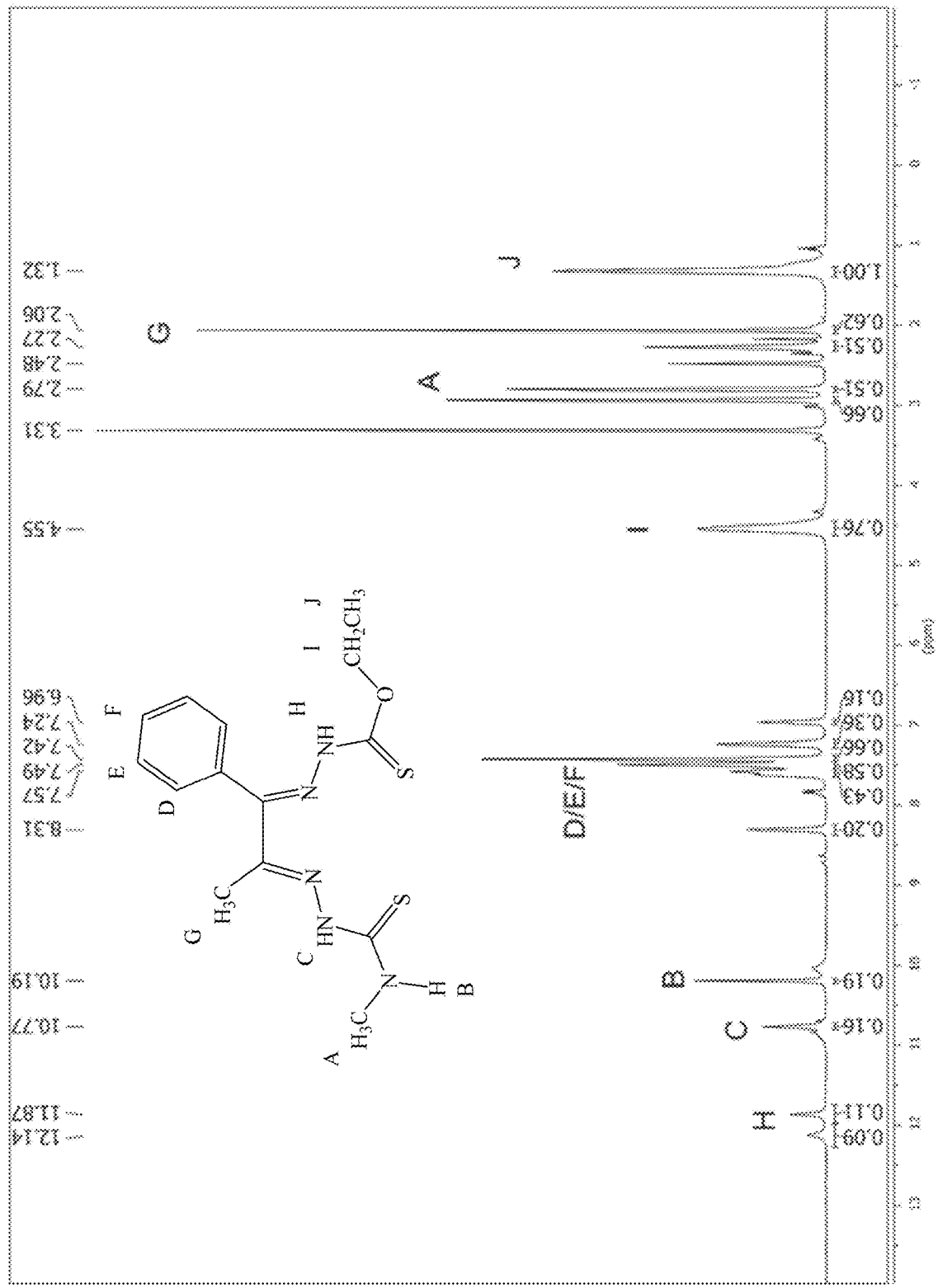
FIG. 32: The $^1$H NMR spectrum of the product of reaction D which is compound I-8.
Figure 33:
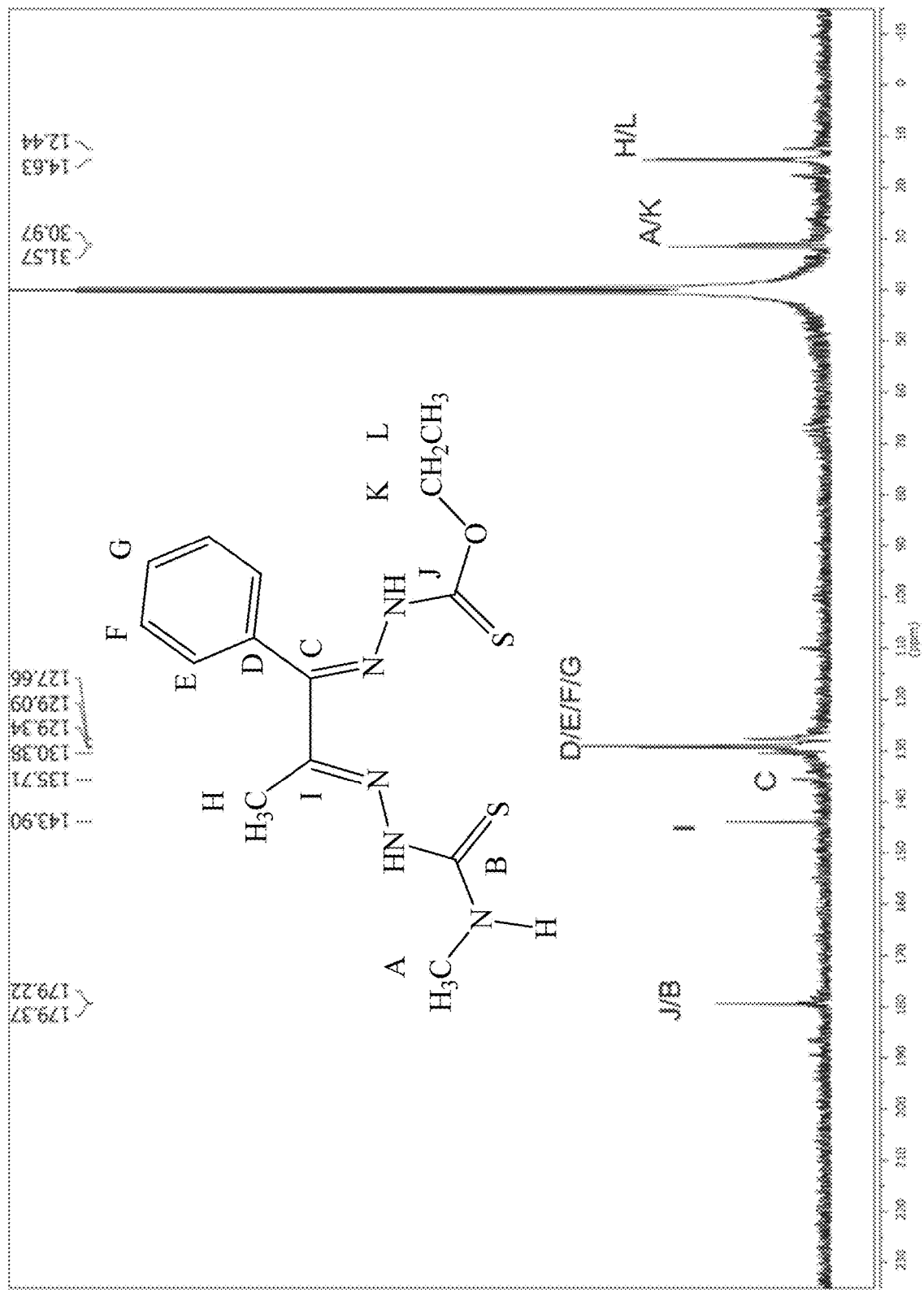
FIG. 33: The $^{13}$C NMR spectrum of the product of reaction D which is compound I-8.

In 25 mL of ethanol, the compound isolated from reaction B (0.840 g, 0.0036 mol) was suspended. The hydrazinecarbothioc acid O-ethyl ester (0.43 g, 0.0036 mol) was added to this suspension, followed by 6 drops of concentrated sulfuric acid. A white/creme precipitate formed and was isolated via filtration with an ethanol and water wash. 0.871 g (72%) yield. Elemental analysis calculated: C: 49.83 H: 5.67 N 20.75. Found: C: 49.14 H: 5.60 N: 20.18. The $^1$H NMR spectrum of the product of reaction D is shown in FIG. 32 and the $^{13}$C NMR spectrum of the product of reaction D (compound I-8) is shown in FIG. 33.

Reaction E—Generic Procedure

The ligand was suspended in methanol (0.00129 mol). To this suspension copper (II) acetate monohydrate (0.00149 mol) was added which caused an immediate color change of the suspension to red-brown. The suspension was refluxed for 4 hours then cooled to room temperature then filtered and washed with methanol.

Reaction E—$R_A$=Ethyl

Figure 34:
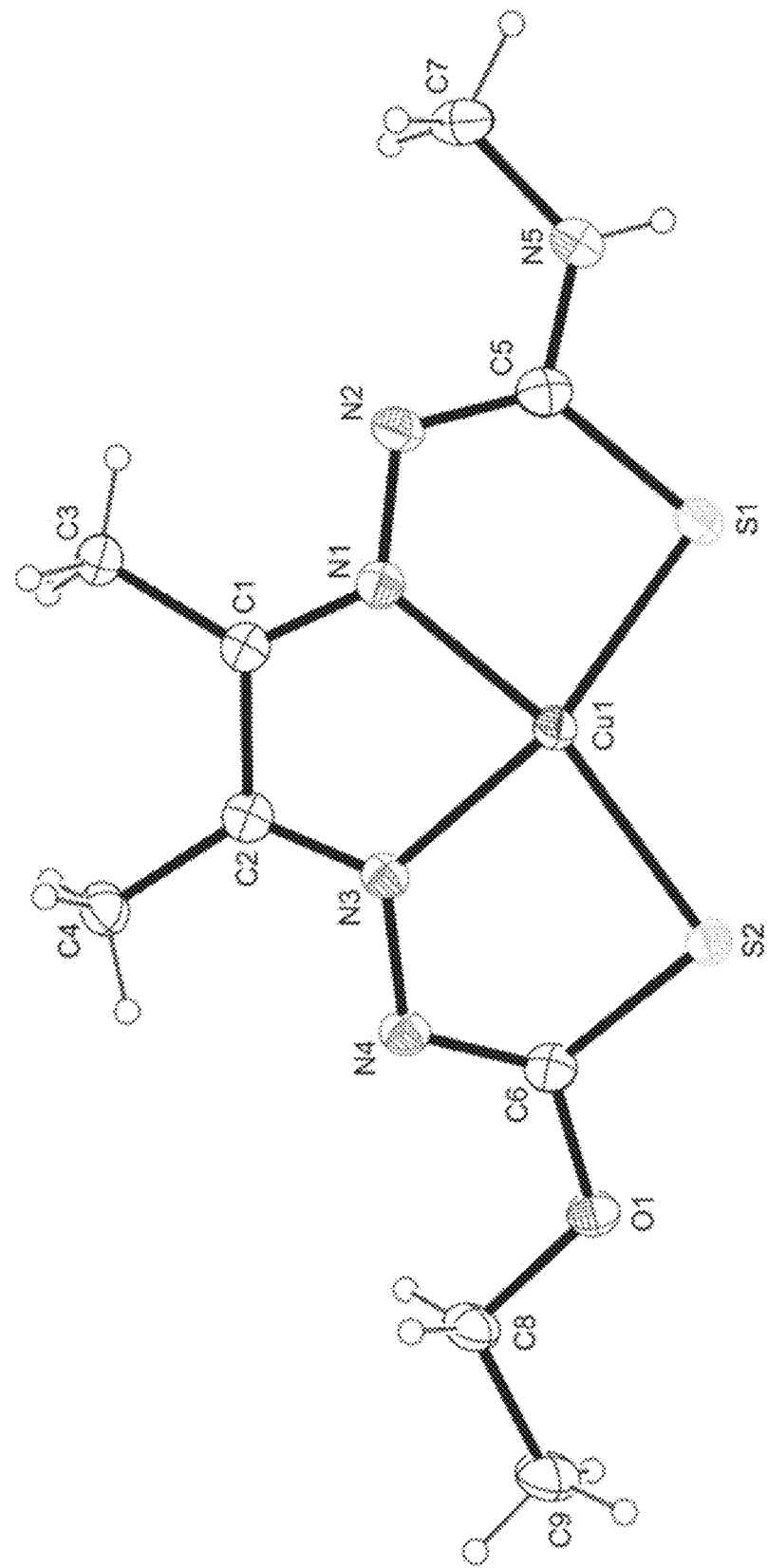
FIG. 34: An ORTEP representation of the product of reaction E (ethyl) which is compound I-1.

The ligand was suspended in methanol (0.354 g, 0.00129 mol). To this suspension copper (II) acetate monohydrate (0.285 g, 0.00149 mol) was added which caused an immediate color change of the suspension to red-brown. The suspension was refluxed for 4 hours then cooled to room temperature then filtered and washed with methanol. 0.220 g (51%) yield. Elemental analysis calculated: C: 32.08 H: 4.49 N: 20.79. Found: C: 31.53 H: 4.34 N: 20.26 Mass spec. calculated for $R_A$=—$CH_2CH_3$: 336.00141 found: 337.0080 (it appears to have picked up a proton in the mass spec). An ORTEP representation of the product of reaction E (ethyl) (compound I-1) is shown in FIG. 34.

Reaction E—$R_A$=Propyl

The ligand was suspended in methanol (0.373 g, 0.00129 mol). To this suspension copper (II) acetate monohydrate (0.285 g, 0.00149 mol) was added which caused an immediate color change of the suspension to red-brown. The suspension was refluxed for 4 hours then cooled to room temperature then filtered and washed with methanol. 0.200 g (44%) yield Calculated for $R_A$=—$CH_2CH_2CH_3$: C: 34.22 H: 4.88 N: 19.96. Found: C: 34.17 H: 4.83 N: 20.01. Mass spec. calculated: 350.01706 found: 351.0239 (it appears to have picked up a proton in the mass spec). This is compound I-9.

Reaction F

Figure 35:
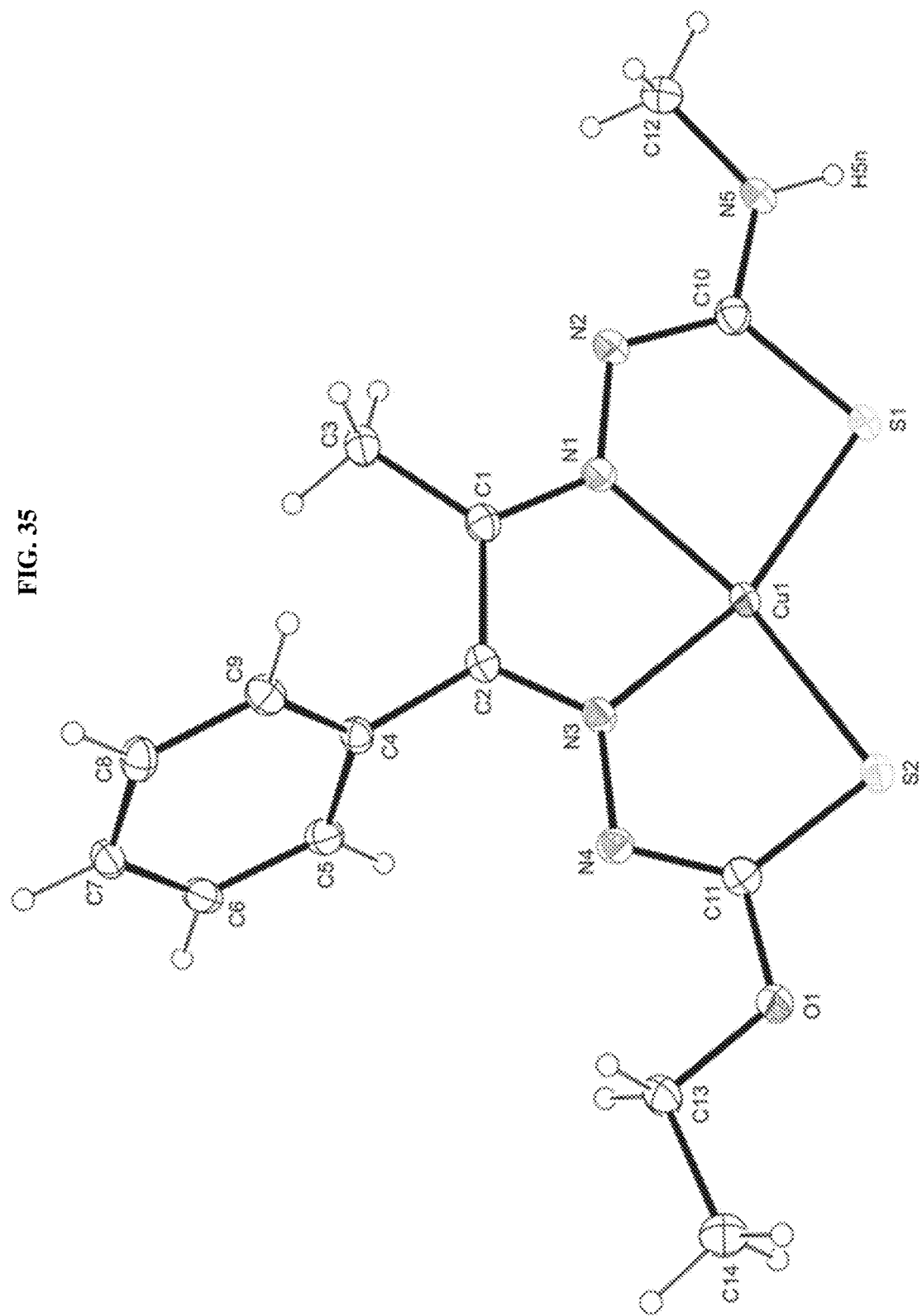
FIG. 35: An ORTEP representation of the product of reaction F which is compound I-5.

The ligand was suspended in methanol. To this suspension copper (II) acetate monohydrate was added which caused an immediate color change of the suspension to red-brown. The suspension was refluxed for 4 hours then cooled to room temperature then filtered and washed with methanol. 0.146 g (29%) yield. Elemental Analysis calculated: C: 42.14 H: 4.29 N: 17.55. Found: C: 41.84 H: 4.22 N: 17.53. Mass spec. calculated: 398.01706 found: 339.0238. (it appears to have picked up a proton in the mass spec). An ORTEP representation of the product of reaction F (compound I-5) is shown in FIG. 35.

Reaction G—Generic Preparation of Ni Compounds

The ligand was suspended in methanol (0.00129 mol). To this suspension nickel (II) acetate tetrahydrate (0.00149 mol) (Lancaster) was added which caused an immediate color change of the suspension to dark brown color. The suspension was refluxed for 4 hours then cooled to room temperature then stored in a freezer overnight. The following day the suspension was filtered cold and washed with methanol.

Characterization of compound I-6 prepared using Reaction G: Mass spec calculated 393.02281. Found 394.0295 (picked up a proton). Elemental analysis calculated C: 42.66 H: 4.35 N: 17.77 Found C: 42.85 H: 4.46 N: 17.57.

Reaction H—Generic Preparation of Zn Compounds

The ligand was suspended in methanol (0.00129 mol). To this suspension zinc (II) acetate dihydrate (0.00149 mol) (Fischer) was added which caused an immediate color change of the suspension to yellow-orange. The suspension was refluxed for 4 hours then cooled to room temperature then filtered and washed with methanol.

Characterization of compound I-3 prepared using Reaction H: Mass spec calculated 337.00096 Found 338.2153 (picked up a proton). Elemental analysis calculated C: 31.91 H: 4.46 N: 20.67. Found C: 31.92 H: 4.45 N: 20.67.

Characterization of compound I-7 prepared using Reaction H: Mass spec calculated 399.01661. Found 400.3753 (picked up a proton). Elemental analysis calculated: C: 41.95 H: 4.27 N: 17.47. Found: C: 40.65 H: 4.08 N: 19.97.

Example Set C—Additional Embodiments

1. A compound selected from
(a) Formula (Ia)

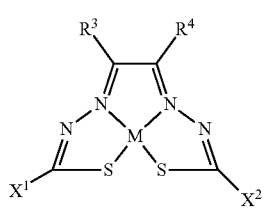

(Ia)

and salts, optical isomers, geometric isomers, salts of isomers, and derivatives thereof; and
(b) Formula (Ib)

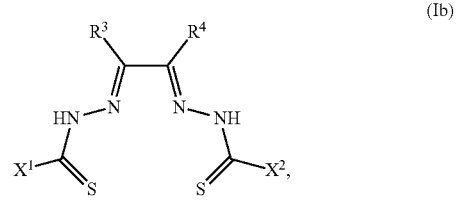

(Ib)

and salts, optical isomers, geometric isomers, salts of isomers, and derivatives thereof;
wherein
$X^1$ is —$N(R^{1a})(R^{1b})$ or —$O(R^{1c})$
$X^2$ is —$N(R^{2a})(R^{2b})$ or —$O(R^{2c})$
$R^{1a}$ is H, halogen, —CN, hydroxy (—OH), methanoyl (—COH), carboxy (—$CO_2H$), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl, which methanoyl (—COH), carboxy (—$CO_2H$), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl can optionally be substituted with one or more of halogen, oxo (=O), hydroxy (—OH), methanoyl (—COH), carboxy (—$CO_2H$), nitro (—$NO_2$), —$NH_2$, —$N(CH_3)_2$, cyano (—CN), ethynyl (—CCH), propynyl, sulfo (—$SO_3H$), morpholinyl, —CO-morpholin-4-yl, phenyl, —$CONH_2$, —$CON(CH_3)_2$, $C_1$-$C_3$ alkyl, $C_1$-$C_3$ perfluoronated alkyl, —$CF_3$, —$OCF_3$, or $C_1$-$C_3$ alkoxy;
$R^{1b}$ is H, halogen, —CN, hydroxy (—OH), methanoyl (—COH), carboxy (—$CO_2H$), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl, which methanoyl (—COH), carboxy (—$CO_2H$), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl can optionally be substituted with one or more of halogen, oxo (=O), hydroxy (—OH), methanoyl (—COH), carboxy (—$CO_2H$), nitro (—$NO_2$), —$NH_2$, —$N(CH_3)_2$, cyano (—CN), ethynyl (—CCH), propynyl, sulfo (—$SO_3H$), morpholinyl, —CO-morpholin-4-yl, phenyl, —$CONH_2$, —$CON(CH_3)_2$, $C_1$-$C_3$ alkyl, $C_1$-$C_3$ perfluoronated alkyl, —$CF_3$, —$OCF_3$, or $C_1$-$C_3$ alkoxy;
$R^{1c}$ is H, halogen, —CN, hydroxy (—OH), methanoyl (—COH), carboxy (—$CO_2H$), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl, which methanoyl (—COH), carboxy (—$CO_2H$), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl can optionally be substituted with one or more of halogen, oxo (=O), hydroxy (—OH), methanoyl (—COH), carboxy (—$CO_2H$), nitro (—$NO_2$), —$NH_2$, —$N(CH_3)_2$, cyano (—CN), ethynyl (—CCH), propynyl, sulfo (—$SO_3H$), morpholinyl, —CO-morpholin-4-yl, phenyl, —$CONH_2$, —$CON(CH_3)_2$, $C_1$-$C_3$ alkyl, $C_1$-$C_3$ perfluoronated alkyl, —$CF_3$, —$OCF_3$, or $C_1$-$C_3$ alkoxy;
$R^{1a}$ and $R^{1b}$ are optionally bonded together with their attached nitrogen to form heterocyclyl or heteroaryl, which heterocyclyl or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy;

R$^{2a}$ is H, halogen, —CN, hydroxy (—OH), methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl, which methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl can optionally be substituted with one or more of halogen, oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy;

R$^{2b}$ is H, halogen, —CN, hydroxy (—OH), methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl, which methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl can optionally be substituted with one or more of halogen, oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy;

R$^{2c}$ is H, halogen, —CN, hydroxy (—OH), methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl, which methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl can optionally be substituted with one or more of halogen, oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy;

R$^{2a}$ and R$^{2b}$ are optionally bonded together with their attached nitrogen to form heterocyclyl or heteroaryl, which heterocyclyl or heteroaryl can optionally be substituted with one or more of halogen, oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy;

R$^3$ is H, halogen, —CN, hydroxy (—OH), methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl, which methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl can optionally be substituted with one or more of halogen, oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy;

R$^4$ is H, halogen, —CN, hydroxy (—OH), methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl, which methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl can optionally be substituted with one or more of halogen, oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy;

R$^3$ and R$^4$ are optionally bonded together to form a ring with their attached carbons that is fused to the attached carbons of R$^3$ and R$^4$, where the ring that is fused is cycloalkyl, heterocyclyl, aryl, or heteroaryl, which cycloalkyl, heterocyclyl, aryl, or heteroaryl can optionally be substituted with one or more of halogen, oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy; and M is a metal (e.g., divalent cation), or any of the compounds disclosed herein.

2. The compound of embodiment 1, wherein (a) X$^1$ is —N(H)(CH$_3$), —N(CH$_3$)$_2$, —N(H)(CH$_2$CF$_3$), —N(H)(phenyl), —N(H)(methoxyphenyl), —N(H)(4-methoxyphenyl), —OCH$_3$, —OCH$_2$CH$_3$, —OCH$_2$CH$_2$CH$_3$, —OCH(CH$_3$)$_2$, or —OC$_8$H$_{17}$, (b) X$^2$ is —N(H)(CH$_3$), —N(CH$_3$)$_2$, —N(H)(CH$_2$CF$_3$), —N(H)(phenyl), —N(H)(methoxyphenyl), —N(H)(4-methoxyphenyl), —OCH$_3$, —OCH$_2$CH$_3$, —OCH$_2$CH$_2$CH$_3$, —OCH(CH$_3$)$_2$, or —OC$_8$H$_{17}$, (c) R$^3$ is —CH$_3$, —CH$_2$CH$_3$, or —C$_6$H$_5$, (d) R$^4$ is —CH$_3$, —CH$_2$CH$_3$, or —C$_6$H$_5$, or (e) R$^3$ and R$^4$ are the same, or a combination thereof.

3. The compound of embodiment 1 or embodiment 2, wherein, (a) X$^1$ and X$^2$ are the same, (b) X$^1$ is —N(R$^{1a}$)(R$^{1b}$) and X$^2$ is —O(R$^{2c}$), or (c) X$^1$ is —O(R$^{1c}$) and X$^2$ is —N(R$^{2a}$)(R$^{2b}$).

4. The compound of any of embodiments 1-3, wherein M is Ni, Pd, Pt, Cu, Ag, Au, Zn, Cd, Hg, Co, Rh, Ti, V, Cr, Mn, or Fe, preferably Cu$^{2+}$, Cu$^+$, Zn$^{2+}$, Co$^{2+}$, Ni$^{2+}$, or Pt, more preferably Cu$^{2+}$, Zn$^{2+}$, or Ni$^{2+}$.

5. The compound of any of embodiments 1-4, wherein the compound is selected from

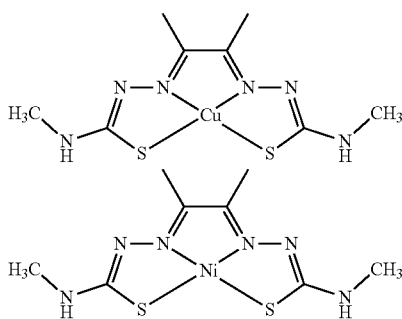

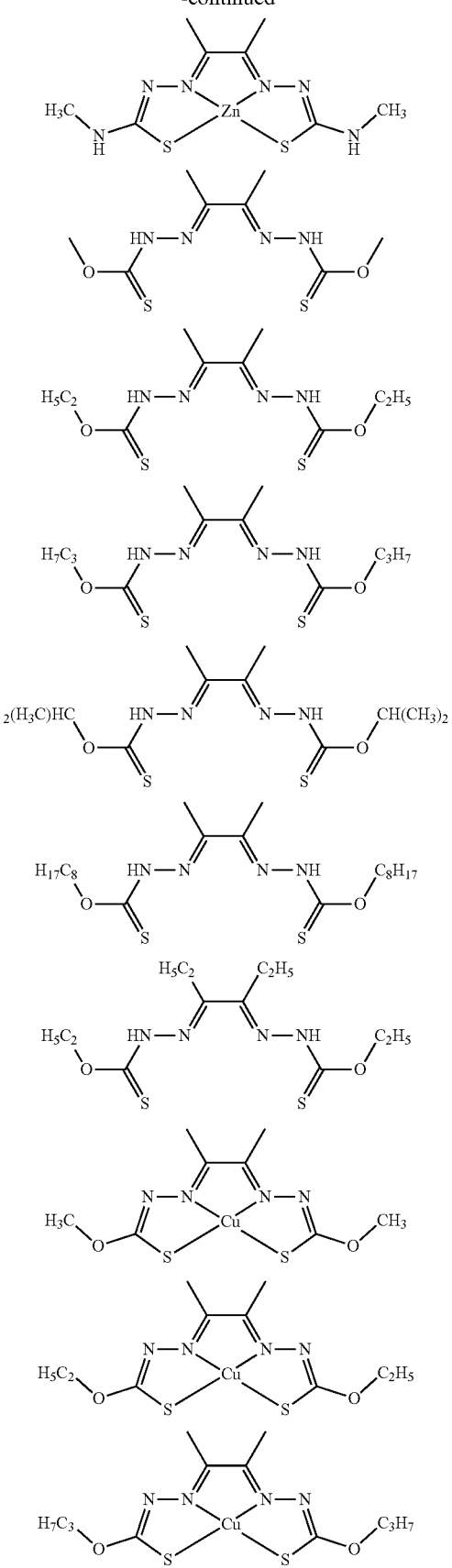
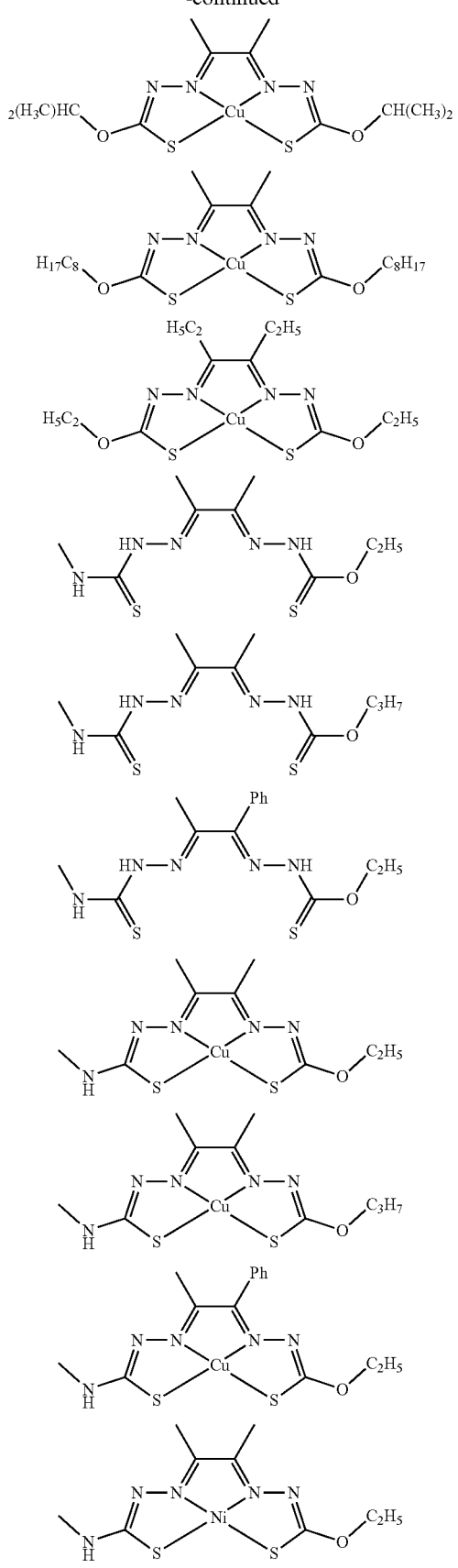

-continued

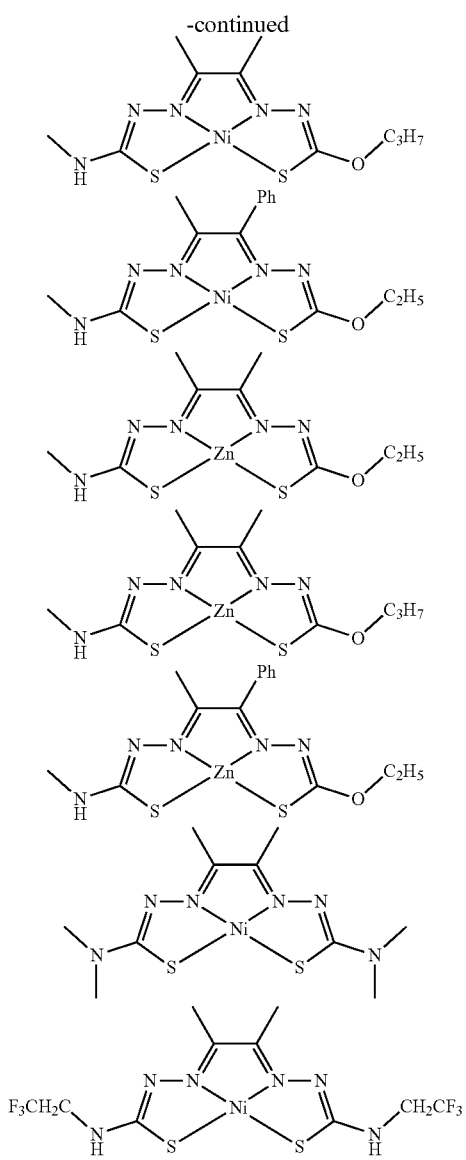

6. A composition (e.g., pharmaceutical composition) comprising the compound of any of embodiments 1-5 or any composition disclosed herein.

7. A method for treating cancer in an animal (e.g., a human) comprising
administering to an animal the compound of any of embodiments 1-5 or any compound disclosed herein, or the composition of claim 6.

8. The method of embodiment 7, wherein the animal is a human, livestock, pet, cat, dog, cattle, pig, chicken, or turkey.

9. The method of embodiment 7 or embodiment 8, wherein the cancer is selected from the group consisting of carcinomas, sarcomas, hematologic cancers, neurological malignancies, basal cell carcinoma, thyroid cancer, neuroblastoma, ovarian cancer, melanoma, renal cell carcinoma, hepatocellular carcinoma, breast cancer, colon cancer, lung cancer, pancreatic cancer, brain cancer, prostate cancer, chronic lymphocytic leukemia, acute lymphoblastic leukemia, rhabdomyosarcoma, Glioblastoma multiforme, meningioma, bladder cancer, gastric cancer, Glioma, oral cancer, nasopharyngeal carcinoma, kidney cancer, rectal cancer, lymph node cancer, bone marrow cancer, stomach cancer, uterine cancer, leukemia, basal cell carcinoma, cancers related to epithelial cells, and tumors associated with any of the aforementioned cancer types.

10. The method of any of embodiments 7-9, wherein the cancer is selected from the group consisting of ovarian cancer, breast cancer, colon cancer, melanoma, renal cell carcinoma, lung cancer, brain cancer, prostate cancer, and tumors associated with any of the aforementioned cancer types.

11. A method for synthesizing (e.g., as disclosed herein) a compound of any embodiments 1-5.

12. A catalyst or an electrocatalyst (e.g., as disclosed herein) comprising a composition comprising a compound of any of embodiments 1-5.

13. An electrochemical cell (e.g., as disclosed herein) comprising a composition comprising a compound of any of embodiments 1-5.

14. The electrochemical cell of claim 13, wherein the cathode of the electrochemical cell comprises the composition.

15. A method for producing $H_2$ (e.g., as disclosed herein) comprising contacting, in an electrochemical cell, a first composition comprising a compound of any of embodiments 1-5, with a second composition comprising water.

16. The method of claim 15, wherein the cathode of the electrochemical cell comprises the first composition.

Example Set D—Further Embodiments

1. A compound selected from
(a) Formula (Ia)

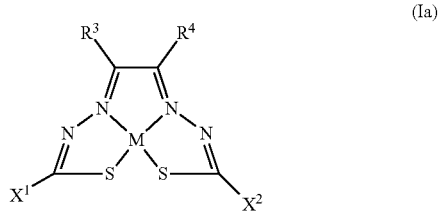

and salts, optical isomers, geometric isomers, salts of isomers, and derivatives thereof; and
(b) Formula (Ib)

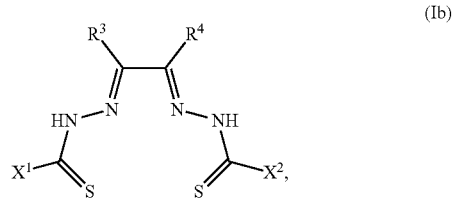

and salts, optical isomers, geometric isomers, salts of isomers, and derivatives thereof;
wherein
$X^1$ is —$N(R^{1a})(R^{1b})$ or —$O(R^{1c})$
$X^2$ is —$N(R^{2a})(R^{2b})$ or —$O(R^{2c})$
$R^{1a}$ is H, halogen, —CN, hydroxy (—OH), methanoyl (—COH), carboxy (—$CO_2H$), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl, which methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl can optionally be substituted with one or more of halogen, oxo (═O), hydroxy (—OH), methanoyl (—COH), carboxy (—CO$_2$H), nitro (—NO$_2$), —NH$_2$, —N(H)(C$_1$-C$_4$ alkyl), —N(C$_1$-C$_4$ alkyl)(C$_1$-C$_4$ alkyl), —N$^+$(C$_1$-C$_4$ alkyl)(C$_1$-C$_4$ alkyl)(C$_1$-C$_4$ alkyl), —N(H)(CH$_3$), —N(CH$_3$)$_2$, —N$^+$(CH$_3$)$_3$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy;

R$^{1b}$ is H, halogen, —CN, hydroxy (—OH), methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl, which methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl can optionally be substituted with one or more of halogen, oxo (═O), hydroxy (—OH), methanoyl (—COH), carboxy (—CO$_2$H), nitro (—NO$_2$), —NH$_2$, —N(H)(C$_1$-C$_4$ alkyl), —N(C$_1$-C$_4$ alkyl)(C$_1$-C$_4$ alkyl), —N$^+$(C$_1$-C$_4$ alkyl)(C$_1$-C$_4$ alkyl)(C$_1$-C$_4$ alkyl), —N(H)(CH$_3$), —N(CH$_3$)$_2$, —N$^+$(CH$_3$)$_3$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy;

R$^{1c}$ is H, halogen, —CN, hydroxy (—OH), methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl, which methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl can optionally be substituted with one or more of halogen, oxo (═O), hydroxy (—OH), methanoyl (—COH), carboxy (—CO$_2$H), nitro (—NO$_2$), —NH$_2$, —N(H)(C$_1$-C$_4$ alkyl), —N(C$_1$-C$_4$ alkyl)(C$_1$-C$_4$ alkyl), —N$^+$(C$_1$-C$_4$ alkyl)(C$_1$-C$_4$ alkyl)(C$_1$-C$_4$ alkyl), —N(H)(CH$_3$), —N(CH$_3$)$_2$, —N$^+$(CH$_3$)$_3$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy;

R$^{1a}$ and R$^{1b}$ are optionally bonded together with their attached nitrogen to form heterocyclyl or heteroaryl, which heterocyclyl or heteroaryl can optionally be substituted with one or more of halogen, oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy;

R$^{2a}$ is H, halogen, —CN, hydroxy (—OH), methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl, which methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl can optionally be substituted with one or more of halogen, oxo (═O), hydroxy (—OH), methanoyl (—COH), carboxy (—CO$_2$H), nitro (—NO$_2$), —NH$_2$, —N(H)(C$_1$-C$_4$ alkyl), —N(C$_1$-C$_4$ alkyl)(C$_1$-C$_4$ alkyl), —N$^+$(C$_1$-C$_4$ alkyl)(C$_1$-C$_4$ alkyl)(C$_1$-C$_4$ alkyl), —N(H)(CH$_3$), —N(CH$_3$)$_2$, —N$^+$(CH$_3$)$_3$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy;

R$^{2b}$ is H, halogen, —CN, hydroxy (—OH), methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl, which methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl can optionally be substituted with one or more of halogen, oxo (═O), hydroxy (—OH), methanoyl (—COH), carboxy (—CO$_2$H), nitro (—NO$_2$), —NH$_2$, —N(H)(C$_1$-C$_4$ alkyl), —N(C$_1$-C$_4$ alkyl)(C$_1$-C$_4$ alkyl), —N$^+$(C$_1$-C$_4$ alkyl)(C$_1$-C$_4$ alkyl)(C$_1$-C$_4$ alkyl), —N(H)(CH$_3$), —N(CH$_3$)$_2$, —N$^+$(CH$_3$)$_3$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy;

R$^{2c}$ is H, halogen, —CN, hydroxy (—OH), methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl, which methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl can optionally be substituted with one or more of halogen, oxo (═O), hydroxy (—OH), methanoyl (—COH), carboxy (—CO$_2$H), nitro (—NO$_2$), —NH$_2$, —N(H)(C$_1$-C$_4$ alkyl), —N(C$_1$-C$_4$ alkyl)(C$_1$-C$_4$ alkyl), —N$^+$(C$_1$-C$_4$ alkyl)(C$_1$-C$_4$ alkyl)(C$_1$-C$_4$ alkyl), —N(H)(CH$_3$), —N(CH$_3$)$_2$, —N$^+$(CH$_3$)$_3$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy;

R$^{2a}$ and R$^{2b}$ are optionally bonded together with their attached nitrogen to form heterocyclyl or heteroaryl, which heterocyclyl or heteroaryl can optionally be substituted with one or more of halogen, oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy;

R$^3$ is H, halogen, —CN, hydroxy (—OH), methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl, which methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl can optionally be substituted with one or more of halogen, oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy;

R$^4$ is H, halogen, —CN, hydroxy (—OH), methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl, which methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl can optionally be substituted with one or more of halogen, oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy;

R$^3$ and R$^4$ are optionally bonded together to form a ring with their attached carbons that is fused to the attached carbons of R$^3$ and R$^4$, where the ring that is fused is cycloalkyl, heterocyclyl, aryl, or heteroaryl, which cycloalkyl, heterocyclyl, aryl, or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy; and M is a metal (e.g., divalent cation), or any of the compounds disclosed herein.

2. The compound of embodiment 1, wherein (a) X$^1$ is —N(H)(CH$_3$), —N(CH$_3$)$_2$, —N(H)(CH$_2$CF$_3$), —N(H)(CH$_2$CH$_2$N(CH$_3$)$_2$), —N(H)(CH$_2$CH$_2$N$^+$(CH$_3$)$_3$), —N(H)(phenyl), —N(H)(methoxyphenyl), —N(H)(4-methoxyphenyl), —OCH$_3$, —OCH$_2$CH$_3$, —OCH$_2$CH$_2$CH$_3$, —OCH(CH$_3$)$_2$, or —OC$_8$H$_{17}$, (b) X$^2$ is —N(H)(CH$_3$), —N(CH$_3$)$_2$, —N(H)(CH$_2$CF$_3$), —N(H)(CH$_2$CH$_2$N(CH$_3$)$_2$), —N(H)(CH$_2$CH$_2$N$^+$(CH$_3$)$_3$), —N(H)(phenyl), —N(H)(methoxyphenyl), —N(H)(4-methoxyphenyl), —OCH$_3$, —OCH$_2$CH$_3$, —OCH$_2$CH$_2$CH$_3$, —OCH(CH$_3$)$_2$, or —OC$_8$H$_{17}$, (c) R$^3$ is —CH$_3$, —CH$_2$CH$_3$, or —C$_6$H$_5$, (d) R$^4$ is —CH$_3$, —CH$_2$CH$_3$, or —C$_6$H$_5$, or (e) R$^3$ and R$^4$ are the same, or a combination thereof.

3. The compound of embodiment 1 or embodiment 2, wherein, (a) X$^1$ and X$^2$ are the same, (b) X$^1$ is —N(R$^{1a}$)(R$^{1b}$) and X$^2$ is —O(R$^{2c}$), or (c) X$^1$ is —O(R$^{1c}$) and X$^2$ is —N(R$^{2a}$)(R$^{2b}$).

4. The compound of any of embodiments 1-3, wherein M is Ni, Pd, Pt, Cu, Ag, Au, Zn, Cd, Hg, Co, Rh, Ti, V, Cr, Mn, or Fe, preferably Cu$^{2+}$, Cu$^+$, Zn$^{2+}$, Co$^{2+}$, Ni$^{2+}$, or Pt, more preferably Cu$^{2+}$, Zn$^{2+}$, or Ni$^{2+}$.

5. The compound of any of embodiments 1-4, wherein the compound is selected from

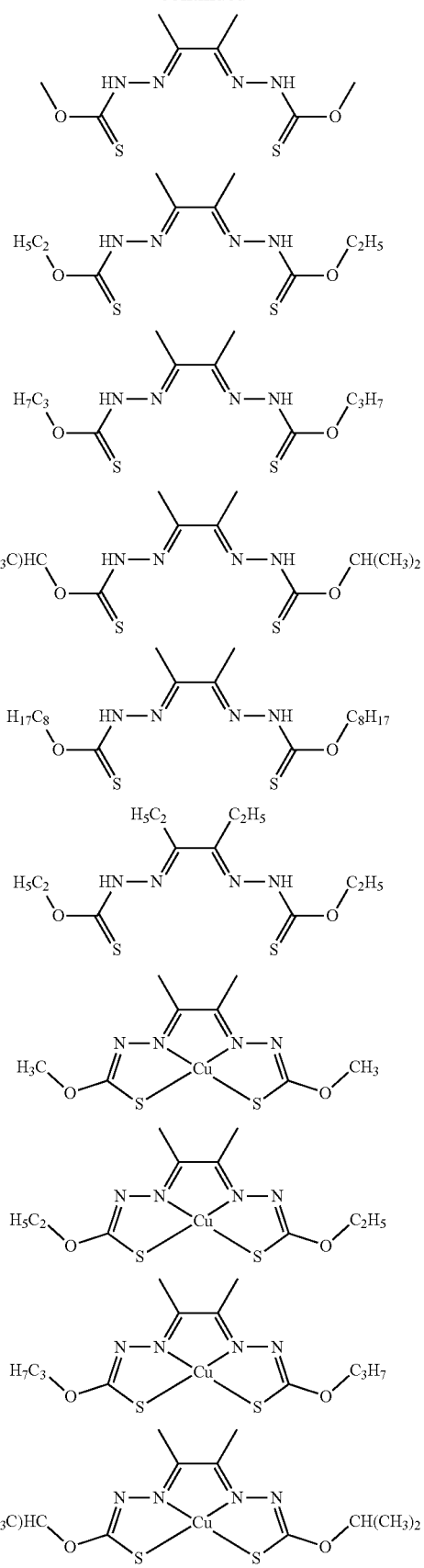

-continued

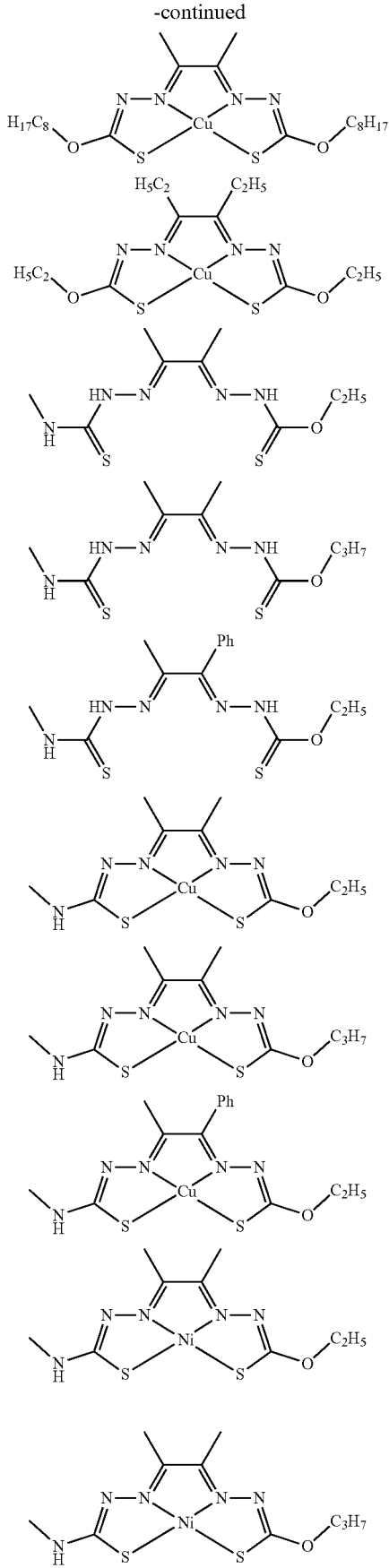

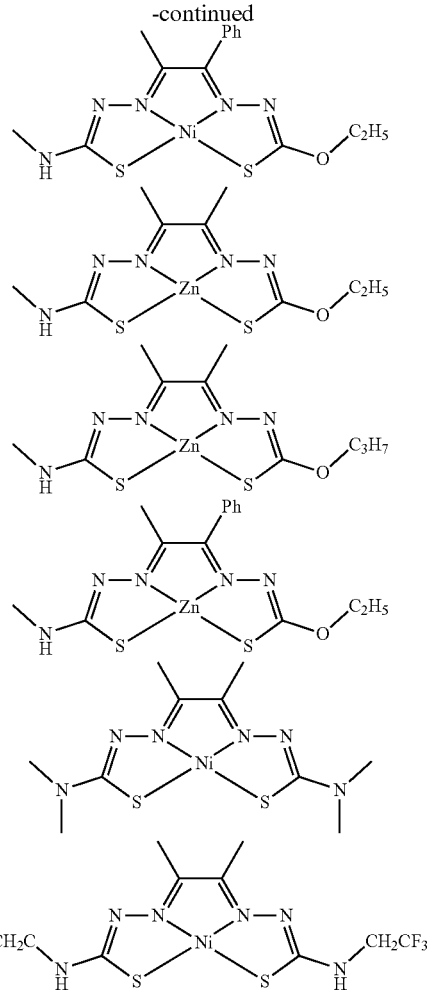

6. The compound of any of embodiments 1-5, wherein the compound of Formula (I) is I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-53, I-54, I-55, I-56, I-57, I-58, I-59, I-60, I-61, I-62, I-63, I-64, I-65, I-66, I-67, I-68, I-69, I-70, I-71, I-72, I-73, I-74, I-75, I-76, I-77, I-78, I-79, I-80, I-81, I-82, or I-83.

7. The compound of any of embodiments 1-6, wherein the compound of Formula (I) is I-1, I-3, I-4, I-5, I-7, I-8, I-9, I-11, I-12, or I-22.

8. The compound of any of embodiments 1-7, wherein the compound of Formula (I) is I-1 or I-5.

9. A composition comprising a compound of any of embodiments 1-8.

10. The composition of embodiment 9, wherein the amount of the compound is from about 0.0001% (by weight total composition) to about 99%.

11. The composition of embodiment 9 or embodiment 10, further comprising a formulary ingredient, an adjuvant, or a carrier.

12. A pharmaceutical composition comprising a compound of any of embodiments 1-8.

13. The pharmaceutical composition of embodiment 12, wherein the amount of the compound is from about 0.0001% (by weight total composition) to about 50%.

14. The pharmaceutical composition of embodiment 12 or embodiment 13, further comprising a formulary ingredient, an adjuvant, or a carrier.

15. A method for providing an animal with a compound comprising one or more administrations of one or more compositions comprising the compound of any of embodiments 1-8, wherein the compositions may be the same or different if there is more than one administration.

16. The method of embodiment 15, wherein at least one of the one or more compositions further comprises a formulary ingredient.

17. The method of embodiment 15 or embodiment 16, wherein at least one of the one or more compositions comprises the composition of any of embodiments 9-11 or the pharmaceutical composition of any of embodiments 12-14.

18. The method of any of embodiments 15-17, wherein at least one of the one or more administrations comprises parenteral administration, a mucosal administration, intravenous administration, subcutaneous administration, topical administration, intradermal administration, oral administration, sublingual administration, intranasal administration, or intramuscular administration.

19. The method of any of embodiments 15-18, wherein if there is more than one administration at least one composition used for at least one administration is different from the composition of at least one other administration.

20. The method of any of embodiments 15-19, wherein the compound of at least one of the one or more compositions is administered to the animal in an amount of from about 0.01 mg/kg animal body weight to about 15 mg/kg animal body weight.

21. The method of any of embodiments 15-20, wherein the animal is a human, a rodent, or a primate.

22. A method for treating an animal for a disease, comprising one or more administrations of one or more compositions comprising the compound of any of claims 1-8, wherein the compositions may be the same or different if there is more than one administration.

23. The method of embodiment 22, wherein at least one of the one or more compositions further comprises a formulary ingredient.

24. The method of embodiment 22 or embodiment 23, wherein at least one of the one or more compositions comprises the composition of any of embodiments 9-11 or the pharmaceutical composition of any of embodiments 12-14.

25. The method of any of embodiments 22-24, wherein at least one of the one or more administrations comprises parenteral administration, a mucosal administration, intravenous administration, subcutaneous administration, topical administration, intradermal administration, oral administration, sublingual administration, intranasal administration, or intramuscular administration.

26. The method of any of embodiments 22-25, wherein if there is more than one administration at least one composition used for at least one administration is different from the composition of at least one other administration.

27. The method of any of embodiments 22-26, wherein the compound of at least one of the one or more compositions is administered to the animal in an amount of from about 0.005 mg/kg animal body weight to about 50 mg/kg animal body weight.

28. The method of any of embodiments 22-27, wherein the animal is a human, a rodent, or a primate.

29. The method of any of embodiments 22-28, wherein the animal is in need of the treatment.

30. The method of any of embodiments 22-29, wherein the method is for treating cancer.

31. The method of any of embodiments 22-30, wherein the method is for treating acute lymphoblastic leukemia, astrocytoma, basal cell carcinoma, bladder cancer, bone marrow cancer, breast cancer, chronic lymphocytic leukemia (CLL), CNS cancer, colon cancer, colorectal cancer, endometrial cancer, gastric cancer, glioblastoma, glioblastoma multiforme, glioma, gliosarcoma, hepatocellular carcinoma, kidney cancer, leukemia, liver cancer, lung cancer, lymphoma, melanoma, malignant nerve sheath tumors, medulloblastoma, meningioma, multiple myeloma, nasopharyngeal carcinoma, neuroblastoma, non-Hodgkin lymphoma, non-small cell lung cancer, oral cancer, ovarian cancer, pancreatic cancer, prostate cancer, rectal cancer, renal cancer, renal cell carcinoma, rhabdomyosarcoma, squamous cell carcinoma, stomach cancer, thyroid cancer, uterine cancer, cancers that can result in metastasis, cancers resulting from metastasis, or cancerous tumors thereof.

32. The method of any of embodiments 22-31, wherein the method is for treating leukemia, lung cancer, non-small cell lung cancer, colorectal cancer, colon cancer, rectal cancer, CNS cancer, glioblastoma, glioblastoma multiforme, gliosarcoma, astrocytoma, melanoma, cutaneous malignant melanoma, melanoma tumorigenesis, ovarian cancer, kidney cancer, prostate cancer, breast cancer, or cancerous tumors thereof.

33. The method of any of embodiments 22-32, wherein the method does not include treating leukemia.

34. The method of any of embodiments 22-33, wherein the method is for treating lung cancer, non-small cell lung cancer, colorectal cancer, colon cancer, rectal cancer, CNS cancer, glioblastoma, glioblastoma multiforme, gliosarcoma, astrocytoma, melanoma, cutaneous malignant melanoma, melanoma tumorigenesis, ovarian cancer, kidney cancer, prostate cancer, breast cancer, or cancerous tumors thereof.

35. The method of any of embodiments 22-34, wherein the method is for treating cancerous tumors.

36. A method for preparing a compound of any of embodiments 1-8 using any suitable method including but not limited to those disclosed herein.

37. A method for preparing a compound of any of embodiments 1-8 comprising,
(a) reacting a compound of Formula (II) with a compound of Formula (III) to result in a mixture comprising a compound of Formula (IV) and
(b) reacting a compound of Formula (IV) with a compound of Formula (V) to result in a mixture comprising a compound of Formula (Ib),
wherein Formula (II) is

Formula (III) is

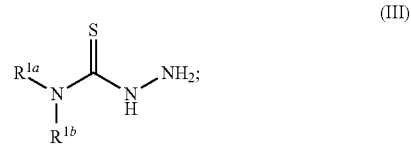

Formula (IV) is

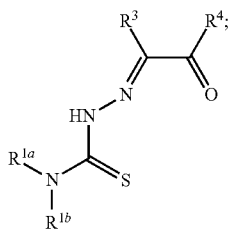

and
Formula (V) is

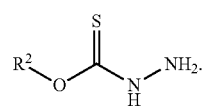

38. The method of embodiment 37, wherein the method further comprises recovering the compound of Formula (Ib).

39. The method of embodiment 37 or embodiment 38, wherein the method further comprises
   (c) reacting the compound of Formula (Ib) with a compound of Formula (VI) and
   (d) recovering a compound of Formula (Ia), wherein Formula (VI) is M:anion (VI).

40. The method of embodiment 39, wherein the anion is a weak base, acetate, acetate monohydrate, acetate dihydrate, or acetate tetrahydrate.

41. The method of embodiment 39 or embodiment 40, wherein the compound of Formula (VI) is copper (II) acetate monohydrate, nickel (II) acetate tetrahydrate, or zinc (II) acetate dihydrate.

42. A catalyst or an electrocatalyst (e.g., as disclosed herein) comprising a composition comprising a compound of any of embodiments 1-8.

43. An electrochemical cell (e.g., as disclosed herein) comprising a composition comprising a compound of any of embodiments 1-8.

44. The electrochemical cell of claim 43, wherein the cathode of the electrochemical cell comprises the composition.

45. A method for producing $H_2$ (e.g., as disclosed herein) comprising contacting, in an electrochemical cell, a first composition comprising a compound of any of embodiments 1-8, with a second composition comprising water.

46. The method of claim 45, wherein the cathode of the electrochemical cell comprises the first composition.

Example Set E

A549 (human lung adenocarcinoma) cells and MDA-MB-231 (human breast adenocarcinoma) cells were cultured in DMEM medium containing 10% FBS and 1% Penicillin/Streptomycin. IMR-90 (human non-malignant lung fibroblast) cells were cultured in EMEM medium containing 10% FBS and 1% Penicillin/Streptomycin. Anti-proliferative activity of the indicated compounds was evaluated for A549 cells, MDA-MB-231 cells, and IMR-90 cells using a previously published 3-(4,5-dimethylthiazol-2-yl)-2,5-diphenyltetrazolium bromide (MTT) assay protocol (MORGAN, "Tetrazolium (MTT) Assay For Cellular Viability And Activity" Methods Mol. Biol. (1998) Vol. 79, pp. 179-183; BATES et al., "Antiproliferative Activity of G-rich Oligonucleotides Correlates with Protein Binding" J. Biol. Chem. (1999) Vol. 274, No. 37, pp. 26369-26377; SALIPUR et al., "A Novel Small Molecule That Induces Oxidative Stress And Selectively Kills Malignant Cells" Free Radical Biology and Medicine (2014) Vol. 68, pp. 110-121. Cells were seeded in quadruplicate wells in 96-well plates and allowed to adhere overnight. After 72 hrs of treatment with test compounds, MTT (Sigma, St. Louis, Mo.) was added for 4 hrs prior to cell lysis. Each assay was performed in at least triplicate. Cell death (% viability) was assessed by trypan blue exclusion; average of one experiment performed in duplicate wells ±SEM displayed.

Figure 36:
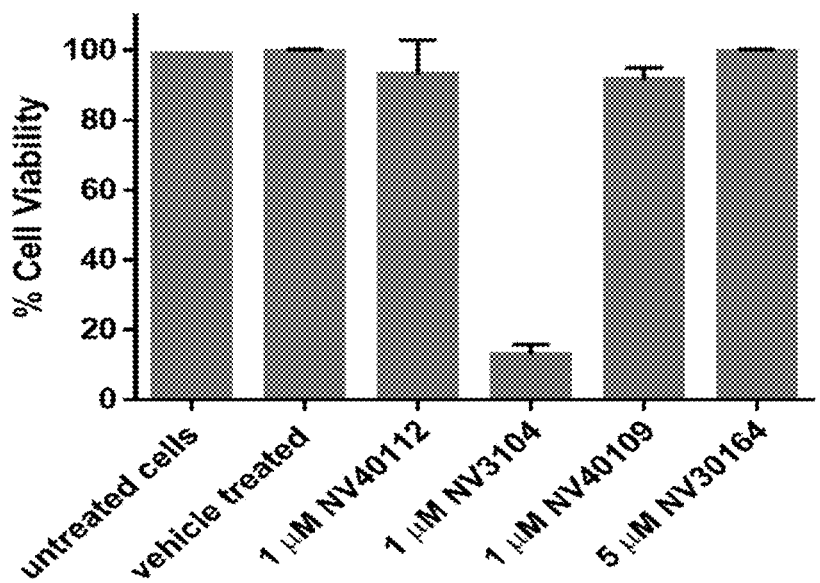
FIG. 36: Top Panel: Cell survival assays of A549 lung cancer cells for compounds (I-1 (NV3104), (1-4 (NV40112), I-3 (NV40109), and I-14 (NV30164)). Bottom Panel: Cell proliferation assays for MDA-MB-231 breast cancer cells for compounds (I-1 (NV3104), (1-4 (NV40112), I-3 (NV40109), and I-14 (NV30164)).
Figure 36:
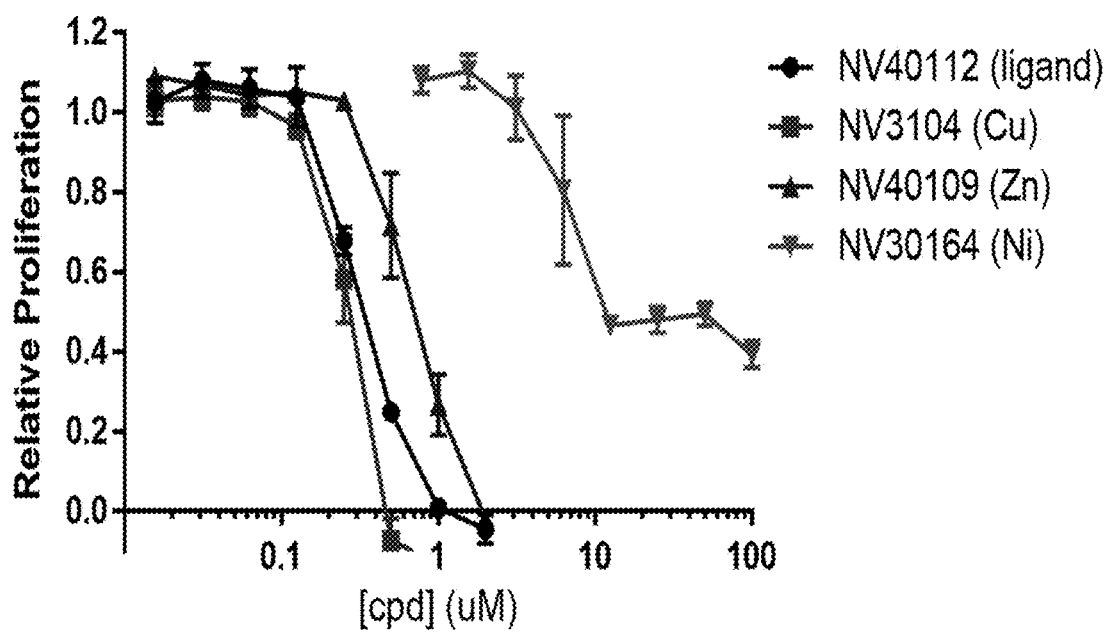
Figure 37:
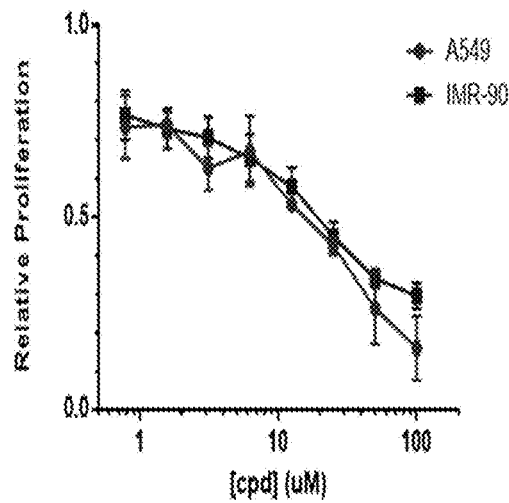
FIG. 37: Cell proliferation assays for A549 lung cancer cells for several compounds (L1, L2, L1C, and L2C2).
Figure 37:
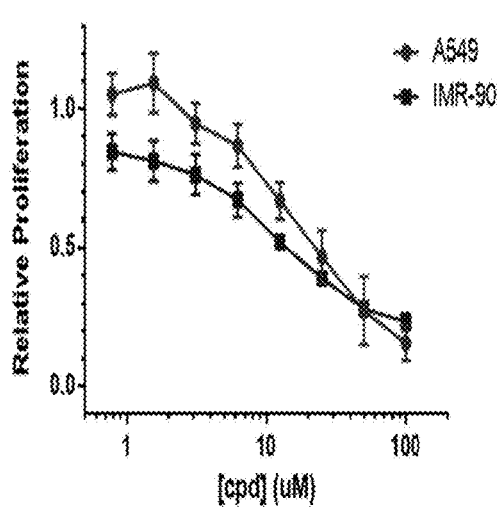
Figure 37:
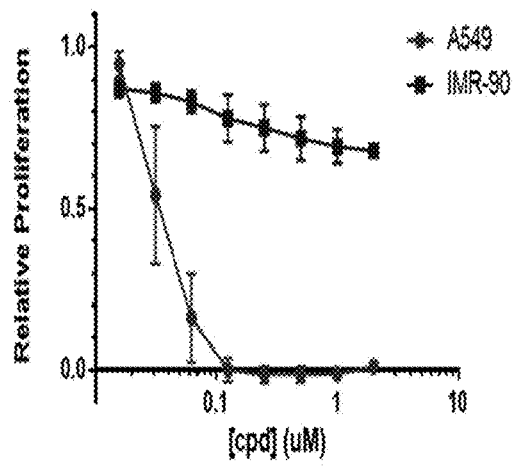
Figure 37:
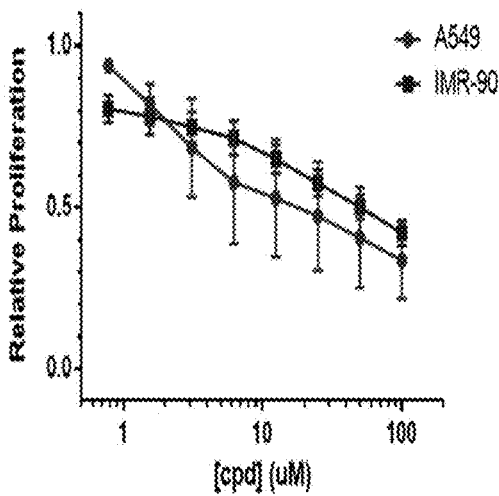
Figure 38:
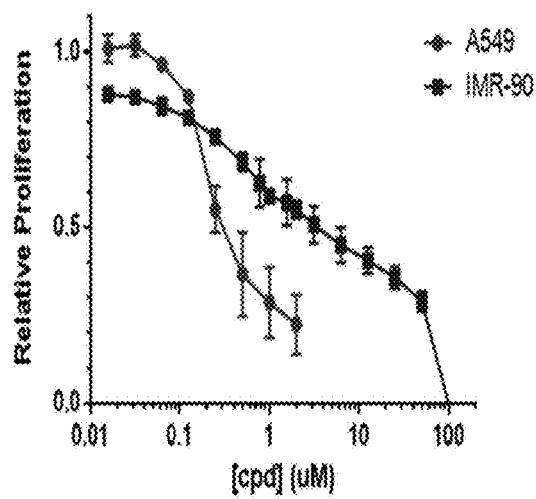
FIG. 38: Cell proliferation assays for A549 lung cancer cells for several compounds (ZnL1, ZnL2, ZnL1C, and ZnL2C2).
Figure 38:
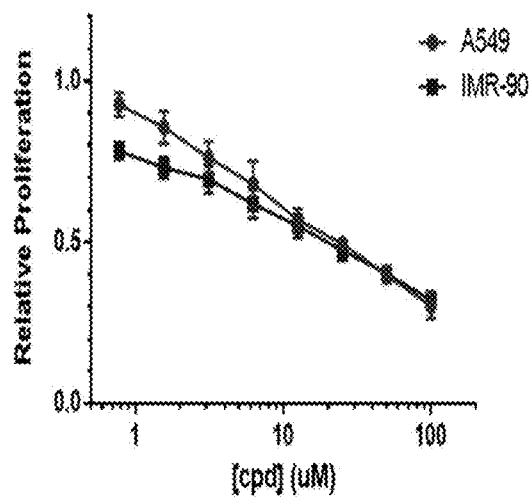
Figure 38:
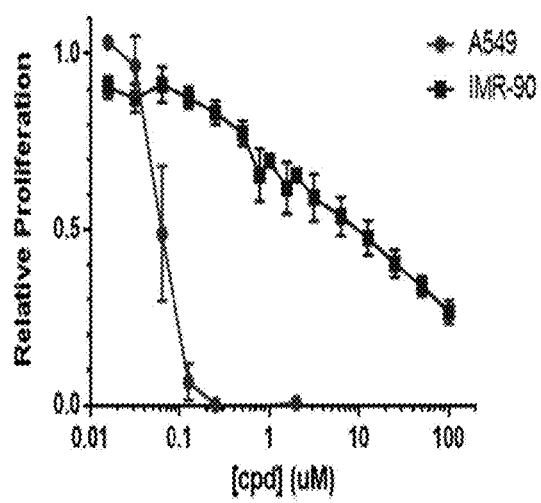
Figure 38:
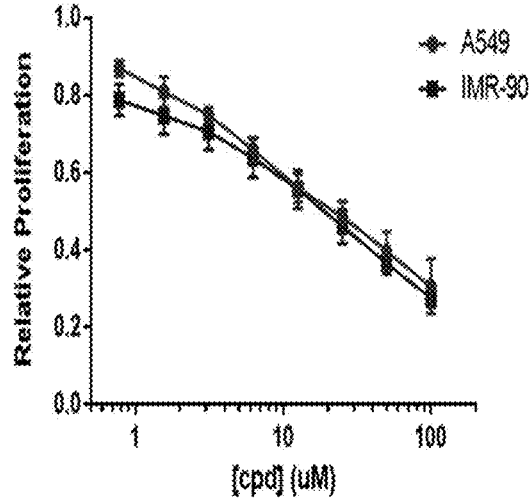
Figure 39:
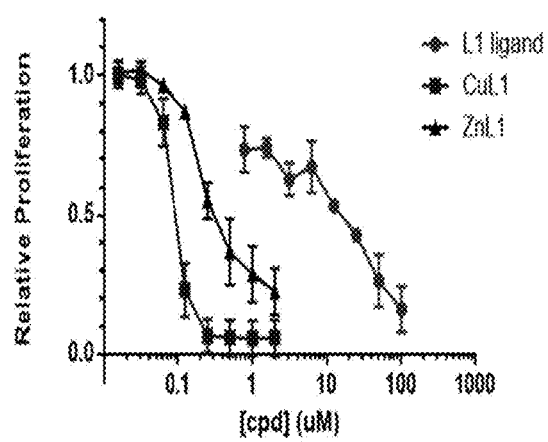
FIG. 39: Cell proliferation assays for A549 lung cancer cells and IMR-90 lung fibroblast cells for several compounds (Top: L1, CuL1, and ZnL1; Bottom: L1C, CuL1C, and ZnL1C).
Figure 39:
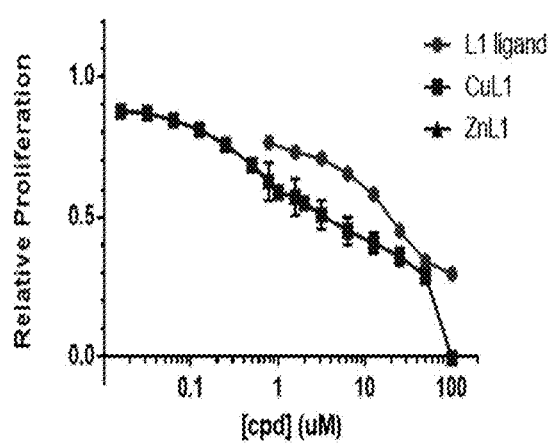
Figure 39:
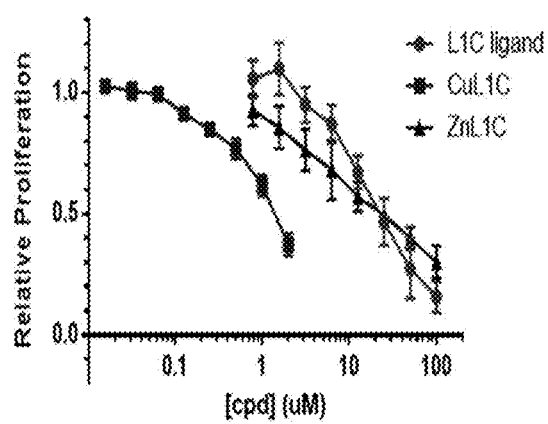
Figure 39:
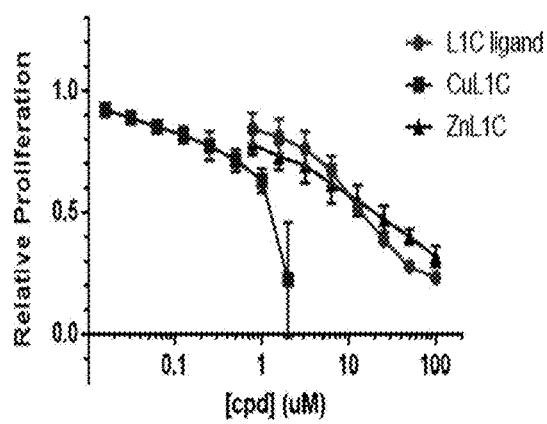
Figure 40:
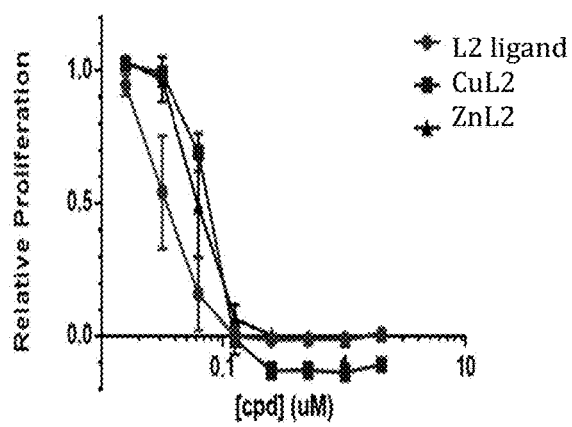
FIG. 40: Cell proliferation assays for A549 lung cancer cells and IMR-90 lung fibroblast cells for several compounds (Top: L2, CuL2, and ZnL2; Bottom: L2C2, CuL2C2, and ZnL2C2).
Figure 40:
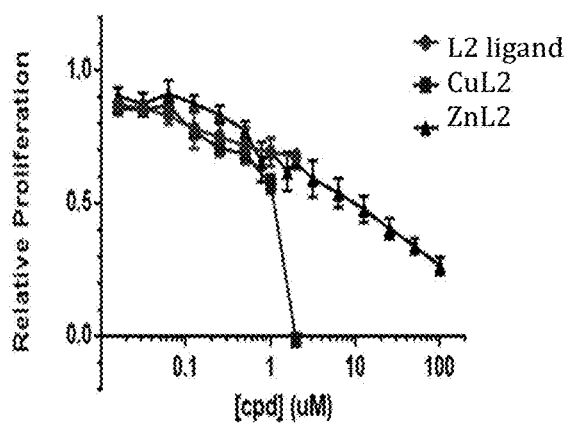
Figure 40:
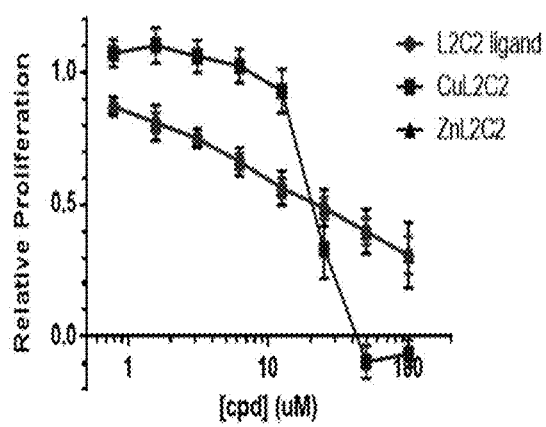
Figure 40:
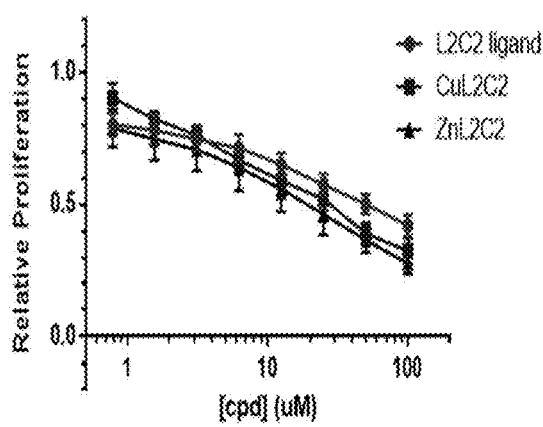

FIG. 36 (top panel) indicates that compound I-1 (NV3104) at 1 µM decreased cell viability. Other compounds tested (1-4 (NV40112), I-3 (NV40109), and I-14 (NV30164)) were less effective. The bottom panel of FIG. 36 shows proliferation as a function of compound concentration. Again, compound I-1 (NV3104) provided the most effective treatment.

Example Set F

In other experiments, the following compounds were tested:

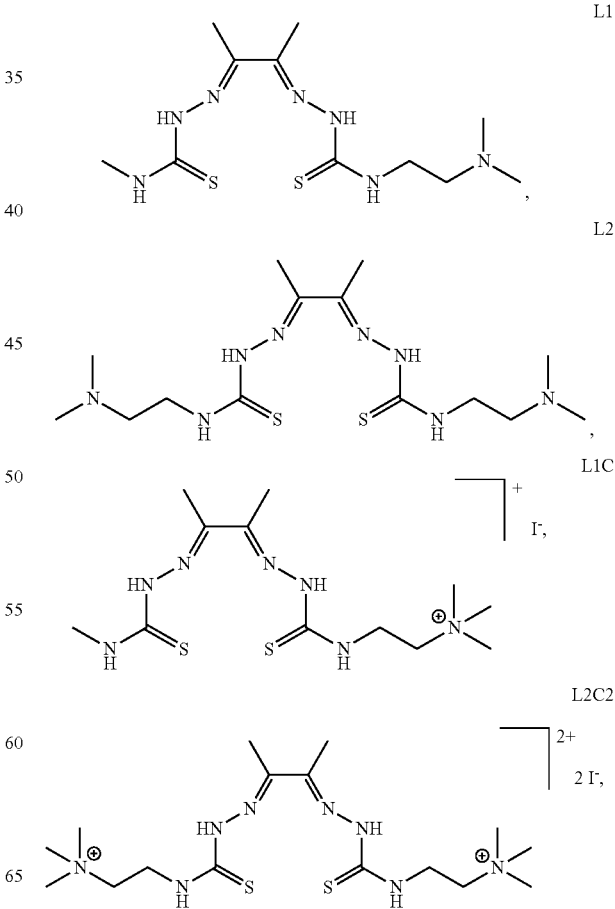

ML1

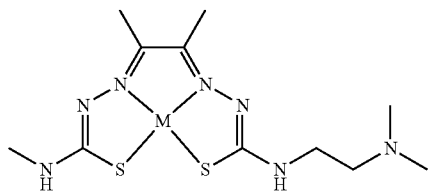

(e.g., M is Zn or Cu),

ML2

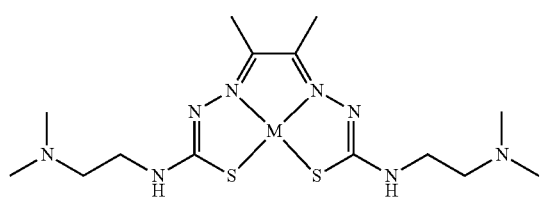

(e.g., M is Zn or Cu),

ML1C

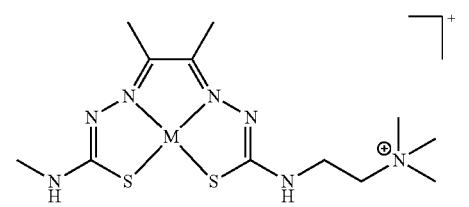

(e.g., M is Zn or Cu),

ML2C2

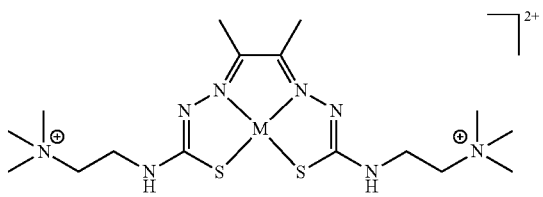

(e.g., M is Zn or Cu),

I-72

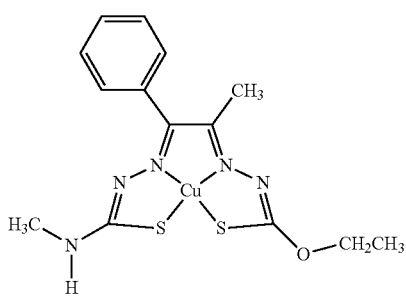

(L2-22; MW=398.99), and

L2-23

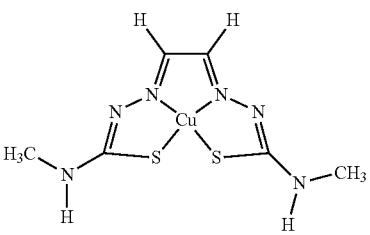

(MW=293.85).

FIGS. 37-40 show that some compounds containing Cu appear to have a greater activity in cancer cells (A549) compared to some compounds containing Zn. FIGS. 37-40 indicate that the ligands themselves appear to reduce cancer cell growth.

Figure 41:
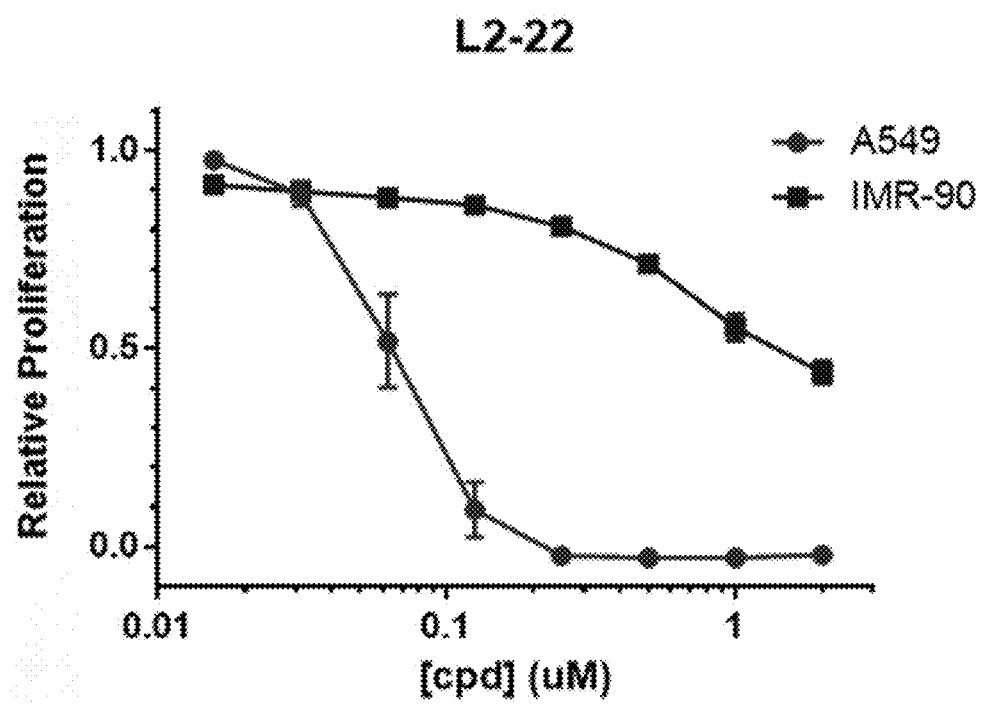
FIG. 41: Cell proliferation assays for A549 lung cancer cells for compounds L2-22 and L2-23.
Figure 41:
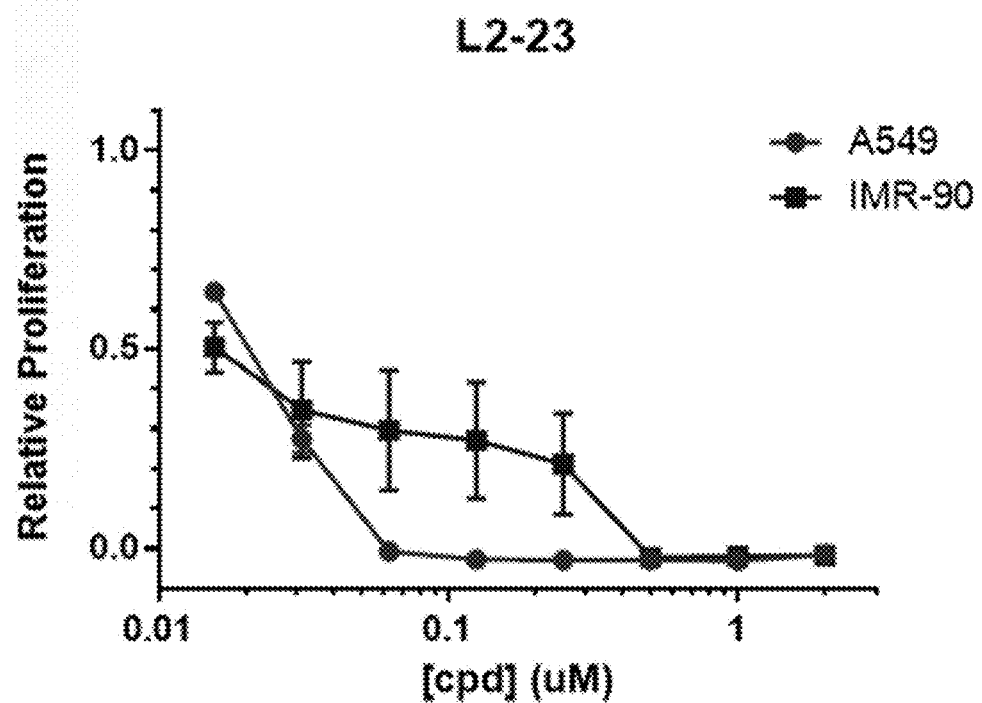

FIG. 41 shows that other compounds containing Cu appear to have activity in reducing cancer cell (A549) growth.

Example Set G

Figure 42:
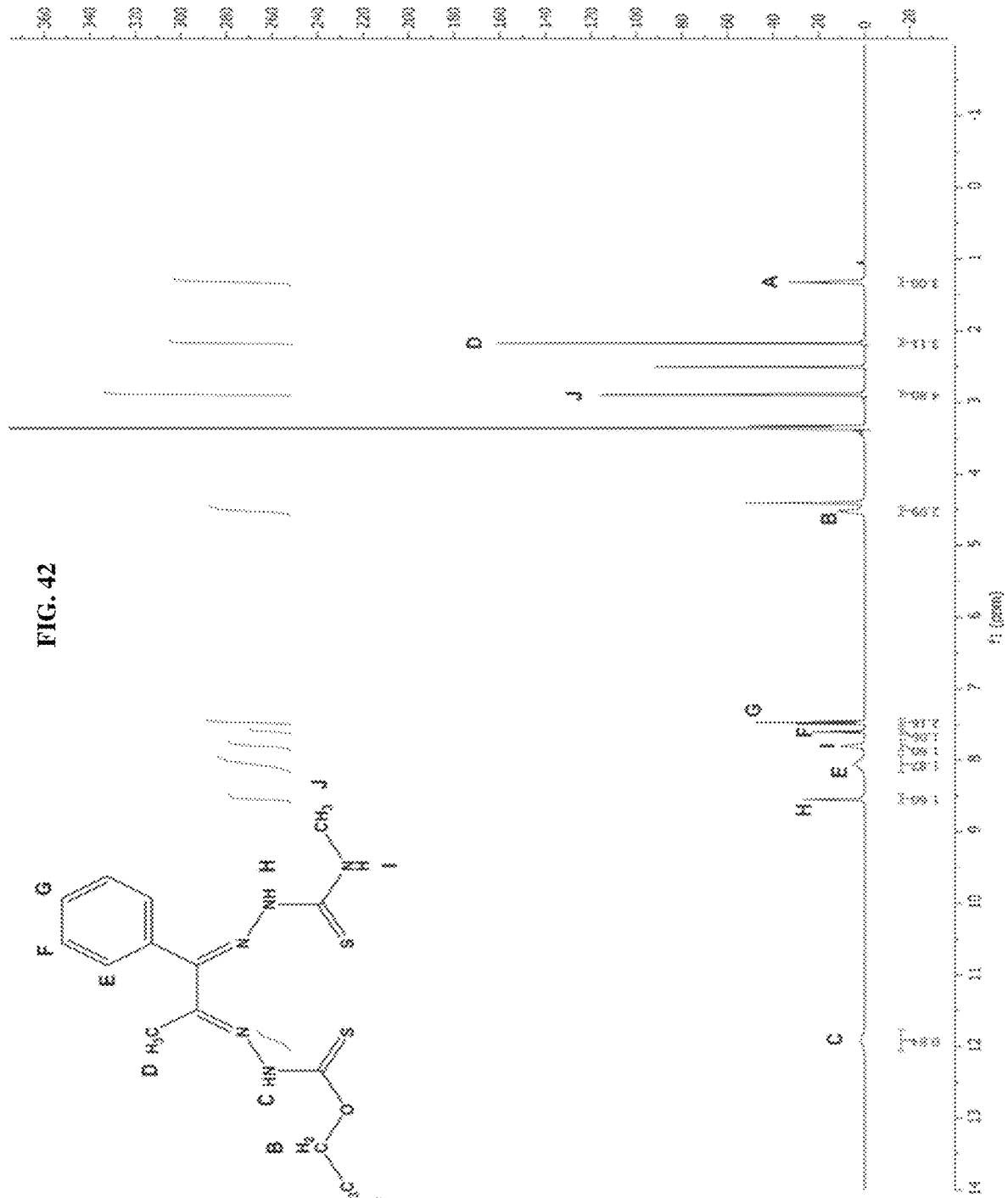
FIG. 42: The $^1$H NMR spectrum of compound I-75.
Figure 43:
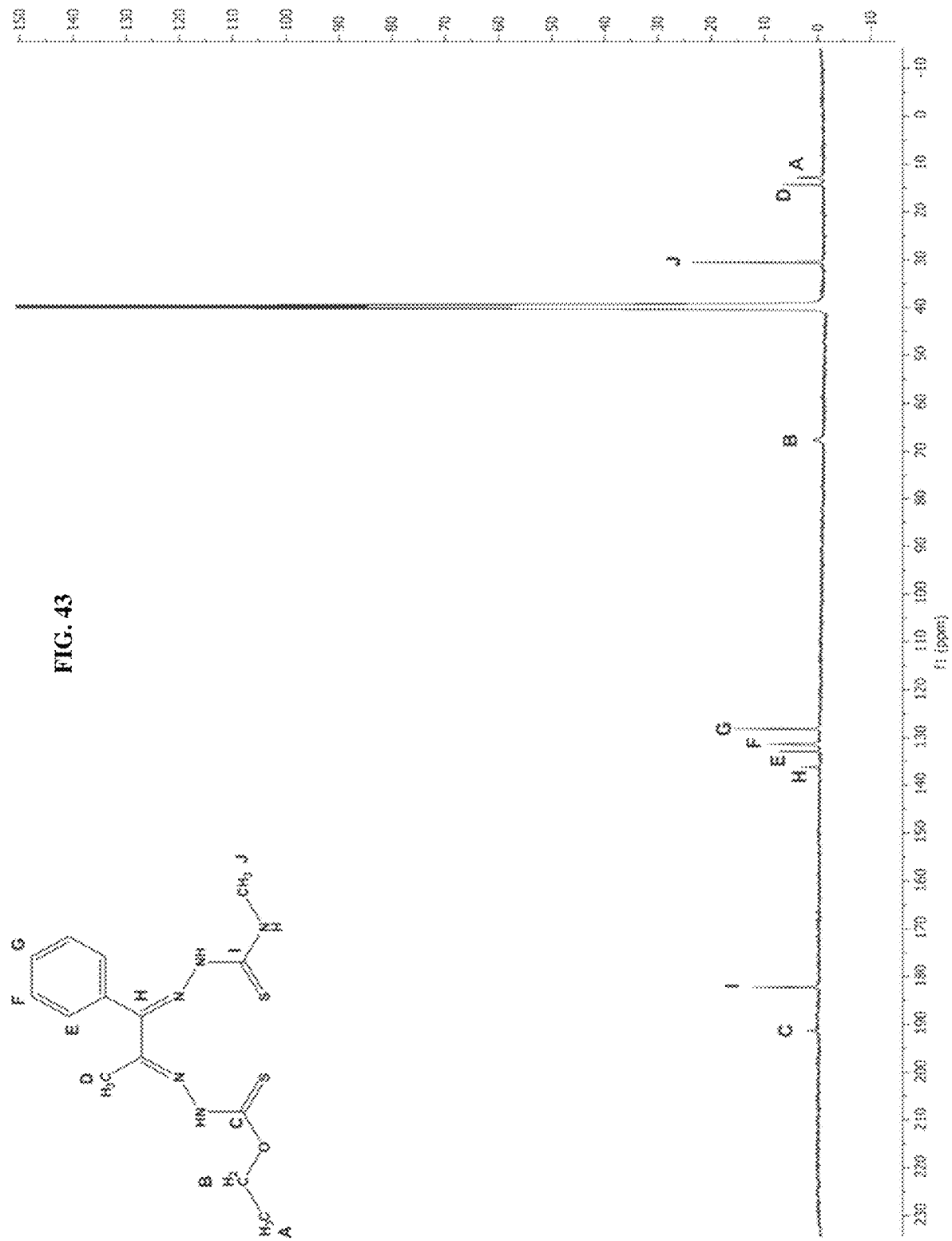
FIG. 43: The $^{13}$C NMR spectrum of compound I-75.

In other experiments, FIG. 42 and FIG. 43 show the $^1$H NMR and $^{13}$C NMR spectra of 1-75, respectively.

The headings used in the disclosure are not meant to suggest that all disclosure relating to the heading is found within the section that starts with that heading. Disclosure for any subject may be found throughout the specification.

It is noted that terms like "preferably," "commonly," and "typically" are not used herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used in the disclosure, "a" or "an" means one or more than one, unless otherwise specified. As used in the claims, when used in conjunction with the word "comprising" the words "a" or "an" means one or more than one, unless otherwise specified. As used in the disclosure or claims, "another" means at least a second or more, unless otherwise specified. As used in the disclosure, the phrases "such as", "for example", and "e.g." mean "for example, but not limited to" in that the list following the term ("such as", "for example", or "e.g.") provides some examples but the list is not necessarily a fully inclusive list. The word "comprising" means that the items following the word "comprising" may include additional unrecited elements or steps; that is, "comprising" does not exclude additional unrecited steps or elements.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as an illustrative basis for the claims and as a representative basis for teaching one skilled in the art to employ the present invention in any appropriate manner. Indeed, various modifications of the invention in addition to those described herein will become apparent to those skilled in the art from the foregoing description and the accompanying figures. Such modifications are intended to fall within the scope of the appended claims.

What is claimed is:
1. A compound selected from
(a) Formula (Ia)

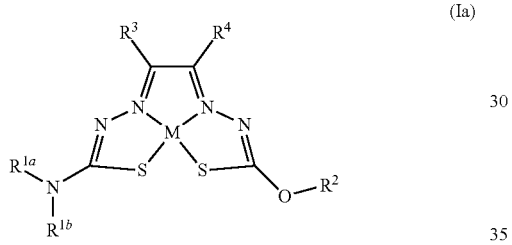

and salts, optical isomers, geometric isomers, salts of isomers, and derivatives thereof; and
(b) Formula (Ib)

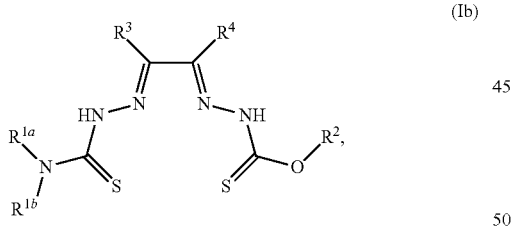

and salts, optical isomers, geometric isomers, salts of isomers, and derivatives thereof;
wherein
$R^{1a}$ is H, halogen, —CN, hydroxy (—OH), methanoyl (—COH), carboxy (—CO$_2$H), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl, which methanoyl (—COH), carboxy (—CO$_2$H), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, —CF$_3$, —OCF$_3$, or $C_1$-$C_3$ alkoxy;

$R^{1b}$ is H, halogen, —CN, hydroxy (—OH), methanoyl (—COH), carboxy (—CO$_2$H), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl, which methanoyl (—COH), carboxy (—CO$_2$H), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, —CF$_3$, —OCF$_3$, or $C_1$-$C_3$ alkoxy;

$R^{1a}$ and $R^{1b}$ are optionally bonded together with their attached nitrogen to form heterocyclyl or heteroaryl, which heterocyclyl or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, —CF$_3$, —OCF$_3$, or $C_1$-$C_3$ alkoxy;

$R^2$ is H, halogen, —CN, hydroxy (—OH), methanoyl (—COH), carboxy (—CO$_2$H), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl, which methanoyl (—COH), carboxy (—CO$_2$H), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, —CF$_3$, —OCF$_3$, or $C_1$-$C_3$ alkoxy;

$R^3$ is H, halogen, —CN, hydroxy (—OH), methanoyl (—COH), carboxy (—CO$_2$H), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl, which methanoyl (—COH), carboxy (—CO$_2$H), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, —CF$_3$, —OCF$_3$, or $C_1$-$C_3$ alkoxy;

$R^4$ is H, halogen, —CN, hydroxy (—OH), methanoyl (—COH), carboxy (—CO$_2$H), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl, which methanoyl (—COH), carboxy (—CO$_2$H), $C_1$-$C_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy;

R$^3$ and R$^4$ are optionally bonded together to form a ring with their attached carbons that is fused to the attached carbons of R$^3$ and R$^4$, where the ring that is fused is cycloalkyl, heterocyclyl, aryl, or heteroaryl, which cycloalkyl, heterocyclyl, aryl, or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$alkyl, C$_1$-C$_3$ perfluoronated alkyl, —CF$_3$, —OCF$_3$, or C$_1$-C$_3$ alkoxy; and M is a divalent cation.

2. The compound of claim 1, wherein R$^{1a}$ is H, methyl, ethyl, C$_{1-5}$ alkyl, C$_3$ alkyl, n-propyl, isopropyl, ethoxy, methoxy, 5-hydroxy pyridyl, indolyl, 1,2,3,4-tetrahydroisoquinolyl, furyl, 1,2-methylenedioxyphenyl, 2,3-methylenedioxyphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl.

3. The compound of claim 1, wherein R$^{1a}$ is H, methyl, ethyl, n-propyl, or phenyl.

4. The compound of claim 1, wherein R$^{1a}$ is not H.

5. The compound of claim 1, wherein R$^{1b}$ is H, C$_1$, hydroxy (—OH), methyl, ethyl, C$_{1-5}$ alkyl, C$_3$ alkyl, C$_4$ alkyl, —CN, ethynyl, —CONH$_2$, —CON(CH$_3$)$_2$, 2-(morpholinyl)ethoxy, —CO-morpholin-4-yl, ethoxy, methoxy, 5-hydroxy pyridyl, indolyl, 1,2,3,4-tetrahydroisoquinolyl, 1,2-methylenedioxyphenyl, 2,3-methylenedioxyphenyl, furyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl.

6. The compound of claim 1, wherein R$^{1b}$ is H, methyl, ethyl, n-propyl, or phenyl.

7. The compound of claim 1, wherein R$^{1b}$ is not H.

8. The compound of claim 1, wherein R$^2$ is methyl, ethyl, C$_3$ alkyl, n-propyl, isopropyl, ethoxy, methoxy, 5-hydroxy pyridyl, indolyl, 1,2,3,4-tetrahydroisoquinolyl, furyl, 1,2-methylenedioxyphenyl, 2,3-methylenedioxyphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl.

9. The compound of claim 1, wherein R$^2$ is methyl, ethyl, n-propyl, or phenyl.

10. The compound of claim 1, wherein R$^3$ is H, C$_1$, hydroxy (—OH), methyl, ethyl, C$_{1-5}$ alkyl, C$_3$ alkyl, —CN, ethynyl, —CONH$_2$, —CON(CH$_3$)$_2$, 2-(morpholinyl)ethoxy, —CO-morpholin-4-yl, ethoxy, methoxy, 5-hydroxy pyridyl, indolyl, 1,2,3,4-tetrahydroisoquinolyl, 1,2-methylenedioxyphenyl, 2,3-methylenedioxyphenyl, furyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl.

11. The compound of claim 1, wherein R$^3$ is H, methyl, ethyl, n-propyl, or phenyl.

12. The compound of claim 1, wherein R$^4$ is H, C$_1$, hydroxy (—OH), methyl, ethyl, C$_{1-5}$ alkyl, C$_3$ alkyl, —CN, ethynyl, —CONH$_2$, —CON(CH$_3$)$_2$, 2-(morpholinyl)ethoxy, —CO-morpholin-4-yl, ethoxy, methoxy, 5-hydroxy pyridyl, indolyl, 1,2,3,4-tetrahydroisoquinolyl, 1,2-methylenedioxyphenyl, 2,3-methylenedioxyphenyl, furyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl.

13. The compound of claim 1, wherein R$^4$ is H, methyl, ethyl, n-propyl, or phenyl.

14. The compound of claim 1, wherein M is iron (Fe), nickel (Ni), palladium (Pd), cadmium (Cd), manganese (Mn), cobalt (Co), copper (Cu), or zinc (Zn).

15. The compound of claim 1, wherein M is Cu.

16. The compound of claim 1, wherein the compound of Formula (I) is I-1.

17. The compound of claim 1, wherein (a) $R^{1a}$ is H, $R^{1b}$ is methyl, $R^2$ is ethyl, $R^3$ is methyl, $R^4$ is methyl, M is Cu, or combinations thereof; (b) $R^{1a}$ is methyl, $R^{1b}$ is H, $R^2$ is ethyl, $R^3$ is methyl, $R^4$ is methyl, M is Cu, or combinations thereof; (c) $R^{1a}$ is H, $R^{1b}$ is methyl, $R^2$ is ethyl, $R^3$ is methyl, $R^4$ is methyl, M is Zn, or combinations thereof; or (d) $R^{1a}$ is methyl, $R^{1b}$ is H, $R^2$ is ethyl, $R^3$ is methyl, $R^4$ is methyl, M is Zn, or combinations thereof.

18. The compound of claim 1, wherein $R^{1a}$ is H or $R^{1b}$ is H, but both Ria and $R^{1b}$ are not H.

19. A composition comprising the compound of claim 1.

20. A pharmaceutical composition comprising the compound of claim 1.

21. A method for providing an animal with a compound comprising one or more administrations of one or more compositions comprising the compound of claim 1, wherein the compositions may be the same or different if there is more than one administration.

22. A method for treating an animal for a disease, comprising one or more administrations of one or more compositions comprising the compound of claim 1, wherein (a) the compositions may be the same or different if there is more than one administration, (b) the animal has the disease, and (c) the disease is acute lymphoblastic leukemia, astrocytoma, basal cell carcinoma, bladder cancer, bone marrow cancer, breast cancer, chronic lymphocytic leukemia (CLL), CNS cancer, colon cancer, colorectal cancer, endometrial cancer, gastric cancer, glioblastoma, glioblastoma multiforme, glioma, gliosarcoma, hepatocellular carcinoma, kidney cancer, leukemia, liver cancer, lung cancer, lymphoma, melanoma, malignant nerve sheath tumors, medulloblastoma, meningioma, multiple myeloma, nasopharyngeal carcinoma, neuroblastoma, non-Hodgkin lymphoma, non-small cell lung cancer, oral cancer, ovarian cancer, pancreatic cancer, prostate cancer, rectal cancer, renal cancer, renal cell carcinoma, rhabdomyosarcoma, squamous cell carcinoma, stomach cancer, thyroid cancer, uterine cancer, cancers that can result in metastasis, cancers resulting from metastasis, or cancerous tumors thereof.

23. The method of claim 22, wherein the method does not include treating leukemia.

24. The method of claim 22, wherein at least one of the one or more compositions further comprises a formulary ingredient.

25. The method of claim 22, wherein at least one of the one or more administrations comprises parenteral administration, a mucosal administration, intravenous administration, subcutaneous administration, topical administration, intradermal administration, oral administration, sublingual administration, intranasal administration, or intramuscular administration.

26. The method of claim 22, wherein if there is more than one administration at least one composition used for at least one administration is different from the composition of at least one other administration.

27. The method of claim 22, wherein the compound of at least one of the one or more compositions is administered to the animal in an amount of from about 0.005 mg/kg animal body weight to about 50 mg/kg animal body weight.

28. The method of claim 22, wherein the animal is a human, a rodent, or a primate.

29. The method of claim 22, wherein the animal is in need of the treatment.

30. The method of claim 22, wherein the method is for treating leukemia, lung cancer, non-small cell lung cancer, colorectal cancer, colon cancer, rectal cancer, CNS cancer, glioblastoma, glioblastoma multiforme, gliosarcoma, astrocytoma, melanoma, cutaneous malignant melanoma, melanoma tumorigenesis, ovarian cancer, kidney cancer, prostate cancer, breast cancer, or cancerous tumors thereof.

31. The method of claim 22, wherein the method is for treating lung cancer, non-small cell lung cancer, colorectal cancer, colon cancer, rectal cancer, CNS cancer, glioblastoma, glioblastoma multiforme, gliosarcoma, astrocytoma, melanoma, cutaneous malignant melanoma, melanoma tumorigenesis, ovarian cancer, kidney cancer, prostate cancer, breast cancer, or cancerous tumors thereof.

32. The method of claim 22, wherein the method is for treating cancerous tumors.

33. A method for preparing a compound of claim 1 comprising,
(a) reacting a compound of Formula (II) with a compound of Formula (III) to result in a mixture comprising a compound of Formula (IV) and
(b) reacting a compound of Formula (IV) with a compound of Formula (V) to result in a mixture comprising a compound of Formula (Ib),
wherein Formula (II) is

Formula (III) is

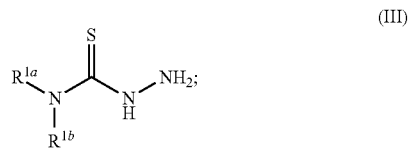

Formula (IV) is

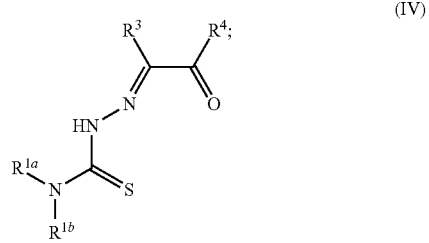

and
Formula (V) is

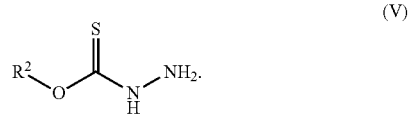

34. The method of claim 33, wherein the method further comprises recovering the compound of Formula (Ib).

35. The method of claim 33, wherein the method further comprises
 (c) reacting the compound of Formula (Ib) with a compound of Formula (VI) and
 (d) recovering a compound of Formula (Ia),
wherein
 Formula (VI) is M:anion (VI).

36. The method of claim 35, wherein the anion is a weak base, acetate, acetate monohydrate, acetate dihydrate, or acetate tetrahydrate.

37. The method of claim 35, wherein the compound of Formula (VI) is copper (II) acetate monohydrate, nickel (II) acetate tetrahydrate, or zinc (II) acetate dihydrate.

* * * * *